(12) United States Patent
Boevink et al.

(10) Patent No.: US 6,211,431 B1
(45) Date of Patent: Apr. 3, 2001

(54) PLANT TRANSCRIPTION REGULATORS FROM CIRCOVIRUS

(75) Inventors: Petra Christina Boevink, Lyneham; Brian Peter Surin, Rivett; Paul Konrad Keese, Curtin; Paul Wing Gay Chu, Florey; Peter Michael Waterhouse, O'Connor; Rafiqul Islam Khan, Giralang; Philip John Larkin, Weston; William Clark Taylor, Bungendore; Jerry Stuart Marshall, Aranda, all of (AU)

(73) Assignee: Commonwealth Scientific and Industrial Research Organization, Campbell (AU)

( * ) Notice: Subject to any disclaimer, the term of this patent is extended or adjusted under 35 U.S.C. 154(b) by 0 days.

(21) Appl. No.: 08/793,634

(22) PCT Filed: Aug. 30, 1995

(86) PCT No.: PCT/AU95/00552

§ 371 Date: Jun. 9, 1997

§ 102(e) Date: Jun. 9, 1997

(87) PCT Pub. No.: WO96/06932

PCT Pub. Date: May 7, 1996

(30) Foreign Application Priority Data

Aug. 30, 1994 (AU) .................................................. PM 7770
Nov. 7, 1994 (AU) .................................................. PM 9281

(51) Int. Cl.$^7$ ........................... C12N 15/33; C12N 15/82; C12N 15/90; A01H 5/00
(52) U.S. Cl. ..................... 800/278; 435/69.1; 435/320.1; 435/468; 536/24.1; 800/280; 800/288; 800/298; 800/301; 800/302
(58) Field of Search .............................. 435/69.1, 320.1, 435/410, 419, 468; 536/24.1, 23.72, 23.6; 800/301, 302, 278, 280, 288, 295, 298, 279

(56) References Cited

FOREIGN PATENT DOCUMENTS 43 06 832 C1    2/1994  (DE) .............................. C12N/15/82

OTHER PUBLICATIONS

Kim et al, Plant Mol. Biol., vol. 24, pp. 105–117, 1994.*
Boevink, et al. (1995) "Sequence of Subterranean Clover Stunt Virus DNA: Affinities with the Geminiviruses", Virology 207:354–361.

Boevink, et al. Abstracts of the 9th International Congress of Virology, Aug. 8–13, 1993, Glosgow, Scotland, U.K., P 68–1 "Subterranean Clover Stunt Virus—A Hypervariable DNA Virus".

Chu, et al. (1993) "Replication of Subterranean clover stunt virus in pea and subterranean clover protoplasts", Virus Res. 27:173–183.

Chu, et al. (1993) "Putative full–length clones of the genomic DNA segments of subterranean clover stunt virus and identification of the segment coding for the viral coat protein", Virus Res. 27:161–171.

Karan, et al. (1994) "Evidence for two groups of banana bunchy top virus isolates", Journal of General Virology 75:3541–3546.

Katul, et al. (1995) "Sequence analysis of a faba bean necrotic yellows virus DNA component containing a putative replicase gene", Journal of General Virology 76:475–479.

Surin, et al. Abstracts of the 9th International Congress of Virology, Aug. 8–13, 1993, Glosgow, Scotland, U.K., P 62–1, The Subterranean Clover Stunt Virus Genome Consists of Micro–Chromosomes Encoding Single.

Wu, et al. (1994) "Nucleotide Sequences of Two Circular Single–Stranded DNAs Associated with Banana Bunchy top Virus", Phytopathology 84(9):952–958.

Xie, et al. (1995) "Molecular Cloning, Sequence Analysis, and Detection of Banana Bunchy Top Virus in Hawaii", Phytopathology 85(3):339–347.

* cited by examiner

Primary Examiner—Elizabeth F. McElwain
Assistant Examiner—Ashwin D. Mehta
(74) Attorney, Agent, or Firm—Scully, Scott, Murphy & Presser

(57) ABSTRACT

The present invention is directed to transcription regulators and transcription regulator-like sequences of nanovirus origin. As used in the specification, the nanovirus group is consdiered to include subterranean clover stunt virus (SCSV), cocnut foliar decay virus (CFDV), banana bunchy top virus (BBTV), milk vetch dwarf cirus (MDV), and faba bean necrotic yellow virus (FBNYV). The transcription regulators and transcription regulator-like sequences of the instant invention are useful in genetic engineering of plants and in particular leguminous plants such as to facilitate or control expression of foreign genes. The transcription regulators and transcription regulator-like sequences of the present invention are also useful in facilitating different levels of expression in different plant tissue types.

38 Claims, 45 Drawing Sheets

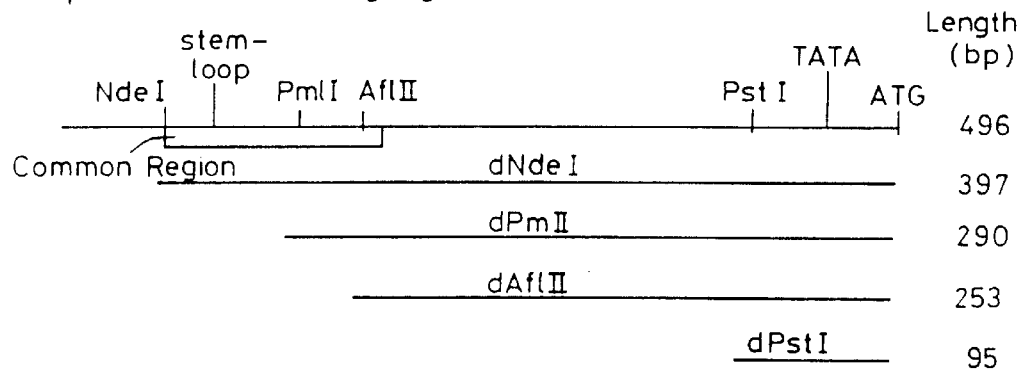
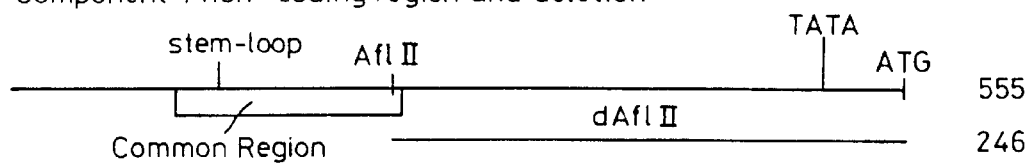
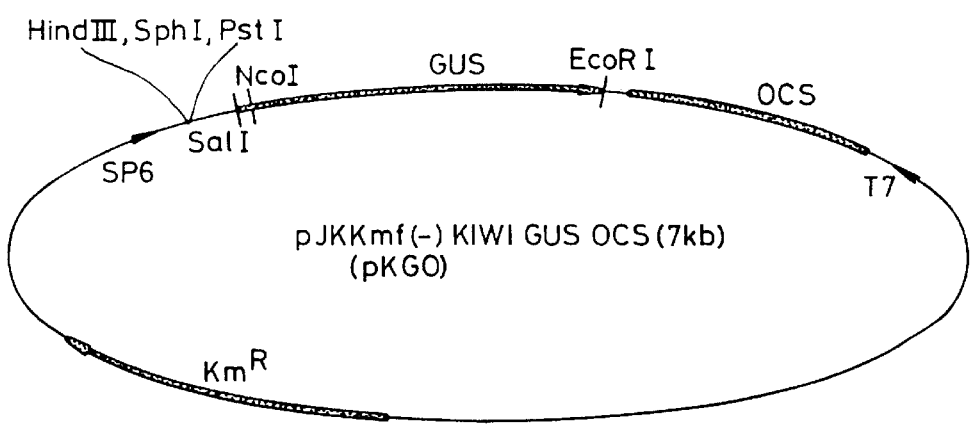
Fig. 4

COMPONENT 1

```
  1    TAGTATTACC CCCGTGCCGG GATCAGAGAC
 61    CCTTGGATTA AATGACACGT GGACGCTCAG
121    GAACGAATCT GACGGAAGAG CGTTCACACT
181    GTCTTGGGTC TATAAATAGA GTGCTTCTGA
241    GATTCTGGTG ATGGTTACAA TACATACTCA
301    GAAGTTTTAT ATAAAATAGG TATTATTATG
361    GTTTTAATTA TATTATGTTG TGCTGTTCCT
421    TTATCTTCGT CTTCTATTAT GAAGAGGAAG
481    GAAGAAACTG GTCCTCATCG TGAAAGAAGA
541    CAGAATAATA ATGATAATGT AAATAGATTT
601    ATGAGAATTA TTATTATTCT GTTCTTCGTC
661    TGGCGTCTGG AGAGAGAAAG GAATAATTGT
721    TGTCTTTACT TCGCCTCGAA GAAAGACACA
781    GAAGCTTCCT CGAAGCAGCG TATAACTTTA
841    ATTGCGGCTG TAAACGTGTC AAGTTGTGAG
901    ATTGTTTTAA TTTAATTCCG CGAAGCGATA
961    GATGACGTCA TATGTCTCCG TGCCTACGTC
```

*Fig. 6(i)*

COMPONENT 1 (cont.)

| | |
|---|---|
| ATTTGACCAA TAGTTGACTA GTATAATAGC | 60 |
| GATCTGTGAT GCTAGTGAAG CGCTTAAGCT | 120 |
| TAGATCTAGT TAGCGTACTT AGTACGCGTT | 180 |
| ACAGATTGTT CAGAATTTCA TAGCGAGATG | 240 |
| TATGAAGAAG GTGCTGGAGA TGCGAAGAAG | 300 |
| TTATGTATTG TAGGGATTGT AGTTTATGG | 360 |
| CGCTATGCTA AATCAACGAT GGACGCTTGG | 420 |
| ATGGCTTCAA GGATTACTGG TACTCCGTTT | 480 |
| TGGGCTGAAA GAAGAACTGA AGCGACGAAC | 540 |
| AGTTGATATG TTGTAATTTT ATATGGATTA | 600 |
| TGTGTTTTTT AAGCTTTTC TGTGTTTAA | 660 |
| AAGGTAGACG ACGATGTAGT GGATTACAGT | 720 |
| TTTCAAGTTG TGAGTGTTAT TGCTTTTGAG | 780 |
| ATTTGAATTT GGTTTTGGCG CGTTAGTGAA | 840 |
| TGGCTGAAAT AAGATAATAG ATATATTATT | 900 |
| TGTTAAGTGA TAAATGAAAC GAAGCGTTTT | 960 |
| AGCACGGGGC T | 1001 |

*Fig. 6(ii)*

COMPONENT 2

```
   1    TAGTATTACC CGACCTTGCC ACACCTCCTT
  61    ACTTTCTCTC TCTAAGCTTA TATGGCTAGA
 121    GAGATAGAGA GAGAAACATT CCTCTCCCTC
 181    GTCGGCGACG AAACTGCAAC TACTGGACAG
 241    AACAAAATTC GTCTTGGTGG ATTGAAGAAG
 301    GCGAGAGGCA GCGATTCTCA GAATCGCGAT
 361    ATTGGGATTC CGGTCATGAA GGGTTCGAAC
 421    GATCCCGAAG AAATGCAATT GAAGGATCCA
 481    TTGAAAGAGG AATATTGTTC CTGTTATGAT
 541    CTTCACGAGG ATTTAATGGC GGAACCAGAT
 601    GACGGAGGAG AAGGAAAGAC GAGCTTCGCG
 661    ACAGCCGGAG GGAAGACCCA GGACGTATTA
 721    ATTGCGTTTG ATGTTCCAG GTGTTCTTCG
 781    TTGAAGAACA GAGTTTTTGC AAGTACAAAA
 841    TTAGTTCATT TAATTGTGTT TGCCAACGTG
 901    AGACTTGTAA TTATCAATTG TTGAATAAAA
 961    GCGAAGCGGT AGCCGGTCAT AACACTGTTG
1021    CT
```

*Fig. 6(iii)*

COMPONENT 2 (cont.)

| | |
|---|---|
| GGAACACTTT CTCTCTCTAG AAAGTGTGAG | 60 |
| AGGTACTGTT TTACATTAAA TTACGCTACT | 120 |
| TTCTCTCAAG ACGAATTAAA CTATTTCGTT | 180 |
| AAACACCTCC AGGGATTTGT ATCGTTCAAG | 240 |
| AAATTTGGTA ATCGAGCTCA CTGGGAATT | 300 |
| TATTGCTGTA AAGAAACCCT AATTTCTGAA | 360 |
| AAGCGGAAGA CGATGGAGAT TTATGAAGAG | 420 |
| GATACTGCTC TTCGATGTAA GGCGAAGAAA | 480 |
| TTTCAGAAAC TCCGTCCATG GCAAATTGAG | 540 |
| AAGGAATTAA TCAGGTATGG ATGGTTTTAT | 660 |
| TATATGTATG CTCAAGACCC AGAGAGGAAT | 720 |
| GAGATGATGA ACTATCAGGC GATGGAGATG | 780 |
| TATAGGCCTG TAGATCTTTG TATTAGGAAG | 840 |
| GCACCTGACC CCACGCGCAT AAGTGAGGAC | 900 |
| GAATATATAT TATTGTTTTA ATTAATTCC | 960 |
| CCCTTGGAAC ACTATATATA GCAAGGTCGG | 1020 |
| | 1022 |

*Fig. 6(iv)*

COMPONENT 3

```
  1    TAGTATTACC  CCCGTGCCGG  GATCAGAGAC
 61    CCCTTGGATT  AGATGACACG  TGGACGCTCA
121    TGAACGAATC  TGACGGAAGA  GCGGACATAC
181    TGTATCTCTT  TACAGCTATA  TTGATGTGAC
241    GTAGGAAATT  GCTCGCTAAG  TTATTCTTTT
301    ATTAAATGAG  TGGCTATAAA  TAGATGTTTC
361    TCTTGTGTTA  ATGGCGTTAA  GGTATTTCTC
421    TATGAACGAG  CACTTGAAGG  AAATTAAGAA
481    TGCGTGTGCT  GTGTTCGAAG  GTTTAACAAA
541    ACGCTTCTCT  GGGTTTCTGG  AAGGTCTGTC
601    GTGTTTAGTT  AGATGGAAGA  AGAGCGTTGC
661    GATGCATTAC  AAGCTTTATG  GATTTGCAGA
721    GTTTCCTAAT  TACGGTGAAG  ACGATGTAGC
781    GCAATTAGAA  GTTGTATTTG  ATGATTTAGG
841    AGGTTCTATT  AAGATAGAAT  TATGAGATGT
901    TATTCTTTGA  ATTACTCCGC  GAAGCGGTGT
961    ATATGTCTCG  CCGACAGGCT  GGCACGGGGC
```

Fig. 6(v)

COMPONENT 3 (cont.)

| | | | |
|---|---|---|---|
| ATTTGACCAA | TAGTTGACTA | TGAATAATAG | 60 |
| GGATCTGTGA | TGCTAGTGAA | GCGCTTAAGC | 120 |
| GCACATGGAT | TATGGCCAC | ATGTCTAAAG | 180 |
| GTAAGATGCT | TTACTTCGCC | TCGAAGTAAA | 240 |
| CTGAAAGAAA | TTAATTTAAT | TCTAAATTAA | 300 |
| GTCTTCGTTG | TTTTACAACG | AAGCTTAGAA | 360 |
| TCATCTTCCT | GAAGAACTGA | AGGAGAAGAT | 420 |
| GAAGGAATTT | CTAGAGAATG | TAATTAAAGC | 480 |
| GAAGGAGTCT | GTTGAAGAAG | ACGACATACT | 540 |
| TGCATATTAT | GCAGAGGCGA | CGAAGAAGAA | 600 |
| AATAAATCTG | AAATGGAGAG | TTATGGAGGA | 660 |
| CATGGAAGAT | TTATATTATT | CAGAGTTAGG | 720 |
| TTATCACGAT | GGTGCAATTG | TAAATTGTAA | 780 |
| TATTGAGTTT | ATGTCTATTG | TAATTGATAG | 840 |
| AATTGTGATT | AATGAATAAA | GAGTTGTTAT | 900 |
| GTTATGTTTT | TGTTGGAGAC | ATATGACGTC | 960 |
| T | | | 991 |

*Fig. 6(vi)*

COMPONENT 4

```
  1    TAGTATTACC CCGTGCCGGG ATCAGAGACA
 61    CCTTGGATTA GATGACACGT GGACGCTCAG
121    GAACGAATCT GACGGAAGAG CGGACAAACG
181    AGAAGTGAAT GACAGCTGTC TTTGCTTCAA
241    AAGAATAAGC GTACTCAGTA CGCTTCGTGG
301    GTTGTATCAT CAACGAAGAA GTTAAGCTTT
361    CAGTGCGCTT AAGACATGTA CTCATGTCTG
421    ACAGGATTTC TTCTGTTGTG ATAGTATGCG
481    GTTAGTTAGT TGTTTTGTAA GTTTTACTGG
541    AGGTCAAGTT CAGTTGGGTA TGCAGCAAGA
601    TCCTATTGGG GGTTATTTGT ATCATGATGA
661    CAATCTGGAC ATCGAGTCAG ATTATCTGAA
721    AATTAATATT GTAAATGATA AAGGATTAGA
781    TCATACGATG CGTATTAAGG TGTAATTGTT
841    GTGTTATTTG GTAATTTATG CTTATAAGTA
901    TAATGAGGAT AATAATTGAA TTTGATTAAA
961    TGAGAGTCAC GTGATGTCTC CGCGACAGGC
```

*Fig. 6(vii)*

COMPONENT 4 (cont.)

| | | | |
|---|---|---|---|
| TTTGACTAAA | TGTTGACTTG | GAATAATAGC | 60 |
| GATCTGTGAT | GCTAGTGAAG | CGCTTAAGCT | 120 |
| CACATGGACT | ATGGCCCACT | GCTTTATTAA | 180 |
| GACGAAGTAA | AGAATAGTGG | AAAACGCGTA | 240 |
| CTTTATAAAT | AGTGCTTCGT | CTTATTCTTC | 300 |
| GTTCTGCGTT | TTAATGGCGG | ACTGGTTTCA | 360 |
| TGATTTTTCA | GATATTAAGG | CGTCTTCACA | 420 |
| AGGTAAATTA | TCTGAACCTA | GGAAGGTGTT | 480 |
| TAGTTTTTAT | GGAAGTAATA | GGAATGTTAG | 540 |
| TGATGGCGTT | GTTCGTCCAA | TAGGATATAT | 600 |
| TTATGGATAT | TATCAAGGAG | AGAAGACGTT | 660 |
| GCCTGATGAA | GATTTTTGGA | AGAGATTTAC | 720 |
| TGATAGGTGT | GATGTAAAAT | GTTATGTAGT | 780 |
| ATTATCAATA | AAAGAATTTT | TATTGTTATT | 840 |
| ATTCTATGAT | TAATTGTGAA | TTAATAAGAC | 900 |
| TTAACTCTGC | GAAGCTATAT | GTCTTTCACG | 960 |
| TGGCACGGGG | CT | | 1002 |

*Fig. 6(viii)*

COMPONENT 5

```
  1    TAGTATTACC  CCGTGCCGGG  GTCAGAGACA
 61    CCTTGGATTA  GATGACACGT  GGACGCTCAG
121    GAACGAATCT  GACGGAAGAG  CGTCATGGTC
181    GTATTGATTT  GACTTTACGC  GCTTTACTTT
241    TTTGCTCGCG  ACGAAGCAAA  GTGATTGTAG
301    AACACGGTTT  GATTGTGGGT  ATAAATATGT
361    ACGAAGATGG  TTGCTGTTCG  ATGGGGAAGA
421    TCGCGAATTG  CTTACAAACC  TCCTTCGTCT
481    AATAAGAGAG  ATGTTACTGG  AGCGGAGGTT
541    ATGAAGAAGG  TAATGTTGAT  TGCAACATTA
601    CTTATTGTGA  AGAGTAATTC  GCCTATTGCG
661    TTGATGGTGA  AAGAGTCTGT  TCAAGATACA
721    TCTTCTGGTA  CTGCTGGTAA  AGATGTAACT
781    TCAGGTATTA  GTCAGACCCA  GCATTTGTAT
841    ATCACACTGG  AGACGAGAAT  GTATATTGAT
901    TTGTTTTTAT  TCTTTGAATT  ACTCCGCGAA
961    TGACGTCATA  TGTCTCCGCG  ACAGGCTGGC
```

*Fig. 6(ix)*

COMPONENT 5 (cont.)

| | | | |
|---|---|---|---|
| TTTGACTAAA | TATTGACTTG | GAATAATAGC | 60 |
| GATCTGTGAT | GCTAGTGAAG | CGCTTAAGCT | 120 |
| CACATGTCTA | AAGAATAATG | CTTTACAGCT | 180 |
| AATTGCTTTA | AGTAAAGTAA | GATGCTTTAC | 240 |
| CTGCAGAAAT | TGATGCTTTA | ATTACCGGGT | 300 |
| TCTGTTCGTT | TTCTTCGTTG | TCATTTTACA | 360 |
| AAGGGTCTGA | GGTCTCAAAG | GAGAAAATAT | 420 |
| AAGGTTGTAA | GTCATGTGGA | GTCTGTTCTG | 480 |
| AAGCCATTCG | CTGATGGTTC | AAGGTATAGT | 540 |
| ACTATGGCTC | CTGGAGAATT | AGTTAATTAT | 600 |
| AATTGGAGTT | CGTCTTTCAG | TAATCCTTCG | 660 |
| GTTACGATTG | TTGGAGGAGG | AAAGCTTGAG | 720 |
| AAGTCTTTTA | GGAAGTTTGT | TAAGCTGGGT | 780 |
| TTAATTATTT | ATTCCAGTGA | TGCGATGAAG | 840 |
| GTATAATTGT | GATGATTAAT | GAATAAAGAG | 900 |
| GCGGTGTGTT | ATGTTTTTGT | TGGAGACATA | 960 |
| ACGGGGCT | | | 998 |

*Fig. 6(x)*

COMPONENT 6

| | | |
|---|---|---|
| 1 | CAGTATTACC | GCACCTCGCT TACCCTCCTC |
| 61 | AAAGCACTAG | TTGGGTGTTC ACACTTAACT |
| 121 | ATGAAAGCGT | TCAGTACGCT TGTTGGCAGC |
| 181 | GATTTATACA | ATTTAAATCC CGCAACACTA |
| 241 | GACTGAATCC | TCATCTGGAA ATTGCTAGGG |
| 301 | AGGAAGATAG | TAGAGTAGCT GGTCCCTGGG |
| 361 | ATAAGCGTAA | GCTGATGGAG AGATTTGAAG |
| 421 | CCTCTCTCTA | TAGGCGTTGT CTATCAAGGA |
| 481 | AGTGGAATTA | TGACTTACGC CCTTGGCAAG |
| 541 | CAGATTATAG | AACGATAATC TGGGTGTATG |
| 601 | TTGCAAGACA | TCTGTCATTG AAAGATGGTT |
| 661 | ATATGATGCA | TCTTGTGACT GCTGAGCCTA |
| 721 | TTAGTTCAGA | GTATGTGAAT TATGGTGTAA |
| 781 | ATACTAAGTA | TGAGCCATGT GTAATGCGGG |
| 841 | TTGCAAATGT | ACTCCCAGAT TTGGGAAAAT |
| 901 | GTTGAAAACT | CTGCGAAGGC AGAAGTTATA |
| 961 | TCGGGTAGTT | CGCGAAACAG GGTGAGGGAA |

*Fig. 6(xi)*

COMPONENT 6 (cont.)

| | | | |
|---|---|---|---|
| GCTTCCCTGG | GCCCACTATG | CCTACTAGAC | 60 |
| TTGAGGGCGA | AATTCCTATT | TTGCCCTTTA | 120 |
| ATGAGAGAGT | GGGACACGAT | CATTTACAGG | 180 |
| CATTGCGTCA | GGCTAAGTAT | ATTTTTAATG | 240 |
| ATGTAGAGAA | GGCGCAATTG | TACGCGATGA | 300 |
| AGTATGGGTT | GTTTATTAAG | AGAGGATCGC | 360 |
| AAGATGGAGA | AGAGATGAAA | ATTGCTGATC | 420 |
| AGATGGCTGA | AGAACAACGT | TGTTCTTCTG | 480 |
| AAGAAGTGAT | GCATTTGTTA | GAGGAAGAAC | 540 |
| GACCTGCTGG | TAATGAAGGC | AAATCTACAT | 600 |
| GGGGTTATCT | GCCTGGAGGA | AAGACACAAG | 660 |
| AGAATAATTG | GGTATTTGAC | ATACCCAGAG | 720 |
| TAGAACAGGT | TAAGAATAGG | GTAATGGTGA | 780 |
| ATGATAATCA | TCCTGTTCAT | GTAATTGTGT | 840 |
| TAAGTGAAGA | TAGAATAAAA | TTAATTCGTT | 900 |
| AAAAAAATGT | GTTTTGAGAG | AAGTCCCACA | 960 |
| GCGAGCAATA | TAAGGCGAGG | TGCGTAT | 1017 |

*Fig. 6(xii)*

COMPONENT 7

```
  1    TAGTATTACC  CCGTGCCGGG  ATCAGAGACA
 61    CCTTGGATTA  GATGACACGT  GGACGCTCAG
121    GAACGAATCT  GACGGAAGAG  CGGACATACG
181    GTATCTCTTT  ACAGCTATAT  TGATGTGACG
241    TAGGAAATTG  CTCGCTAAGT  TATTCTTTTC
301    TAAATGAGTG  GCTATAAATA  GTGTCGATGC
361    CTGTTCTGGT  TTTAAGCGAT  GGTCAGTTTT
421    GATGTTCTTG  TAAGCGATAG  CAGAAGAAGT
481    GTGATTAACG  TGAAGGTACT  GAGGTTGATT
541    AAGGTTATGT  TTCGTCTGTG  TTACAGATAC
601    TGTAAGATGG  AGCTATGGAC  TTCGTTGAAG
661    TTGCAGAGGA  AGCTTAATGG  TATATGTGTT
721    GTAAGTAATG  TTAAAGAGTT  GATTAATAGA
781    AATCCTATAT  GTTGTTTGTA  TCATATGGAC
841    TATGAGATAA  GAGTTGTTAT  TAATGCTTAT
901    TTTTATTCGC  GAAGCGGTGT  GTTATGTTTT
```

*Fig. 6(xiii)*

COMPONENT 7 (cont.)

| | | | |
|---|---|---|---|
| TTTGACTAAA | TATTGACTTG | GAATAATAGC | 60 |
| GATCTGTGAT | GCTAGTGAAG | CGCTTAAGCT | 120 |
| CACATGGATT | ATGGCCCACA | TGTCTAAAGT | 180 |
| TAAGATGCTT | TACTTCGCTT | CGAAGTAAAG | 240 |
| TGAAAGAAAT | TAATTTAATT | CTAATTAAAT | 300 |
| TGCCTCACAT | CGTATTCTTC | TTCGCATCGT | 360 |
| AGTTTTCCTG | AGATATACGA | TGTGAGCGAC | 420 |
| GTAGCTGTTG | AGGTCGAAGA | GAAGGTTCAA | 480 |
| GAAGCTGTTG | ATGAAGATAG | AGTTGGAGTG | 540 |
| AGACGAGAAC | TGAAGATTAC | GTTGTTGGGT | 600 |
| TCTTCAGGCA | AGTATTCAGT | TCAATCTTTG | 660 |
| AGTAATTACT | GTATAGGTAT | TGATATGTTT | 720 |
| TGTAAATGGA | TTACATCTGT | TCAAGGTGTT | 780 |
| GAAGAGTAAT | TAATAGTAAT | TATGATTAAT | 840 |
| GAGGAATAAA | GAATGATTAA | TATTGTTTAA | 900 |
| TGTTGGAGAC | ATCACGTGAC | TCTCACGTGA | 960 |
| TGTCTCCGCG | ACAGGCTGGC | ACGGGCT | 988 |

*Fig. 6(xiv)*

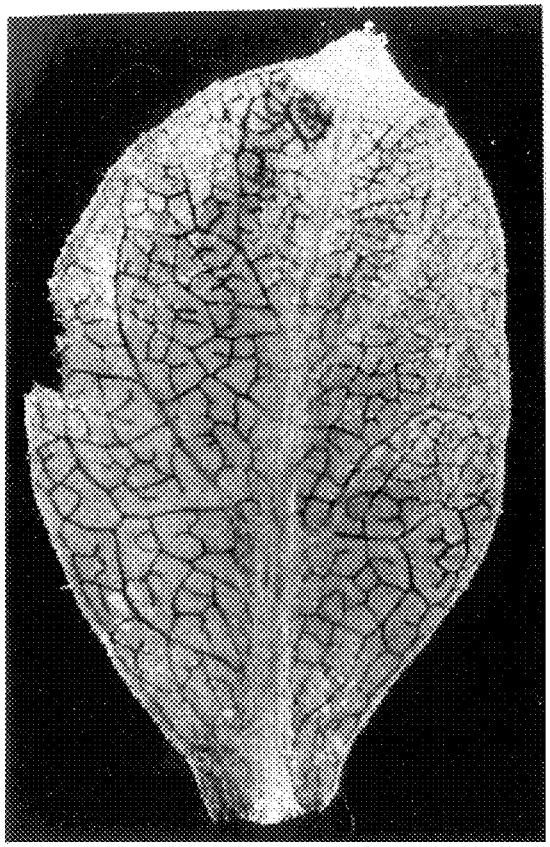 
Tobacco  Subterranean Clover
Fig. 7

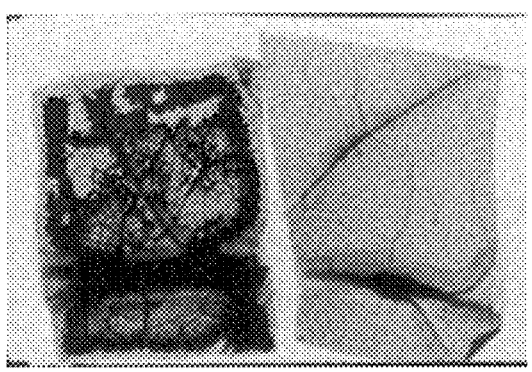
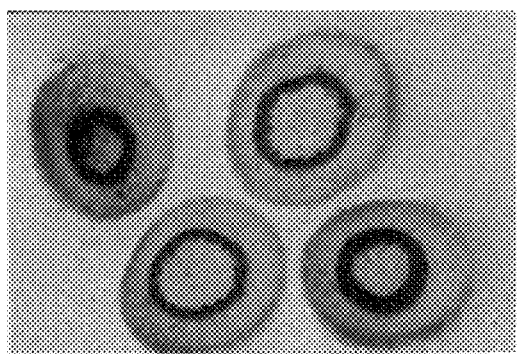
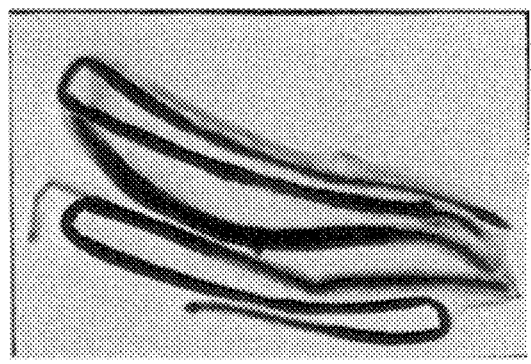
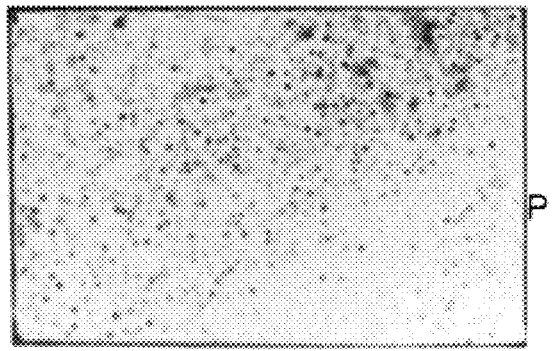
Fig. 8b

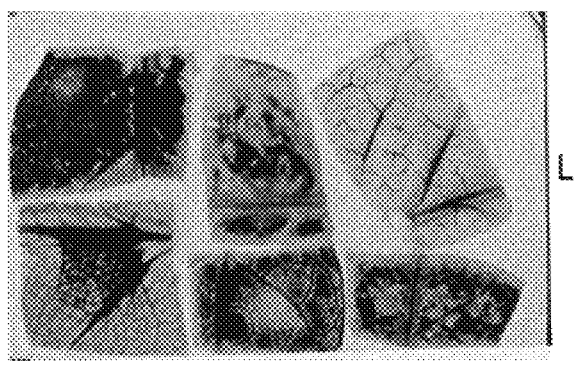
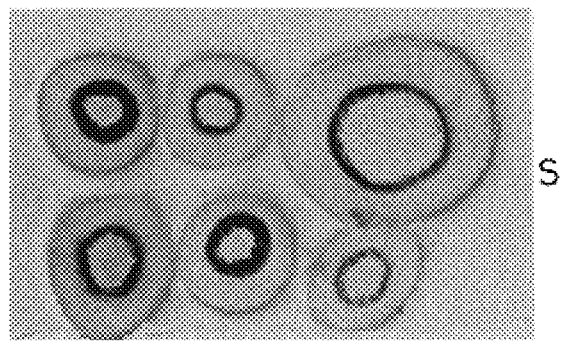
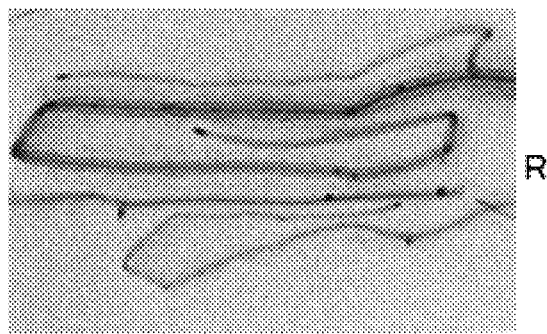
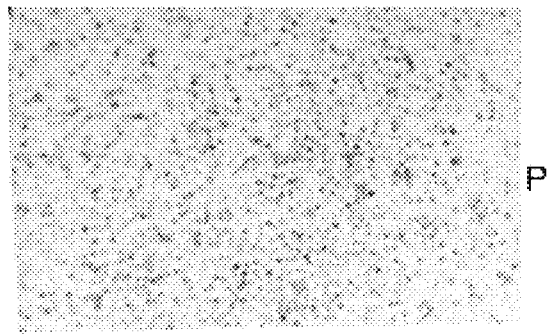
Fig. 8c

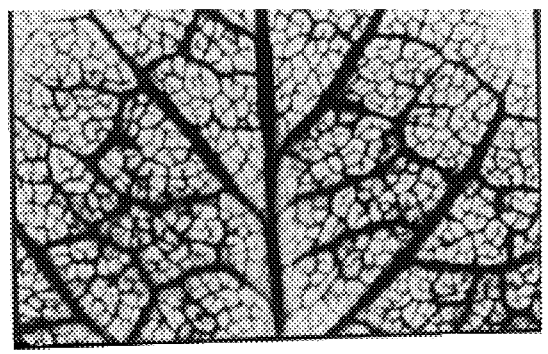
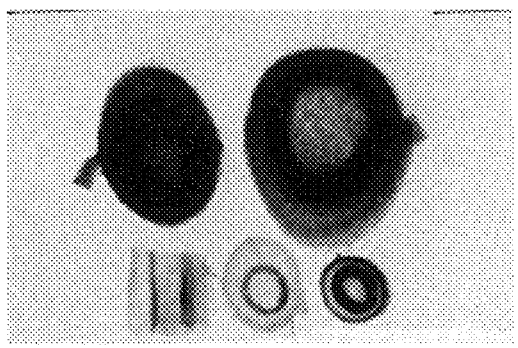
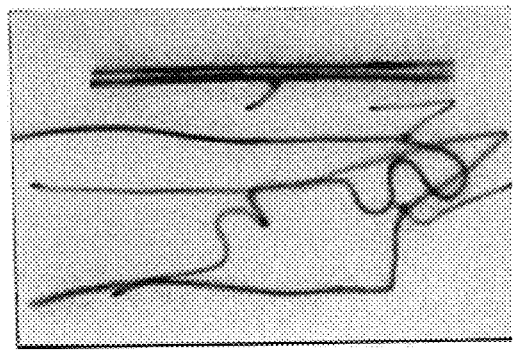
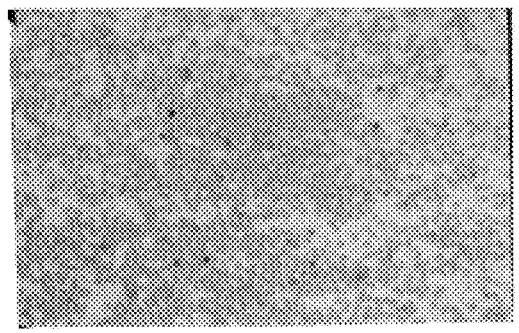
Fig. 8e

S7nc
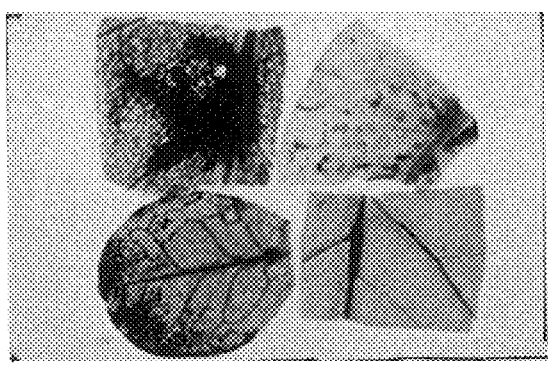
L
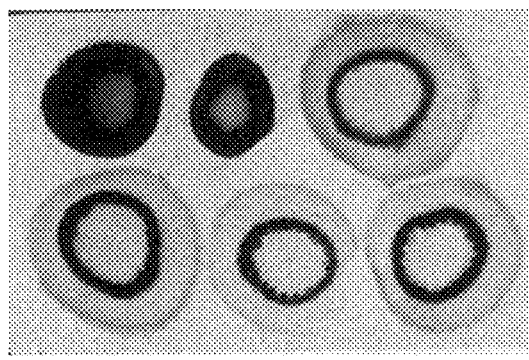
S
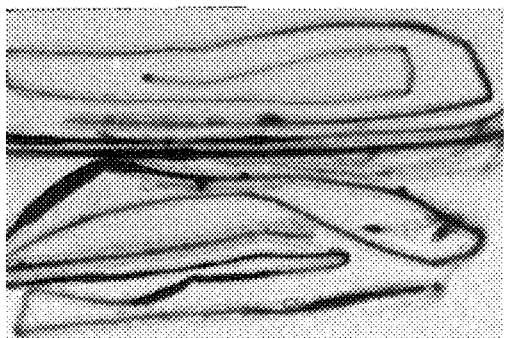
R
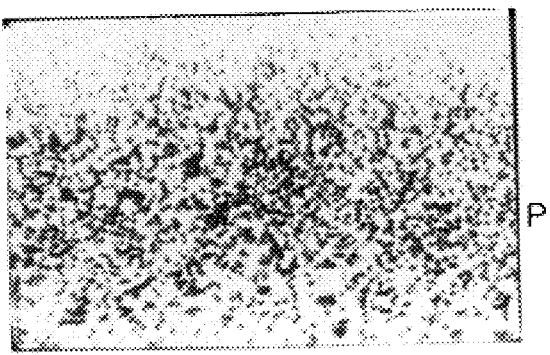
P
Fig.8f

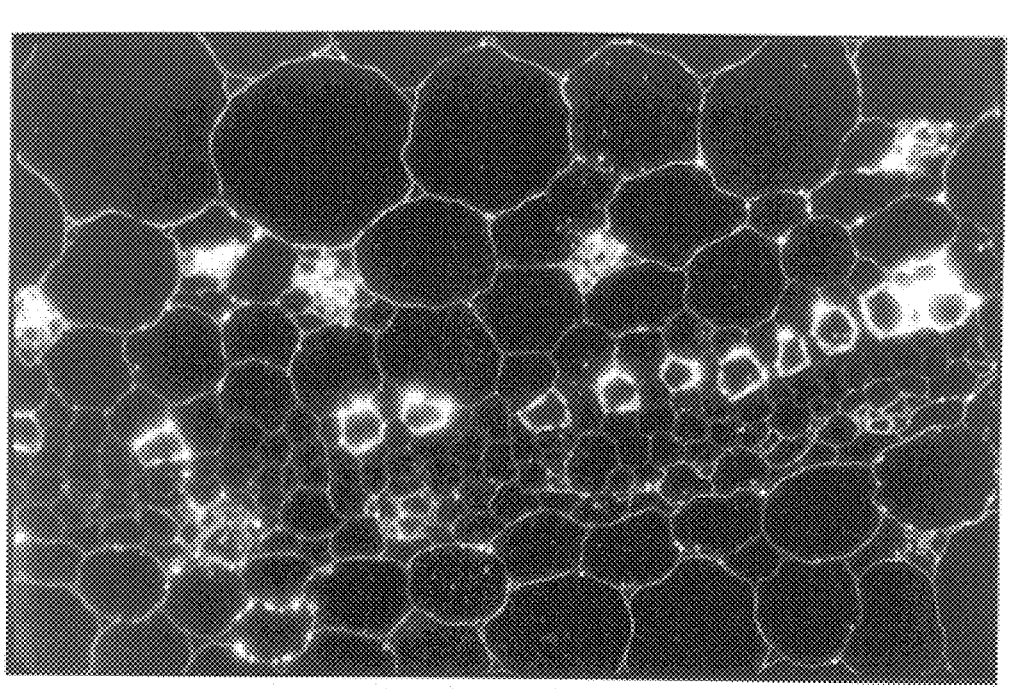
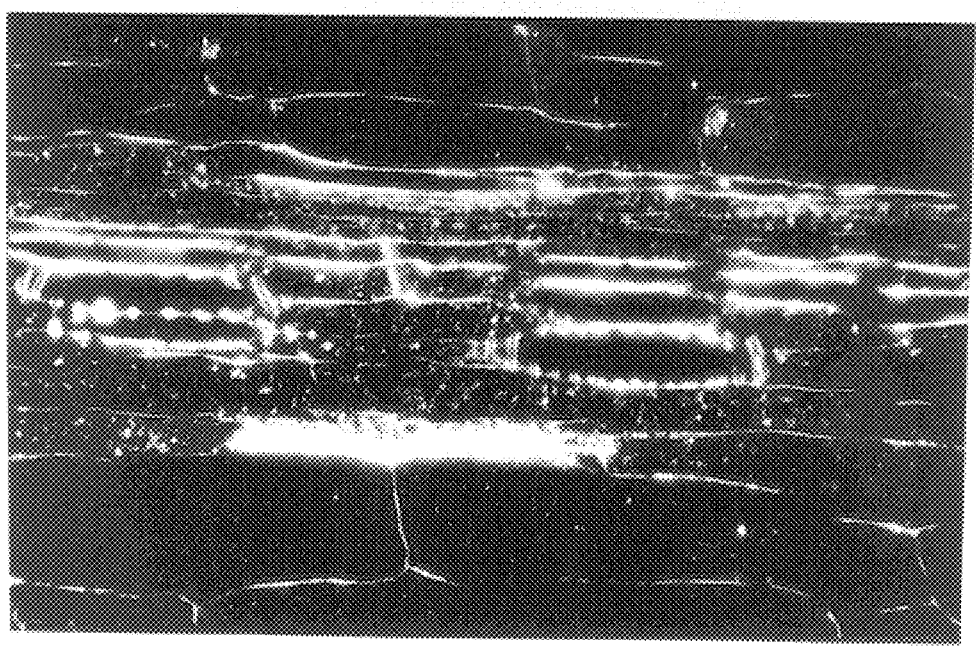
Fig. 9a

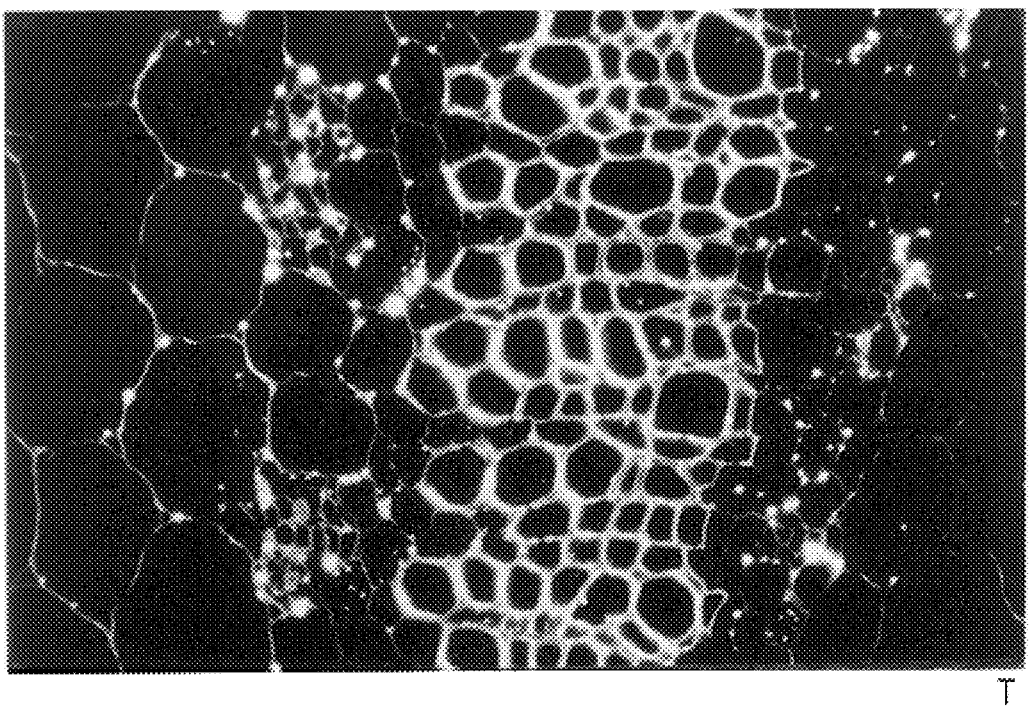
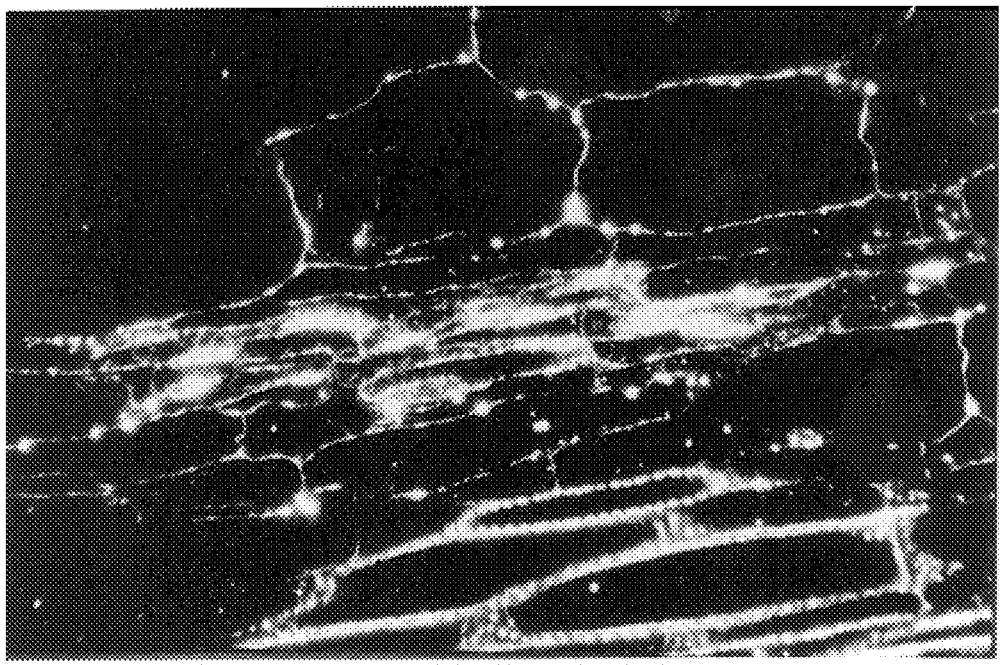
Fig. 9b

S4nc
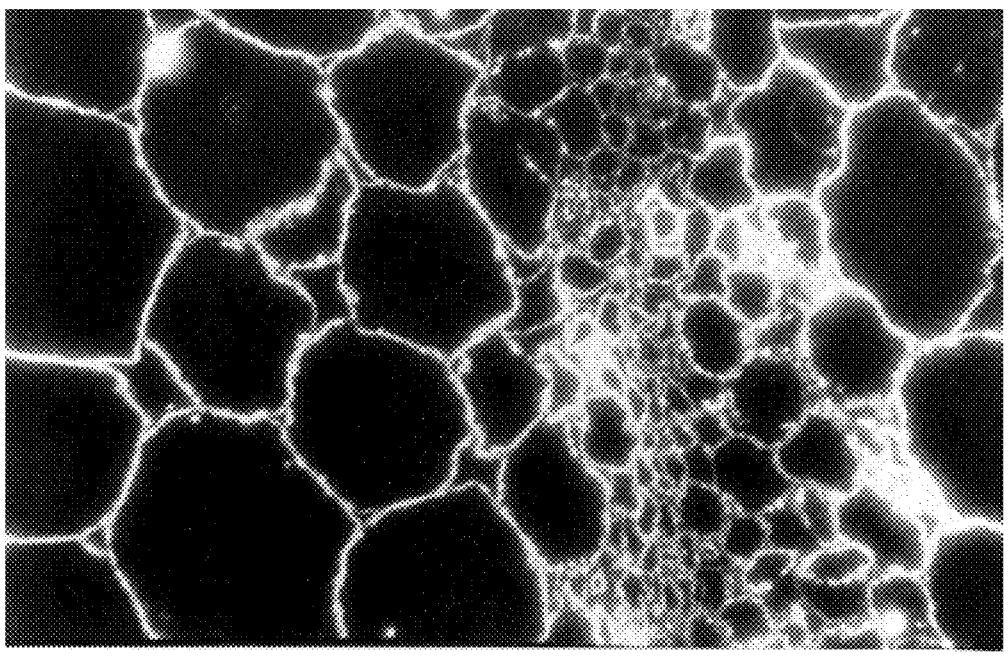
T
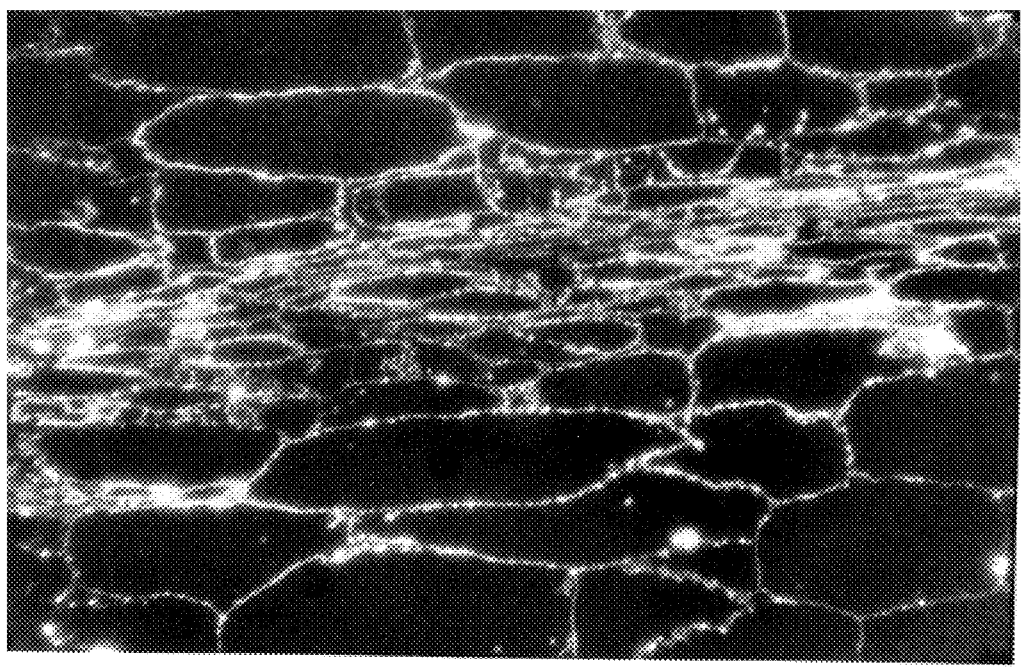
L
Fig. 9c

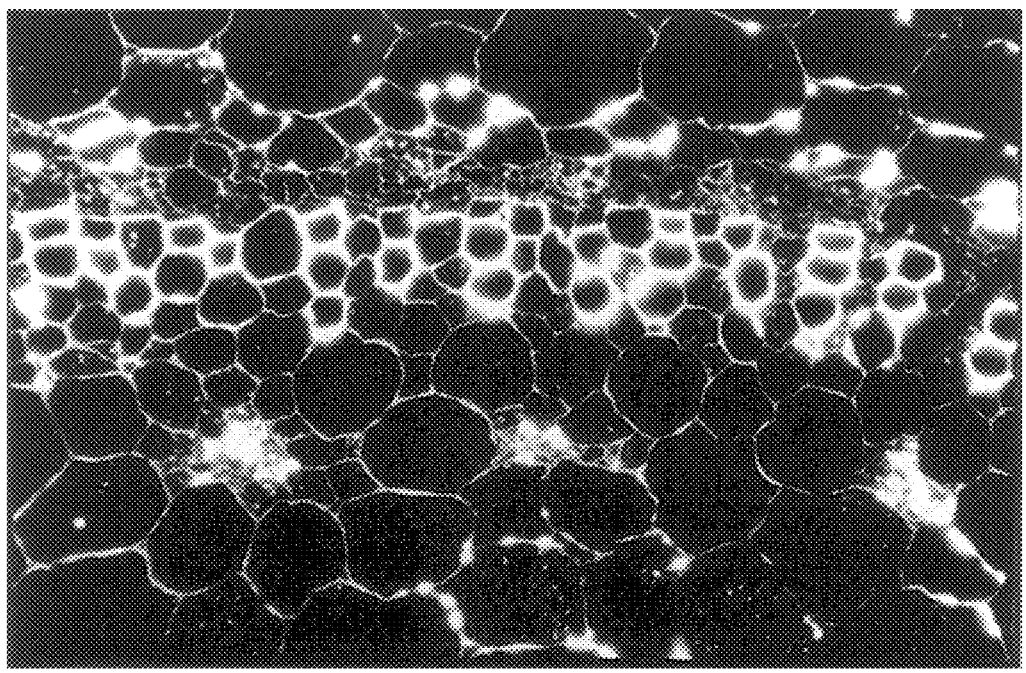
T
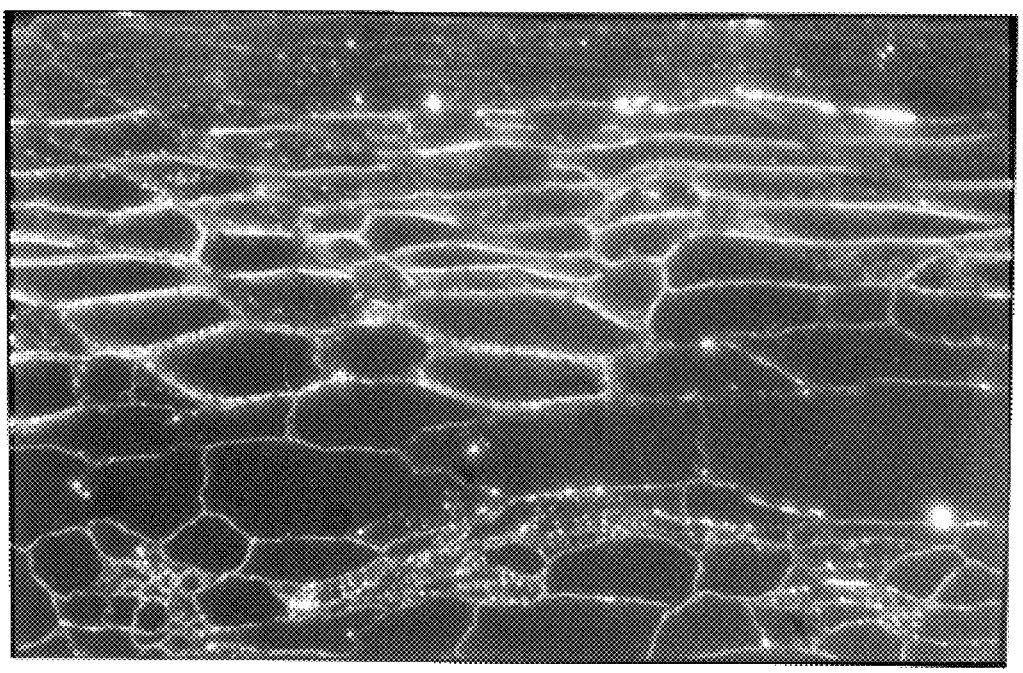
L
Fig. 9d

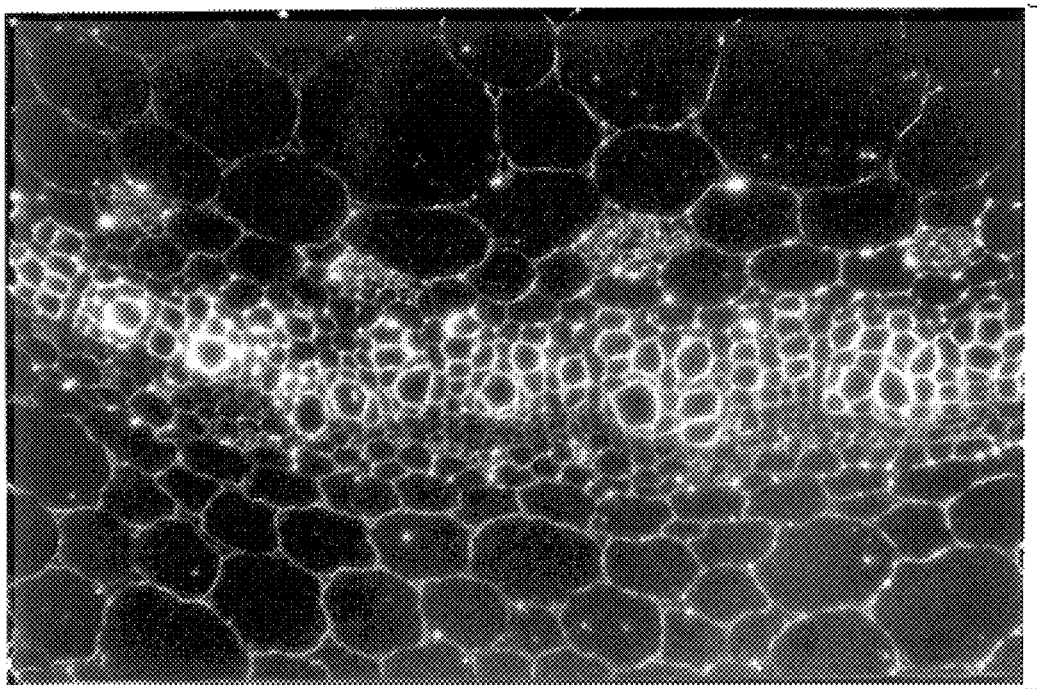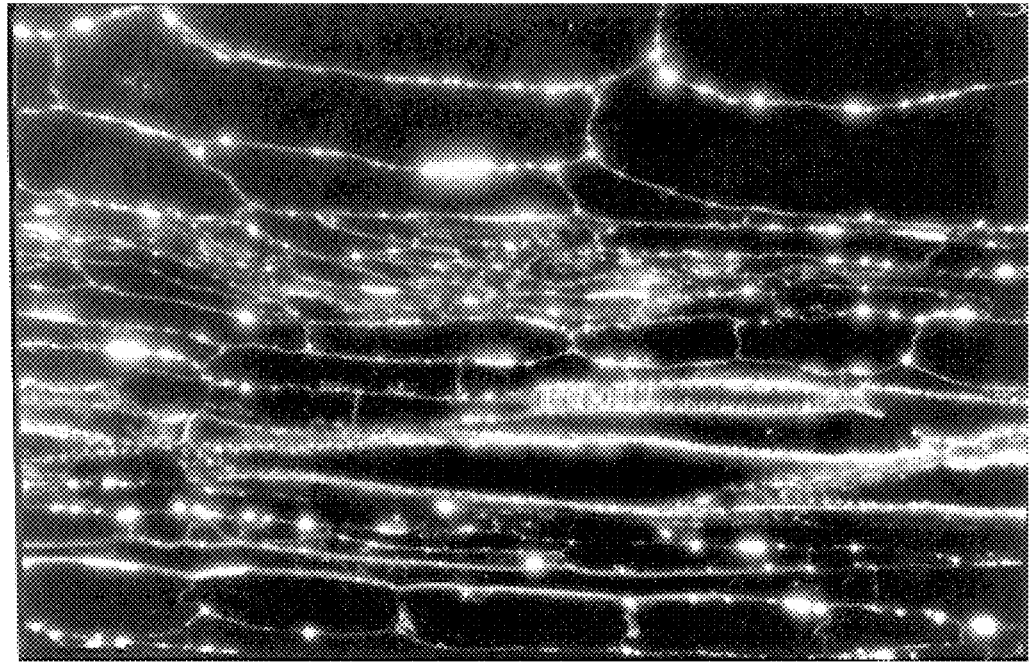
Fig. 9e

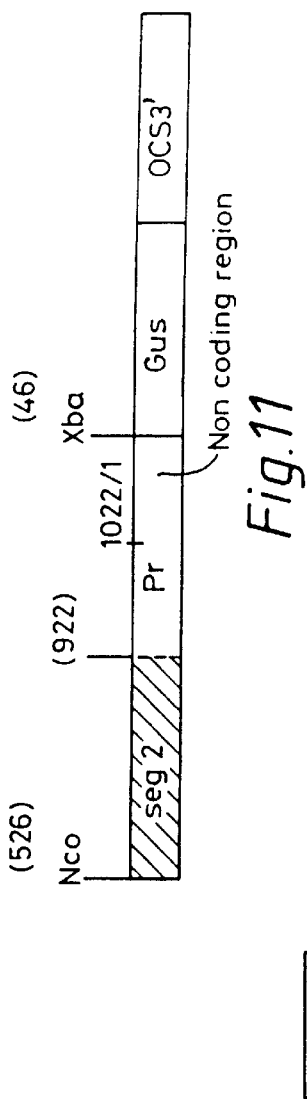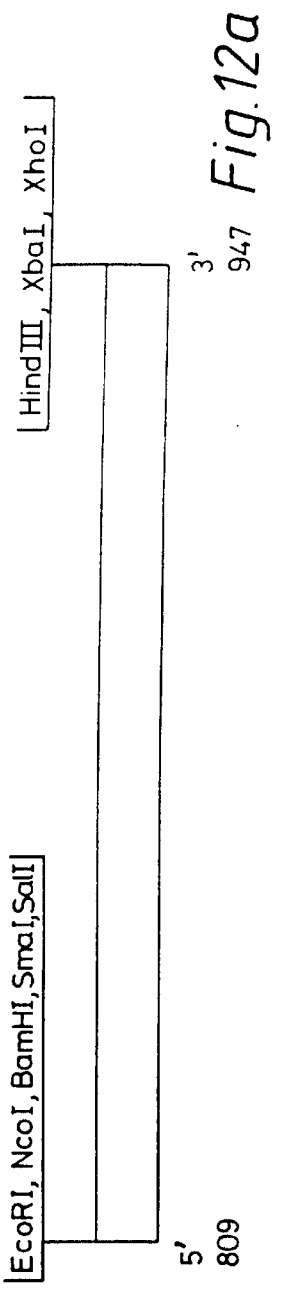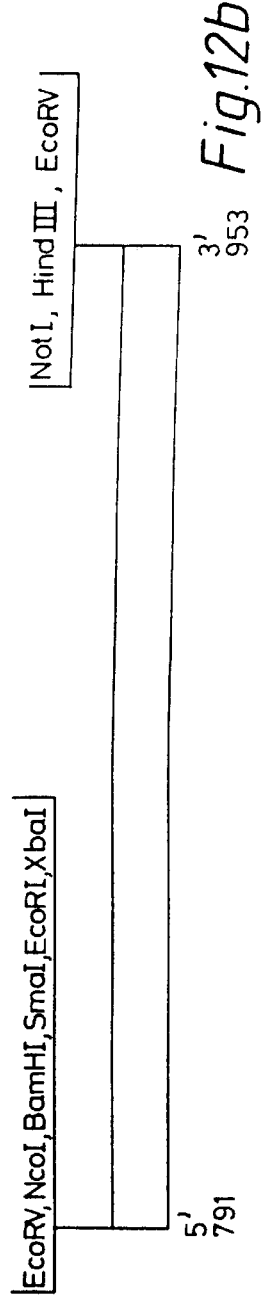

Stem

Leaf

Fig.13c  Stolon
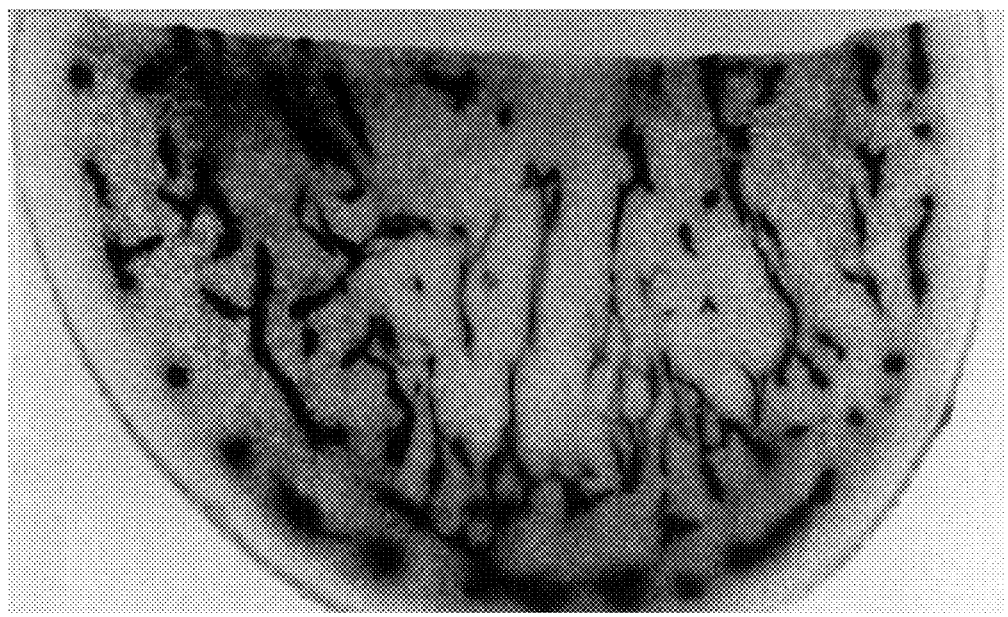
Fig.13d  Tuber

```
1     TAAGTTTAGC GGGGGAAAAA GGACAGTTGA
61    ATGTTGTCAG ATGCATGTTG TAATGCTTGT
121   TGATGATGGA AACTTAAAGC TTAATACTAC
181   GGTTCTTTGT TTATCAGGAA TGCTCATTGT
241   TATTGCCCTA AATCTGGTAC TTTATCCAAA
301   TCAAGAATGA TAAACTCGTA CACTCTCTAG
361   AACCGCTTAG GAAGGAACAT ATGTGATAAG
421   AGTCGGCCCA ATTCGAGAGG ACTAGTCTCC
481   TAAACAAAAC ACATATAAAA AACCTAAAAA
541   GTGGGAACAG TTACAAATCT GCAGTCTCAC
601   CAAGTTTTCG AATGTTCTCC CACCATTCAC
661   TAGCTGACAC AACCCGTTTT GACCCAACAT
721   AATCGACTTG TCCTCAAGTC GAAAGGAGGG
781   ATTGGAGGTT GATGGATGAT TTCCTTGTGT
841   GCTTTTAATG CCTCTTGAAC TGTAGCCACA
901   AATTC
```

Fig. 15a

| | | | |
|---|---|---|---|
| TCTGTTGCTG | TTTGCAATTT | TTTAAAGGGT | 60 |
| TCATCAACAC | ATTATATGAC | TTGCAGTTGC | 120 |
| TTTTGTTTAT | TCACTTACAA | ATACCGGTTG | 180 |
| ATGTAGCTAA | AAGCTGGCCG | TTTATAGTTT | 240 |
| AACTAAATTT | GGAAACATCA | AATACTTTTT | 300 |
| GGTACTCCTG | AAATTTAAAT | CAAAATCCAA | 360 |
| AACTGAAATT | TCGATTAACT | ATTACAAGAT | 420 |
| GATTACAAGG | AGTAAATATC | TTAATCTTGA | 480 |
| TATAGGAACA | TAATACATAA | ACTAAAAGTT | 540 |
| TCCCTAAATT | TGTGAGTCAC | CTTTCACCTA | 600 |
| TTTCCCTCCA | CCCGGATTCC | CTCCAATTAA | 660 |
| TGGGTTCGTA | TCAATACATC | CGGCCCGGAA | 720 |
| GAATTATTGT | GCCAAGCAAA | AAGCCATTCG | 780 |
| TTGAAAGCTT | CAAAAGATCC | GGCCAAATCA | 840 |
| ACACCACTTT | GAAACCTCAA | ATCTGTTTTG | 900 |
| | | | 905 |

Fig.15b

PLANT TRANSCRIPTION REGULATORS FROM CIRCOVIRUS

The present invention relates generally to a novel range of transcription regulators and transcription regulator-like sequences operable in plants. More particularly, the present invention is directed to transcription regulators and transcription regulator-like sequences of viral origin and, even more particularly, of nanovirus origin The transcription regulators and transcription regulator-like sequences of the instant invention are useful in genetic engineering of plants and in particular leguminous plants such as to facilitate or control expression of foreign genes. The transcription regulators and transcription regulator-like sequences of the present invention are also useful in facilitating different levels of expression in different plant tissue types.

Bibliographic details of the publications referred by author in this specification are collected at the end of the description. Sequence Identity Numbers (SEQ ID Nos.) for the nucleotide sequences referred to in the specification are defined following the bibliography.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Transcription regulators are molecules, and generally nucleotide-based molecules, which facilitate and modulate expression of genetic sequences at the level of transcription. Transcription regulators include promoters and termination and polyadenylation sequences amongst other effectors and facilitators of transcription.

Promoters are specific nucleotide sequences to which RNA polymerase binds to initiate RNA synthesis in cells. They contain the start site for RNA synthesis and the genetic signals to initiate polymerase mediated RNA synthesis. In addition, sequence specific DNA-binding proteins are presumed either to inhibit or to stimulate the initiation of RNA synthesis by binding next to the promoter and affecting the binding of the polymerase to the promoter. Terminator sequences refer to termination and polyadenylation sequences and are required for transcription of functional mRNAs. Termination sequences are located downstream (i.e. at the 3' end) of a gene and are recognized by RNA polymerase as a signal to stop synthesizing mRNA. Polyadenylation sequences are signals required for polyadenylation of eukaryotic mRNA molecules following transcription.

A viral promoter widely used to facilitate foreign gene expression in plants is the cauliflower mosaic virus (CaMV) 35S promoter (Odell et al, 1985), which is derived from a double-stranded DNA plant virus. The use of this promoter in plants and plant cells is well documented (Benfey and Chua, 1990; Higgins and Spencer, 1991). However, despite the apparent usefulness of this promoter, it is not functional in all plants and is particularly poorly operable in leguminous plants. There is a need, therefore, to identify other promoters, such as of viral origin, which are operable in plants and particularly leguminous plants. There is also a need to modulate levels of expression of genes and other genetic sequences within plant cells.

BRIEF DESCRIPTION OF THE INVENTION

Accordingly, one aspect of the present invention is directed to a genetic construct comprising a nanovirus promoter or promoter-like sequence and which is operable in a plant cell wherein said nanovirus comprises a multi-component DNA genome.

In a related aspect of the present invention, there is provided a genetic construct comprising a nanovirus promoter or promoter-like sequence and a termination and/or polyadenylation sequence, which sequences are operable in a plant cell.

A nanovirus is a non-geminated single stranded (ss) DNA plant virus (Table 1), distinct from caulimoviruses which have a double stranded genome, and geminiviruses, the only other known ssDNA plant viruses, which have geminated particles (Chu et al., 1994). As used herein, the nanovirus group is considered to include subterranean clover stunt virus (SCSV) (Chu and Helms, 1988), banana bunchy top virus (BBTV) (Thomas and Dietzgen, 1991; Harding etal. 1991; 1993; Bums etal. 1993) and milk-vetch dwarf virus (MDV) (Isogai et al. 1992; Sano et al. 1993) and faba bean necrotic yellows virus (FBNYV) (Katul et al., 1993).

In a particularly preferred embodiment, the nanovirus contemplated for use in accordance with the present invention comprises more than two DNA components or segments.

The present invention is particularly directed and hereinafter described with reference to subterranean clover stunt virus (hereinafter abbreviated to "SCSV") as a representative of the nanovirus group. This is done, however, with the understanding that reference to SCSV includes reference to all other suitable members of the nanovirus group to which the instant invention extends. Preferred members of the nanovirus group such as SCSV comprise more than two DNA components or segments. Reference hereinafter to "SCSV" also includes and extends to all naturally occurring or artificially induced mutants, derivatives, parts, fragments, homologues or analogues of the virus which still retain at least one suitable promoter and/or termination and/or polyadenylation sequences.

Accordingly, a particularly preferred embodiment of the present invention contemplates a genetic construct comprising an SCSV promoter or promoter-like sequence and which is operable in a plant cell.

A related aspect of the present invention is directed to a genetic construct comprising an SCSV romoter or promoter-like sequence and a termination and/or polyadenylation sequence, which sequences are operable in a plant cell.

The term "genetic construct" is used in its broadest sense to include any recombinant nucleic acid molecule such as an isolated nucleic acid molecule, vector, expression vector or binary vector. It may comprise solely the nanovirus promoter or may contain one or more promoters in association with regulatory and/or reporter sequences.

The genetic construct may be double or single stranded DNA, in linear or covalently closed circular form. As stated above, it may comprise only the promoter or promoter-like sequence or may carry other heterologous or homologous transcription regulator sequences and/or heterologous structural gene sequences including promoters associated with SCSV. By "homologous" is meant a gene sequence naturally associated with the SCSV promoter. "Heterologous" means a "foreign" gene relative to the promoter or a gene not otherwise normally associated with the SCSV promoter. In a preferred embodiment, the foreign gene is also foreign to SCSV. Examples of foreign genes include genes which facilitate resistance to insects or other pest infestation, enhance resistance to insecticides or herbicides, promote frost resistance, alter flower or petal colour, decrease the rate of senescence, especially in cut flowers, increase or enhance levels of certain proteins and/or ribozmes. More particularly, the foreign genes include:

a) a resistance gene against plant viruses, bacteria, fungi, nematode and other pathogens;

b) a plant virus resistance gene including a synthetic gene from and against alfalfa mosaic virus, subterranean clover stunt virus, subterranean clover mottle virus, subterranean clover red leaf virus, potato leafroll virus, tomato spotted wilt virus, bean yellow mosaic virus, white clover mosaic virus, clover yellow vein virus, potato viruses x, y, s, m and a, cucumber mosaic virus, rice ragged stunt virus and barley yellow dwarf virus;

c) a gene to improve nutritional value of plants such as sunflower high sulphur gene SF8;

d) a bloat resistance gene;

e) an antibody gene;

f) a cereal thionin and ribosome inactivating protein gene;

g) an insect resistance gene including BT toxin gene and proteinase inhibitor gene from *Nicotiana alata*;

h) a selectable marker gene such as those conferring resistance to kanamycin, phosphinothricin, spectinomycin and hygromycin;

i) a reporter gene such as GUS, CAT and pigment genes;

j) a gene encoding a regulatory protein which modulates expression of a gene in plant cells.

The present invention furter contemplates a genetic construct comprising two heterologous genes operably linked to the same or different nanovirus promoters operable in a plant cell. Preferaby the promoter or different promoters are from a nanovirus with a genome comprising more than two components or segments. Most preferably the promoter or different promoters are from SCSV and in particular are selected from segments 1 to 7 of SCSV as defined by SEQ ID NOs. 1 to 7. (See below).

The genetic constructs may also comprise a termination or polyadenylation sequence operably linked to one or both of the heterologous genes. In one embodiment, the termination and/or polyadenylation sequence is the same for each gene. In an alternative embodiment the termination and/or polyadenylation sequence is different for each gene. Most preferably the termination and polyadenylation sequence is selected from segments 1 to 7 of SCSV as defined by SEQ ID NOs. 1 to 7 (See below). In yet another embodiment at least one termination and polyadenylation sequence is from the MeA 3 gene of *Flaveria bidentis* (see below).

The term "transcription regulator" is used in its broadest sense to include promoters, termination and polyadenylation sequences and other effectors and facilitators of transcription of genetic sequences. As with promoters contemplated by the present inveniton, the termination and polyadenylation sequences may be of SCSV origin and may be naturally associated with a corresponding promoter from SCSV or may be associated with another promoter of SCSV. Alternatively, the termination and/or polyadenylation sequences may be derived from non-SCSV sources. A particularly preferred terminator comprises the 3' nucleotide sequence of the MeA3 gene of *Flaveria bidentis* which codes for an NADP-malic enzyme of C4 photosynthesis (Hatchi, 1987). The nucleotide sequence of the terminator region of the MeA gene is shown in FIG. 15. The combination of an SCSV promoter with, for example, the *F. bidentis* MeA gene terminator sequence results in a high level of expression especially in monocotyledonas plants relative to constructs without the terminator sequence.

The foreign gene may also be in the antisense orientation so as to facilitate reduced levels of endogenous plant gene products. In this regard, "gene" may be ten base pairs in length, tens of base pairs in length, hundreds of base pairs in length or a fill length or near full length gene but in a reverse orientation relative the promoter. The foreign gene may also be placed in the "isense" orientation for co-suppression of a target gene.

According to another aspect of the present invention, there is provided a genetic construct comprising an SCSV promoter or promoter-like sequence operable in a plant cell and at least one restriction endonuclease site downstream of said promoter to facilitate insertion of a heterologous gene such that said gene is operably linked to said promoter. In an alternative embodiment, the genetic construct comprises an SCSV promoter or promoter-like sequence operable in a plant cell and a heterologous gene operably linked to said promoter. In both embodiments, the term "gene" includes those directing the synthesis of oligonucleotides such as those useful in antisense techniques as well as ribozymes.

In still a further embodiment of the present invention, there is contemplated a genetic construct comprising an SCSV promoter or promoter-like sequence operable in a plant cell and at least one restriction endonuclease site downstream of said promoter to facilitate insertion of a heterologous gene such that said gene is operably linked to said promoter and a termination and/or polyadenylation sequence positioned such that same sequence is at the 3' end relative to said heterologous gene to facilitate expression of said heterologous gene. Preferably, the termination sequence is from SCSV. Alternatively, the terminator sequence is from the *F. bidentis* MeA3 gene.

Plants contemplated by the present invention include both monocotyledonous and dicotyledonous species. The present invention also extends to leguminous and non-leguminous plants although leguminous plants are preferred.

The SCSV genome comprises at least seven distinct circular ssDNA components described as segments 1–7. The size of these segments range from about 988 to about 1022 nucleotides. Each of the seven DNA components of SCSV contains one major open reading frame of the viral sense and a non-coding region of various lengths containing a conserved potential stem and loop structure (FIGS. 1 and 2; Table 2). Each trnscription unit contains a typical TATA box and a polyadenylation signal for start and end of transcription, respectively (Table 2).

Because the DNAs are circular, the sequences in the non-coding regions comprise the promoters and the terminator signals which vary with different DNA components (Table 2). The TATA boxes and the stem-loops of the two replicase-associated protein genes in segments 2 and 6 are quite different from those of the other genes. In contrast, the stem-loops and TATA boxes are the same in segments 1, 3, 4, 5 and 7. All the DNAs, except those of segments 2 and 6, also share a common sequence (known as the common region) in the non-coding region (FIGS. 1 and 2).

The present invention, therefore, extends to each of the seven promoters and to termination and polyadenylation sequences on segments 1–7 of SCSV. The nucleotide sequences of segments 1–7 are shown in FIG. 6 and are defined in SEQ ID NOs. 1–7, respectively.

Segment 5 was identified as the coat protein gene based on N-terminal amino acid sequence and amino acid composition data (Chu et al., 1993a). Segments 2 and 6 encode proteins containing the characteristic NTP-binding motifs and thus are predicted to be the putative viral replication-associated protein (RAP) genes. The remaining 4 DNA components are unrelated to each other or to segment 2, 5 and 6, based on their distinctive deduced amino acid sequence. The SCSV DNAs have no significant nucleotide sequence homology with the genomes of geminiviruses although some homology exists at the deduced amino acid level.

The replicative competency of SCSV has been demonstrated (Chu et al., 1993b). Since the SCSV virion DNA is single-stranded and the transcripts are of viral sense, the first likely biosynthetic event after uncoating is likely to be the synthesis of the replicative form DNA using host DNA polymerase. (The DNAs of SCSV have the ability to self prime in dsDNA synthesis [Chu and Helms, 1988]). Host RNA polymerase is thought to bind to the promoters initiating RNA transcription followed by synthesis of the viral proteins required for virus multiplication.

In a particularly preferred embodiment of the present invention, there is contemplated an SCSV promoter or promoter-like sequence comprising a nucleotide sequence selected from within SEQ ID NO: 1, SEQ ID NO: 2, SEQ ID NO: 3, SEQ ID NO: 4, SEQ ID NO: 5, SEQ ID NO: 6 and SEQ ID NO: 7 and/or genetic constructs comprising same.

A "promoter-like sequence" as used herein includes any finctional mutant, derivative, part, fragment, homologue or analogue of a naturally occurring SCSV promoter. Promoter-like sequences contemplated herein include single or multiple nucleotide substitutions, deletions and/or additions to an SCSV promoter, provided that the said promoter-like sequences retain at least 35%, preferably at least 45%, more preferably at least 55%, even more preferably at least 65–70% and still more preferably at least 85–95% or greater promoter activity compared with the corresponding wild-type SCSV promoter.

In yet another embodiment, there is provided a genetic construct comprising an SCSV promoter or promoter-like sequence and which is operable in a plant cell, said promoter or promoter-like sequence corresponding to all or part of any one of SEQ ID NO: 1 to 7 or capable of hybridising under a range of stringency conditions, ranging from high to low stringency conditions to at least one of SEQ ID NO: 1 to 7. Conveniently, a mutant, derivative, part, fragment, homologue or analogue of an SCSV promoter is defined as being functional in a plant cell and capable of hybridising under a range of at least high to low stringency conditions to at least one of SEQ ID NO: 1 to 7.

In a particularly preferred embodiment, the genetic construct further comprises a termination and/or polyadenylation sequence from SCSV or from non-SCSV source and which enhances or other facilitates expression of a gene operably linked to said promoter.

For the purposes of defming the level of stringency, reference can conveniently be made to Sambrook et al (1989) which is herein incorporated by reference where the washing steps at pages 9.52–9.57 are considered high stringency. A low stringency is defined herein as being in 0.1–0.5% w/v SDS at 37–45° C. for 2–3 hours. Depending on the source and concentration of nucleic acid involved in the hybridisation, alternative conditions of stringency may be employed such as medium stringent conditions which are considered herein to be 0.25–0.5% w/v SDS at $\geq 45°$ C. for 2–3 hours or high stringent conditions as disclosed by Sambrook et al (1989).

Another embodiment of the present invention contemplates a method of expressing a foreign gene in a plant cell, said method comprising introducing into said plant cell a genetic construct comprising and SCSV promoter or promoter-like sequence operable in said plant cell and operably linked to said foreign gene. In a further embodiment, multiple SCSV promoters are used to drive one or more transgenes without antagonism. In yet a further embodiment, the SCSV promoter is associated with the SCSV segment 2 gene in order to enhance the expression of the foreign gene. In another embodiment, the genetic constructs further comprises one or more termination and/or polyadenylation sequences which are located at the 3' end of the foreign gene. These sequences enhance or otherwise facilitate expression of the foreign gene. The termination and/or polyadenylation segment may be from SCSV or from another source such as the *F. bidentis* MeA gene.

In still yet another embodiment, the present invention contemplates a transgenic plant carrying an SCSV promoter or promoter-like sequence as hereinbefore defined in its genome and optionally a termination and/or polyadenylation sequence to enhance expression of a gene downstream of said promoter. Preferably, the transgenic plant exhibits altered characteristics due to expression of a genetic sequence such as a gene, oligonucleotide or ribozyme downstream of the SCSV promoter.

DETAILED DESCRIPTION OF THE INVENTION

The present invention is further described by reference to the following non-limiting figures and/or examples. Reference herein to a promoter region from SCSV is abbreviated to "S" for SCSV, the genome segment number (e.g. 1, 3, 4, 5 and 7) and "nc" for non-coding region. For example, the promoter from SCSV genome segment 1 is defined as "S1nc". Terminator sequences for particular SCSV genome segments are indicated for example, as follows: "SC1Tr" or "SC5Tr" for the terminator sequences for segments 1 and 5, respectively. Genetic constructs comprising an SCSV promoter, a reporter gene such as GUS and a terminator sequence such as from SCSV is abbreviated to "SCSV-:GUS:SCTr" or "SCSV:GUS:SCSVTr". Specific promoters and termination sequences are defined as above, for example S4nc:GUS:SC1Tr or S4nc:GUS:Me3", "S4nc:GUS:Me3". In the latter construct the terminator sequence from the MeA gene of *Flaveria bidentis* is used, referred to herein as "Me3".

Figure 3:
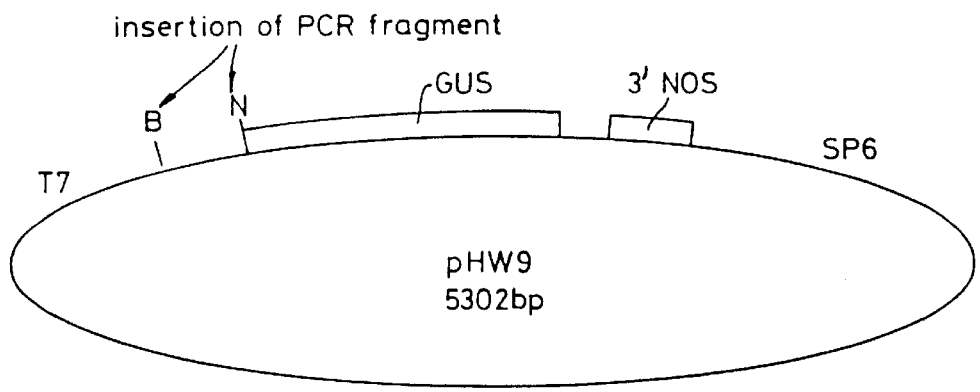

FIG. 3 is a schematic representation showing the construction of the seven SCSV DNA non-coding region: β-glucuronidase (GUS) fusion expression vectors for transformation into tobacco plants. The amplified PCR fragments were separately cloned in front of the GUS gene in pHW9 at the BamnHI (B) and NcoI (N) sites as indicated. The resultant recombinant pHW9 vectors were cut at the EcoRI site and cloned into the EcoRI site of the recipient PGA470 binary vector.

FIG. 4 is a schematic representation showing the construction of the segments 5 and 7 promoter:GUS fusion expression vectors and their deletion derivatives for protoplast studies. DNAs corresponding to the fill-length non-coding regions were obtained by PCR and cloned into pKGO in front of GUS by blunt end ligation at the Sal/I site as indicated. The deletion derivatives were obtained by digesting the pKGO clones containing the full-length sequence with HindIII or PstI on the vector and the appropriate restriction enzymes on the SCSV sequence as indicated. The deleted pKGO constructs were religated after end-filling as required.

Figure 5:
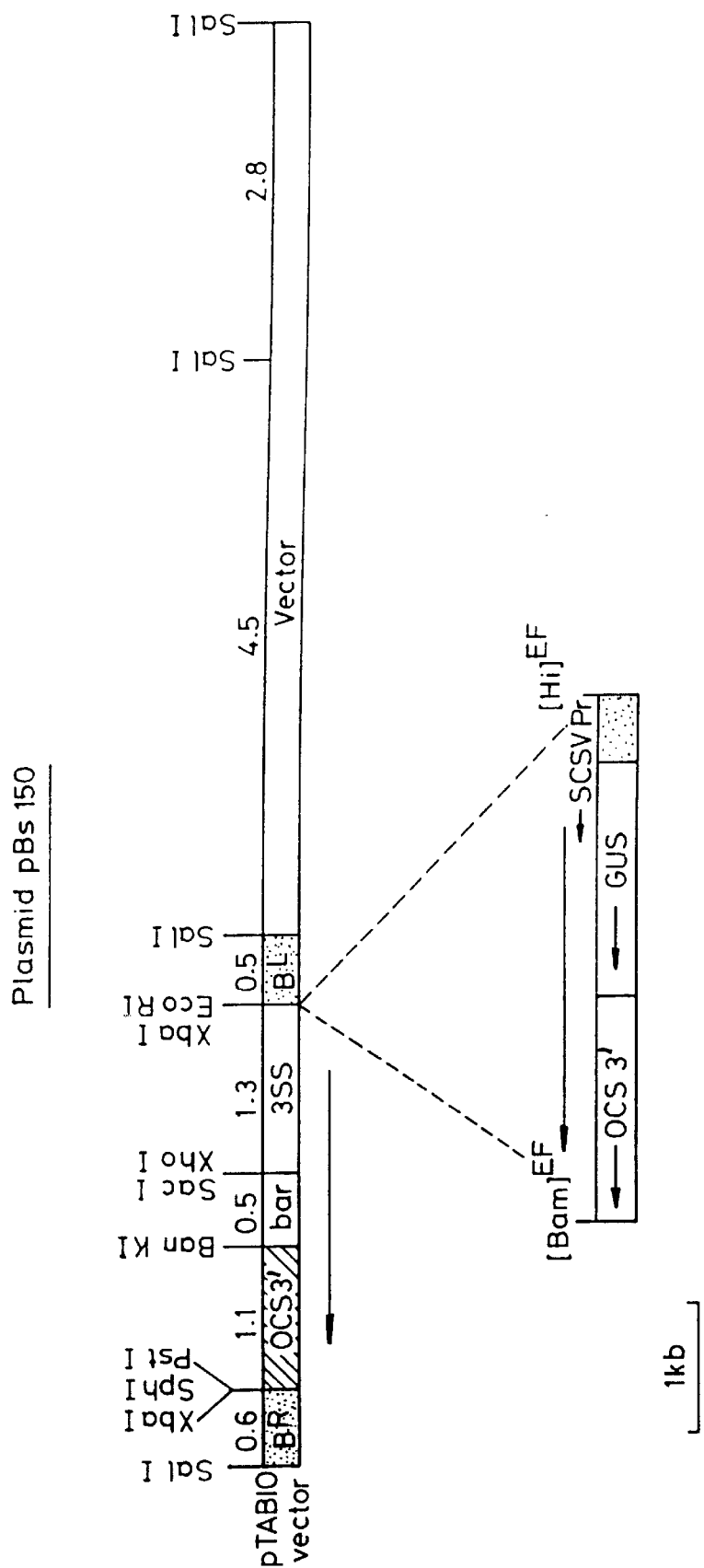

FIG. 5 is a schematic representation showing the construction of the recombinant binary pTAB10 vector (pBS150) containing the seg 7 promoter(57nc):GUS fusion gene for transformation into subterranean clover plants. The 57nc:GUS expression cassette was excised.

FIG. 5 is a schematic representation showing the construction of the recombinant binary pTAB10 vector (pBS150) containing the seg 7 promoter(57nc):GUS fusion gene for transformation into subterranean clover plants. The 57nc:GUSexpression cassette was excised from the pKGO construct (FIG. 4) by digestion with HindIII and BamHI and blunt-end ligated to pTAB10 at the EcoRI site after end-filling the DNAs.

FIGS. 6($i$)–6($xiv$) show the complete nucleotide sequences of the seven SCSV DNA circles (SEQ ID NOS:1 to 7). The arrows underlying the sequence indicate the positions at which amplification primers (Table 8) anneal to the circular SCSV DNA, including the direction of amplification, thereby amplifying a single fragment containing a promoter and terminator/polyadenylation signal for the construction of expression cassettes.

FIG. 7 is a copy of a photographic representation showing GUS expression detected by histochemical staining on leaves of transgenic tobacco and subterranean clover transformed with the SCSV seg 7 promoter(S7nc):GUS fusion expression cassette.

Figure 8A:
Figure 8D:
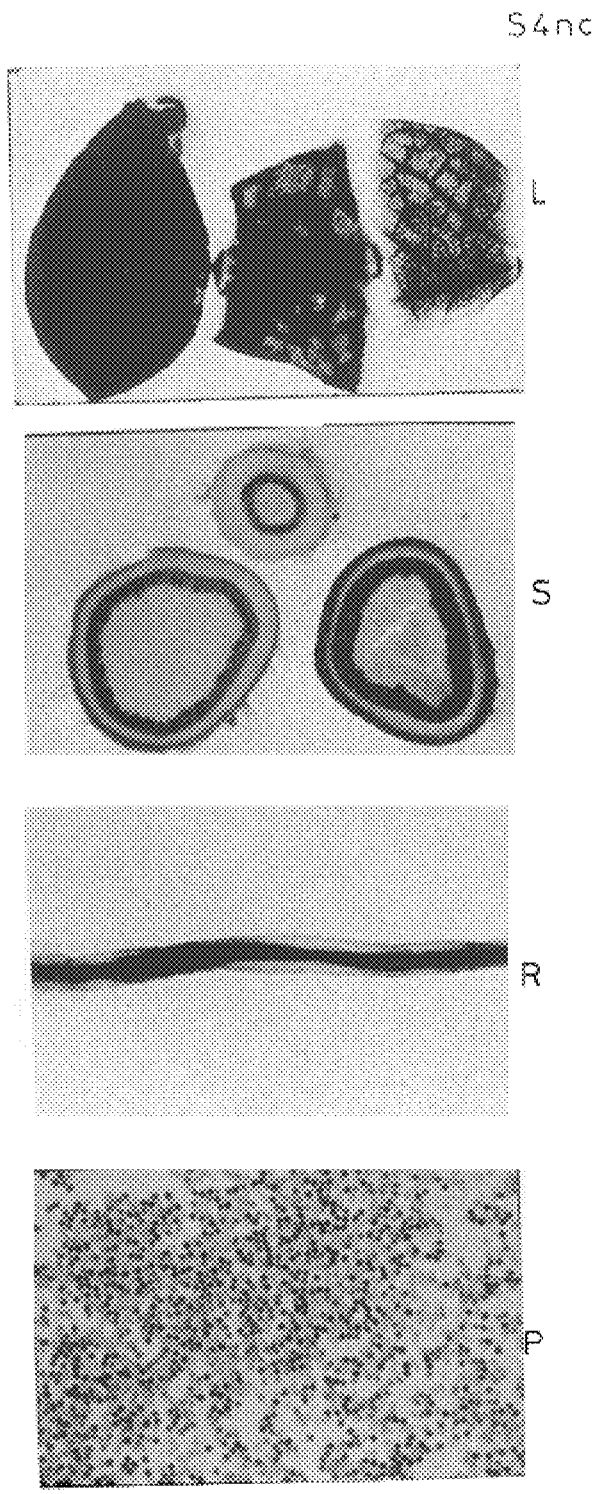

FIGS. 8A to 8F are photographic representations of histochemical staining for GUS activity in transgenic plants—bright field. Bright field exposures of stained leaf pieces (L), stem sections (S), roots (R) and pollen (P) from tobacco plants transformed with the GUS fusion constructs containing the SCSV promoter regions from segments 1, 3, 4, 5 and 7 referred to as S1nc, S3nc, S4nc, S5nc and S7nc promoter regions and from non-transformed plants (NT). Blue colouration indicates GUS expression. Each leaf, stem or root piece represents an independent transformant (except the top two root pieces of S5nc which could not be separated easily) and the pollen samples were mixtures from two or more transformants. FIG. 8a shows differential expression of GUS in plants transformed with either S4nc or S5nc regions compared to a non-transformed plant (NT).

FIGS. 9A to 9E are photographic representations showing histochemical staining for GUS activity in transgenic plants—dark field. Transverse (T) and longitudinal(L) thin sections of stained, embedded stem pieces from tobacco plants transformed with the GUS fusion constructs containing the component 1 (S1nc), 3 (S3nc), 4 (S4nc), 5 (S5nc), and 7 (S7nc) promoter regions, viewed with a dark field. Pink crystals indicate GUS expression. The stem pieces used.

Figure 10:
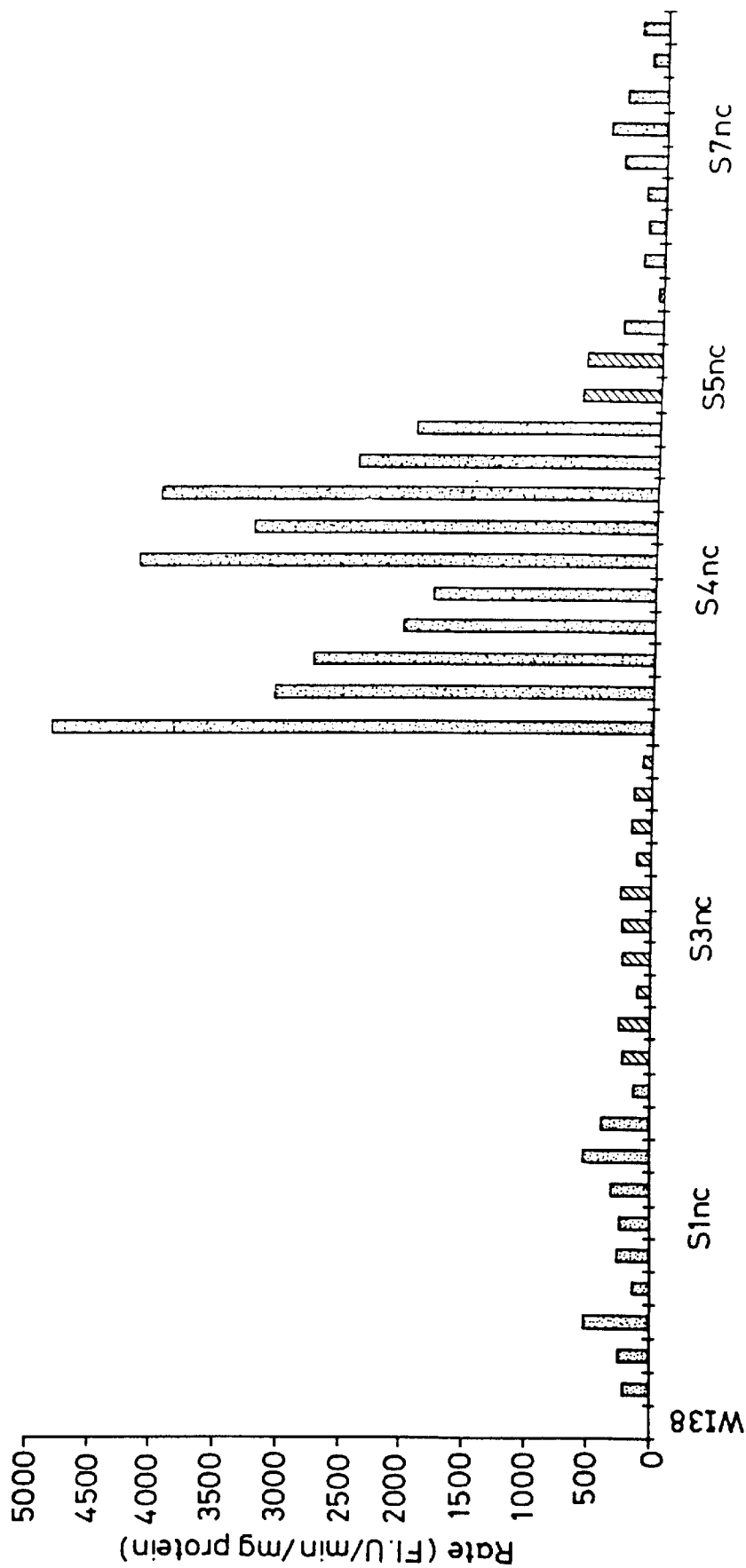
Figure 13A:
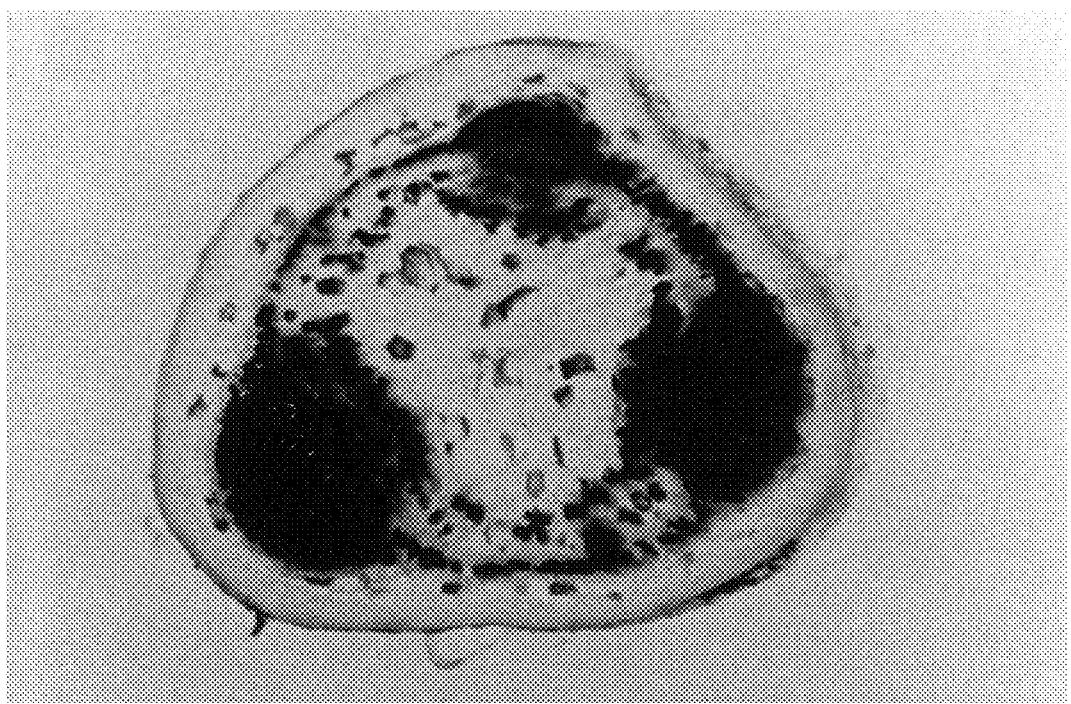
Figure 13B:
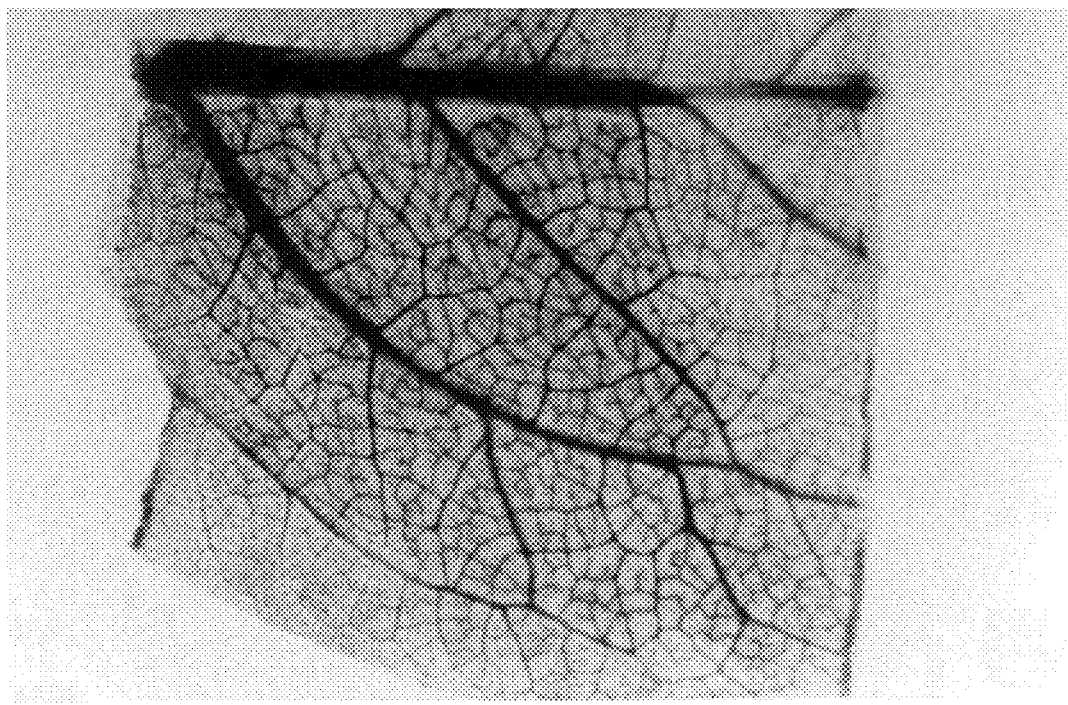

FIG. 10 is a graphical representation of a fluorometric assay for GUS expression. Fluorometric assay results from leaf extracts of tobacco plants transformed with the GUS fusion constructs containing the component 1 (S1nc), 3 (S3nc), 4, (S4nc), 5 (S5nc), and 7 (S7nc) promoter regions. Each column represents an independent transformant. GUS activities were measured with a Labsystems Fluoroskan at 5 or 10 minute intervals over 60 minutes (or 30 minutes for S4nc) using 4-methylumbelliferyl β-D-glucuronide (MUG) as the substrate. The rates of GUS activity are expressed as fluorometric units (Fl.U.) per minute per mg of protein. 1000 Fl.U is approximately equal to 825 pmoles of 4-methylumbelliferone (MU).

FIG. 11 is a is a schematic representation showing the SCSV segment 2 promoter (S2nc) construct. A franent of segment 2 DNA from NcoI-XbaI was fuised to the promoterless GUS vector, pKGO. Pr, promoter; seg 2, segment 2 of SCSV.

FIGS. 12$a$ and 12$b$ are schematic representations showing constructs of SCSV:GUS:SCSV Tr expression vectors. The termination/polyadenylation sequences for segment 3 of SCSV (SC3Tr) and segment 5 (SC5Tr) were amnplified by PCR and cut with the respective restriction enzymes and then cloned into recombinant pKGO vector as indicated. The SC3Tr construct was cloned as an EcoRI-XhoI fragment into the pKGo vector containing S1nc:GUS:OCS3' to make S1nc:GUS:SC3Tr. The SSC5TR construct was made as an EcoRV fiagment into Vector pKGO containing S4nc:Gus:OCS3' to make S4nc:GUS:S5Tr.

FIGS. 13A to 13D are photographic representations showing GUS expression in potato plant tissues directed by the SCSV segment 4 promoter (S4nc). A. stem; B, leaf, C. stolon; and D. tuber.

Figure 14:
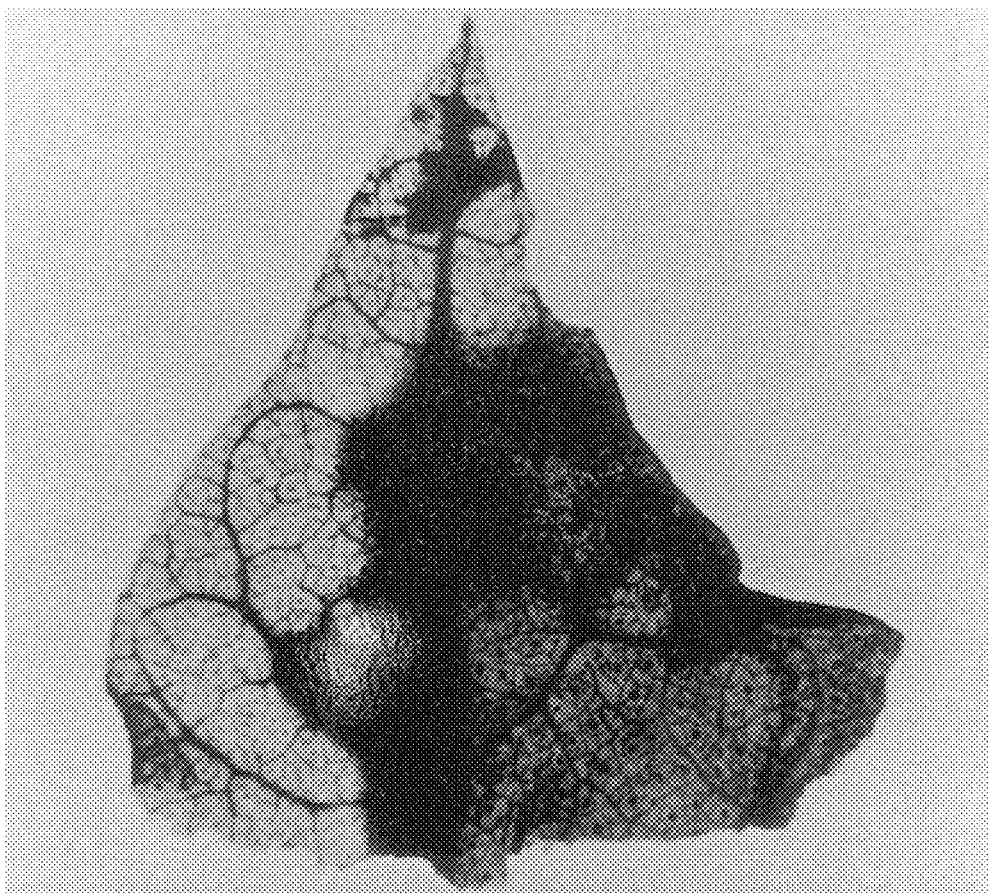

FIG. 14 is a photographic representation of GUS expression in cotton leaf directed by the SCSV segment 7 promoter (S7nc).

FIGS. 15(a)–15(b) show the nucelotide sequence of the MeA3's terminator sequence of the *Flaveria bidentis* MeA gene (Me3) set forth in SEQ ID NO: 8. The stop codon is located at the beginning of the sequence. This sequence was engineered in the Chimeric construct to include an EcoR1 site: GAATTCGTTTAG. . . . The chimeric constructs thus contained a sequence begining AATTCGTTTAG.

Figure 16:
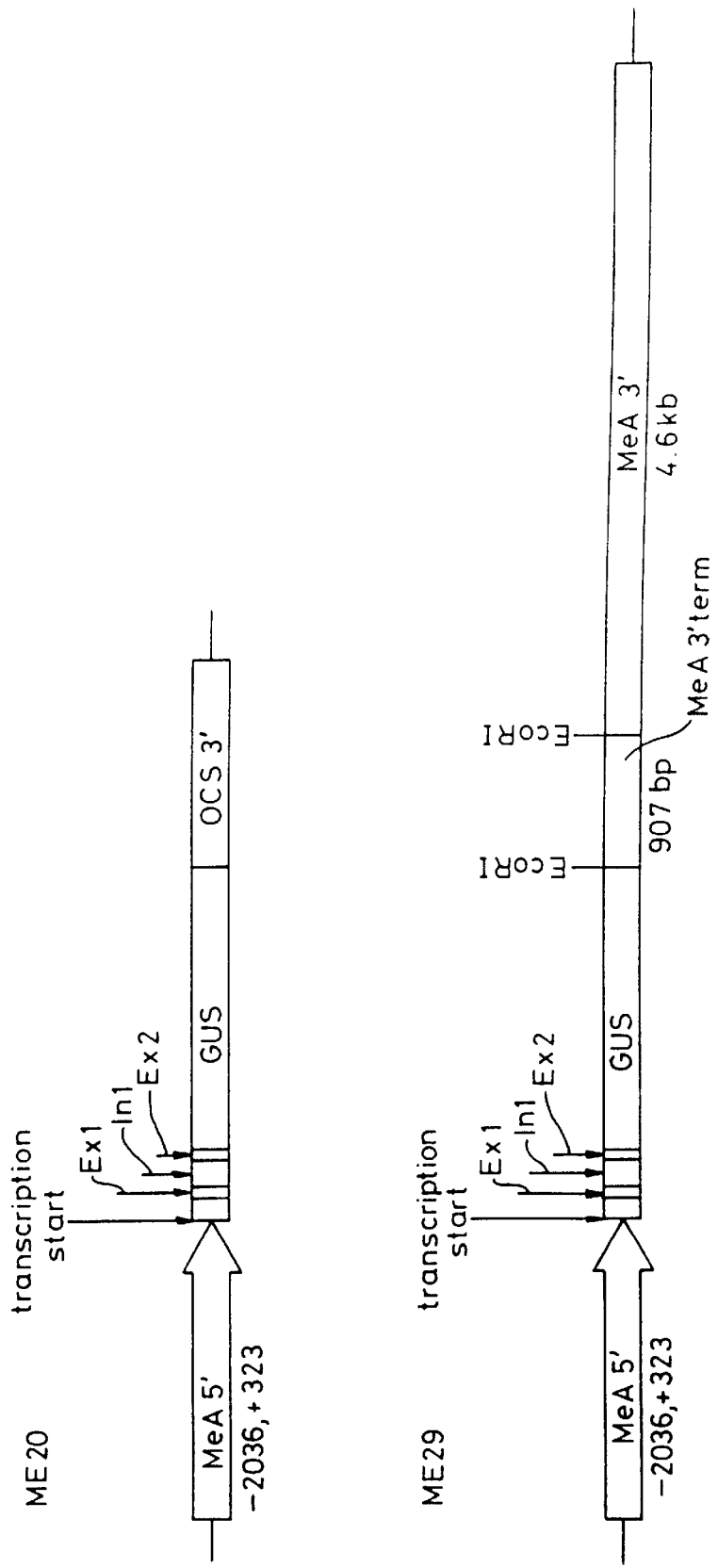

FIG. 16 is a diagramatic representation of GUS expression vectors (ME20 and ME29) containing the indicated *Flaveria bidentis* MeA gene regulatory elements.

Figure 17:
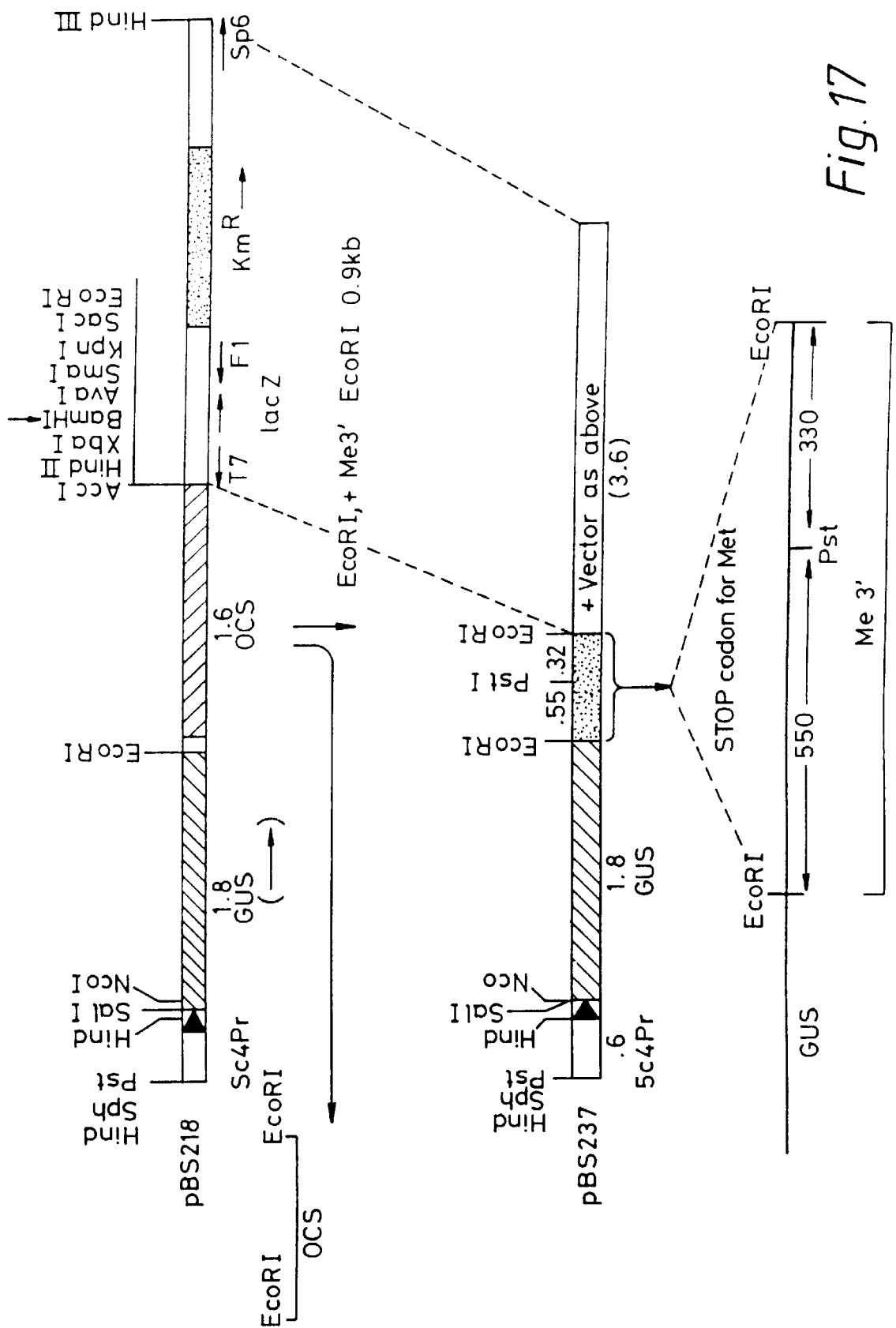

FIG. 17 is a diagramatic representation of the construction of S4nc plasmid pBS237 containing the expression cassette S4nc:GUS:Me3'. Plasinid pBS218 was digested with EcoR1 to remove OCS3' region and ligated with an EcoR1.

Figure 18:
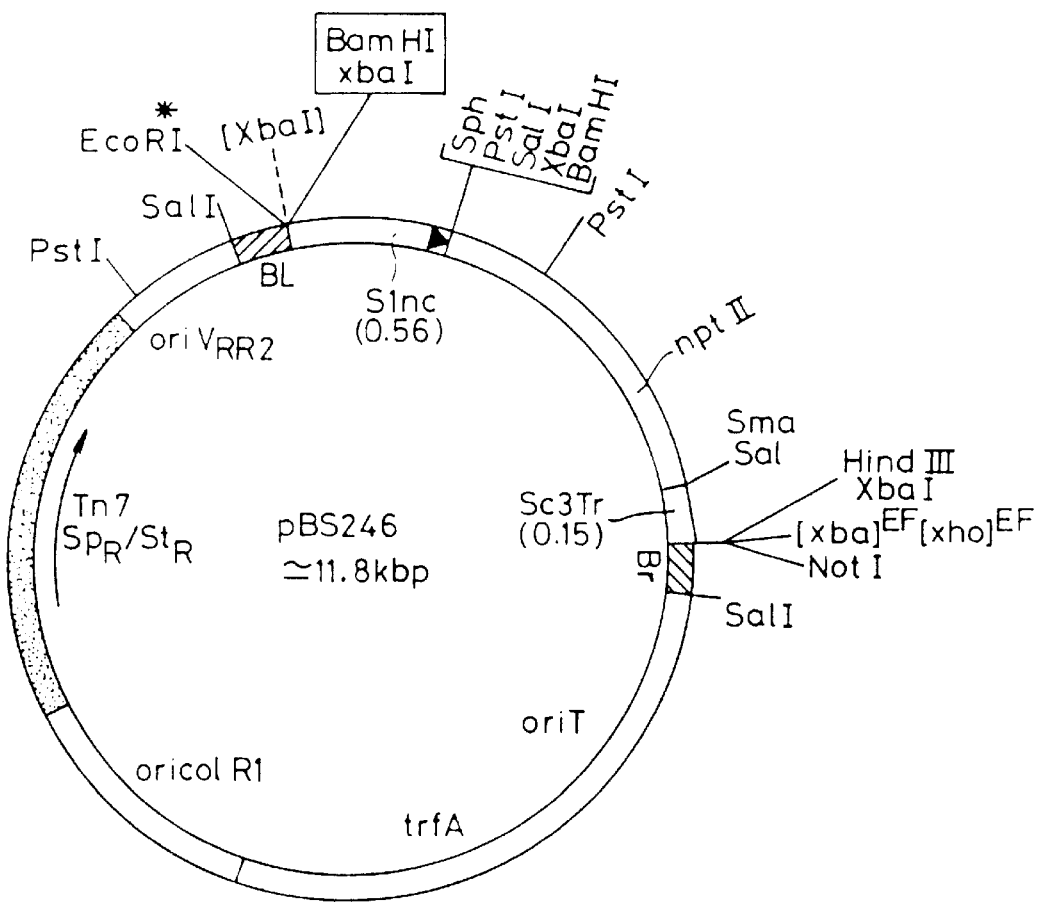

FIG. 18 is a diagramatic representation of the construction of plasmid pBS246 containing the S1nc:nptII:SC3Tr expression cassette. The SalI-SalI fragment is approximately 8.5–9 khp; B$_L$ is about 0.5 kbp; B$_R$ is about 0.6 khp. SC1nc:nptII:SC3Tr is about 1.7 khp.

Figure 19A:
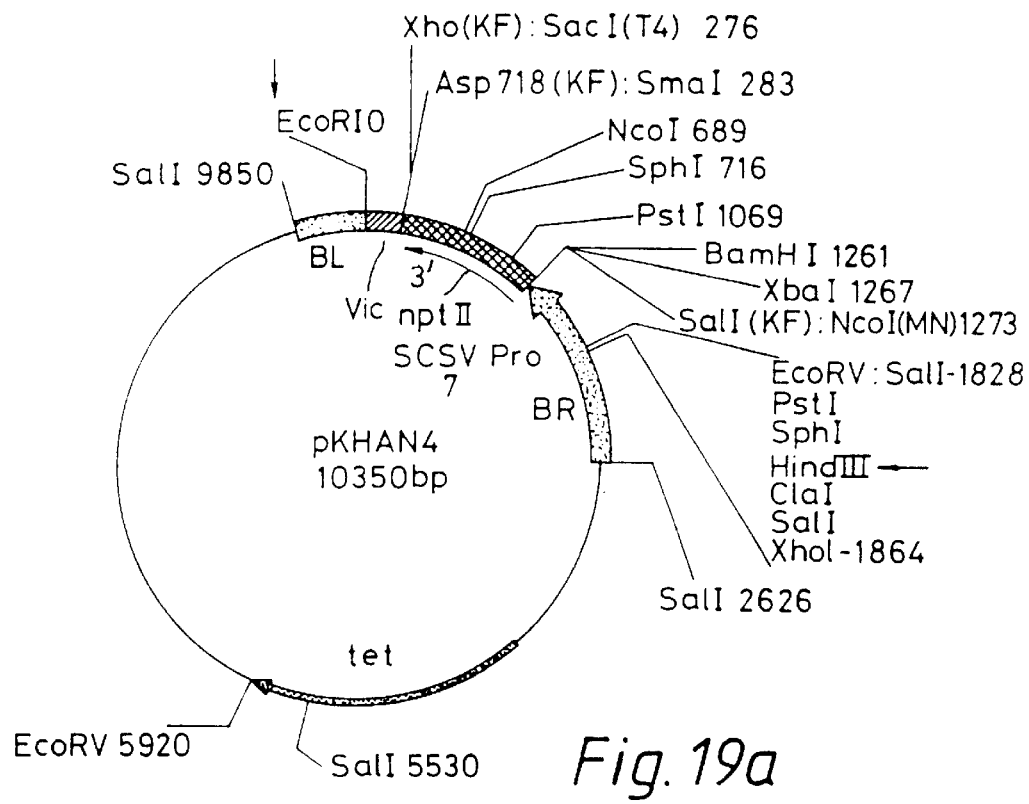
Figure 19B:
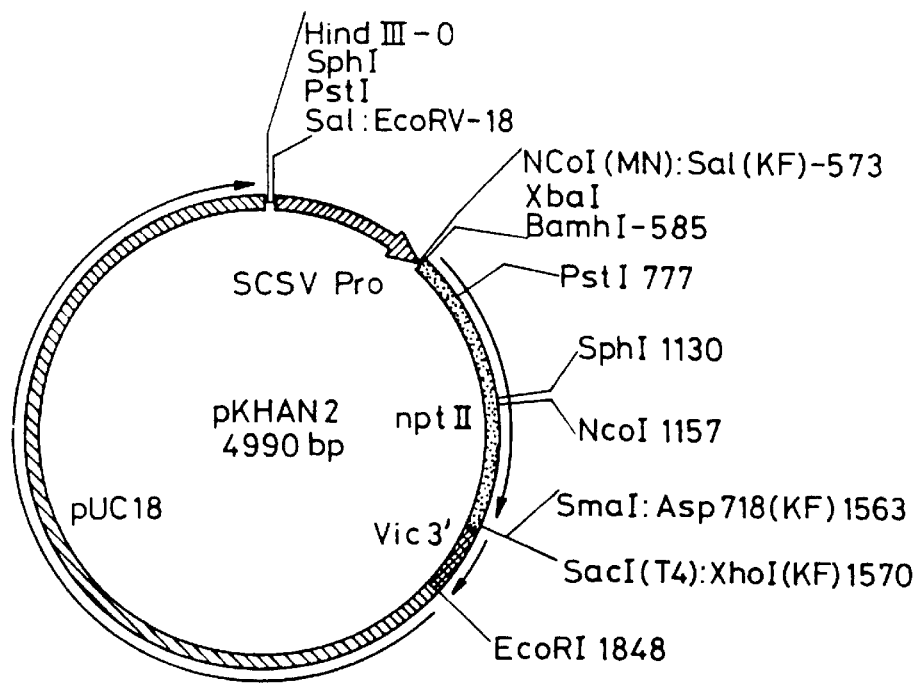
Figure 19C:
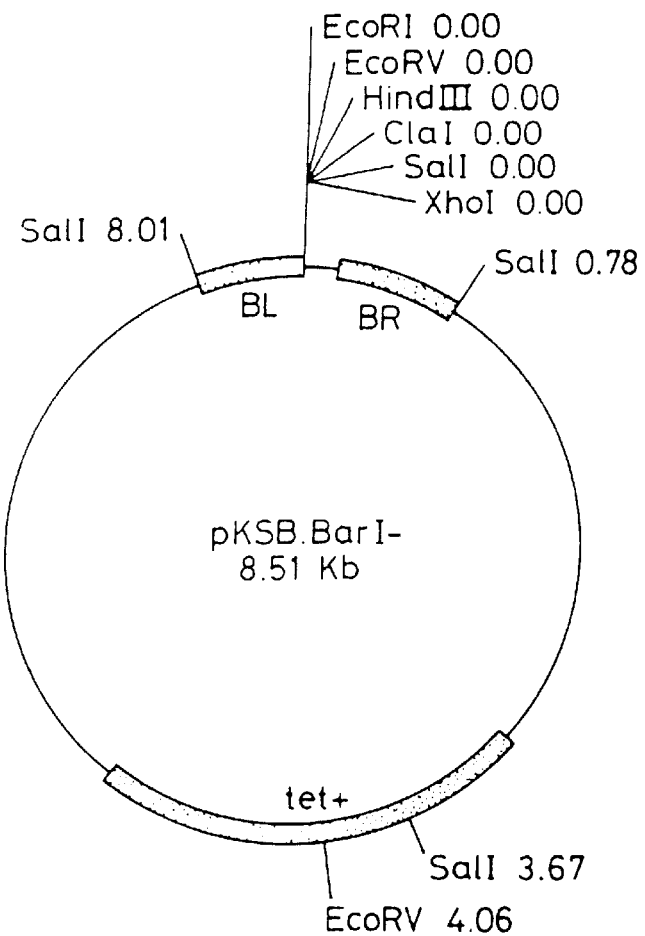

FIG. 19$a$–$c$ are diagramatic representations of the construction of plasmid pKHAN4 from pKHAN2 and pKSB-.bar1. pKHAN4: A HindIII-EcoR1 segment containing S7nc (572 bp), nptII coding region (978 bp) and vicillin 3' end (276bp) from pKHAN2 was inserted into binary plasmid pKSB.bar1 to yield pKHAN4; pKHAN2. The nptII coding region (978bp, BamHI-Sma1 fragment) from p35SKN was cloned into Asp718 site (blunted with klenow fragment) of pKHAN1 to create pKHAN 2. SCSV Pro=S7nc; pKSB. Bar 1: pTAB10.MCSori1B digested with EcoR1 as ligated together.

Figure 20:
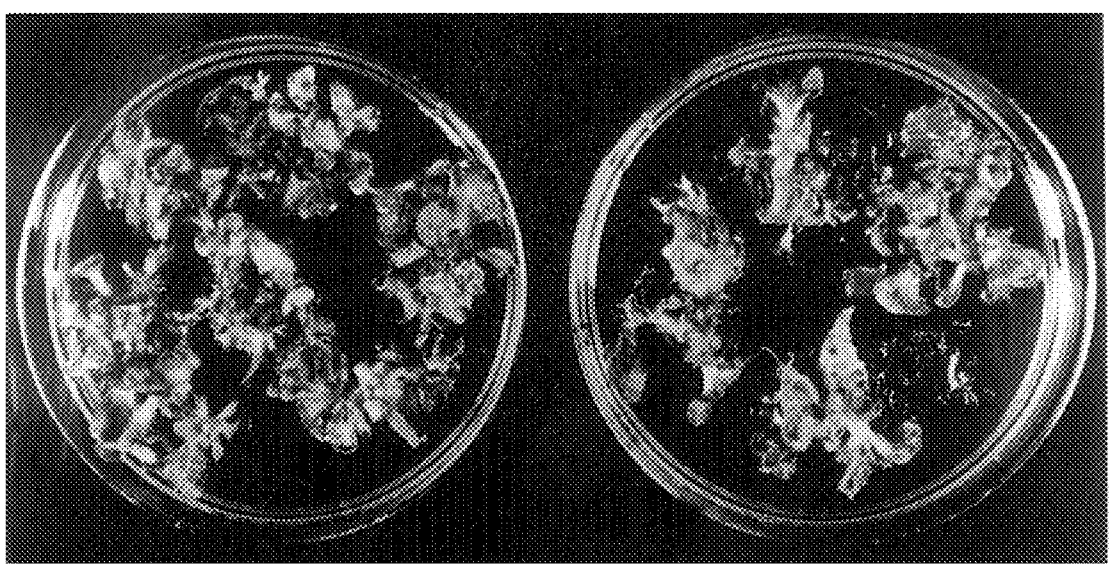

FIG. 20 is a photographic representation of a selection of Kananmycin resistant tobacco plants on regeneration medium transformed with binary vectors containing either 35S promoter:NPTII:35S terminator sequence (35SPrm:NPTII:35STrm) or S1nc:NPTII:SC3Tr expression cassette. (In the Figures, the abbreviations are 35S Prm NPTII35STrm and SC1 Prm NPTII Sc3 Trm, respectively.

Figure 21:
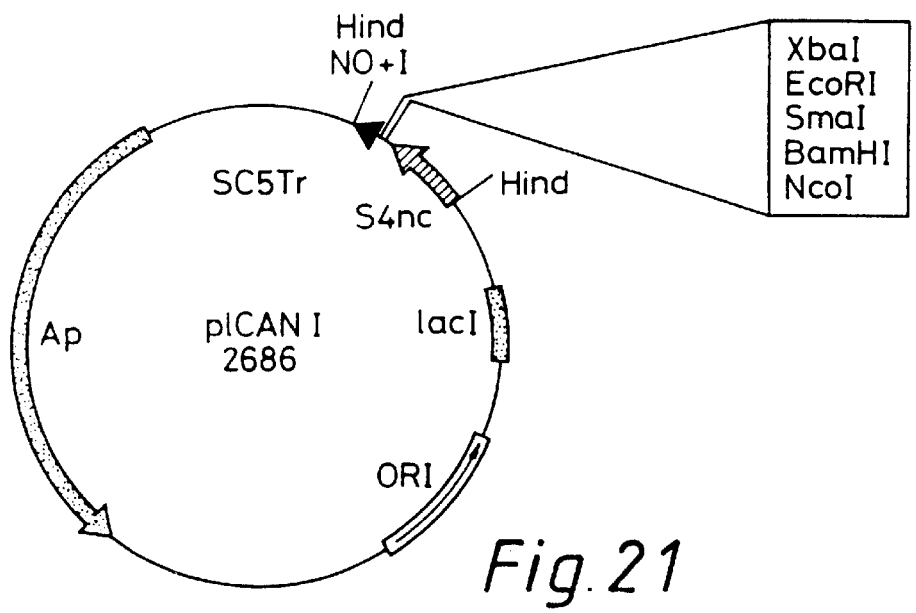

FIG. 21 is a diagramatic representation of a cloning vector utilising SCSV DNA transcription regulatory signals.

Figure 22:
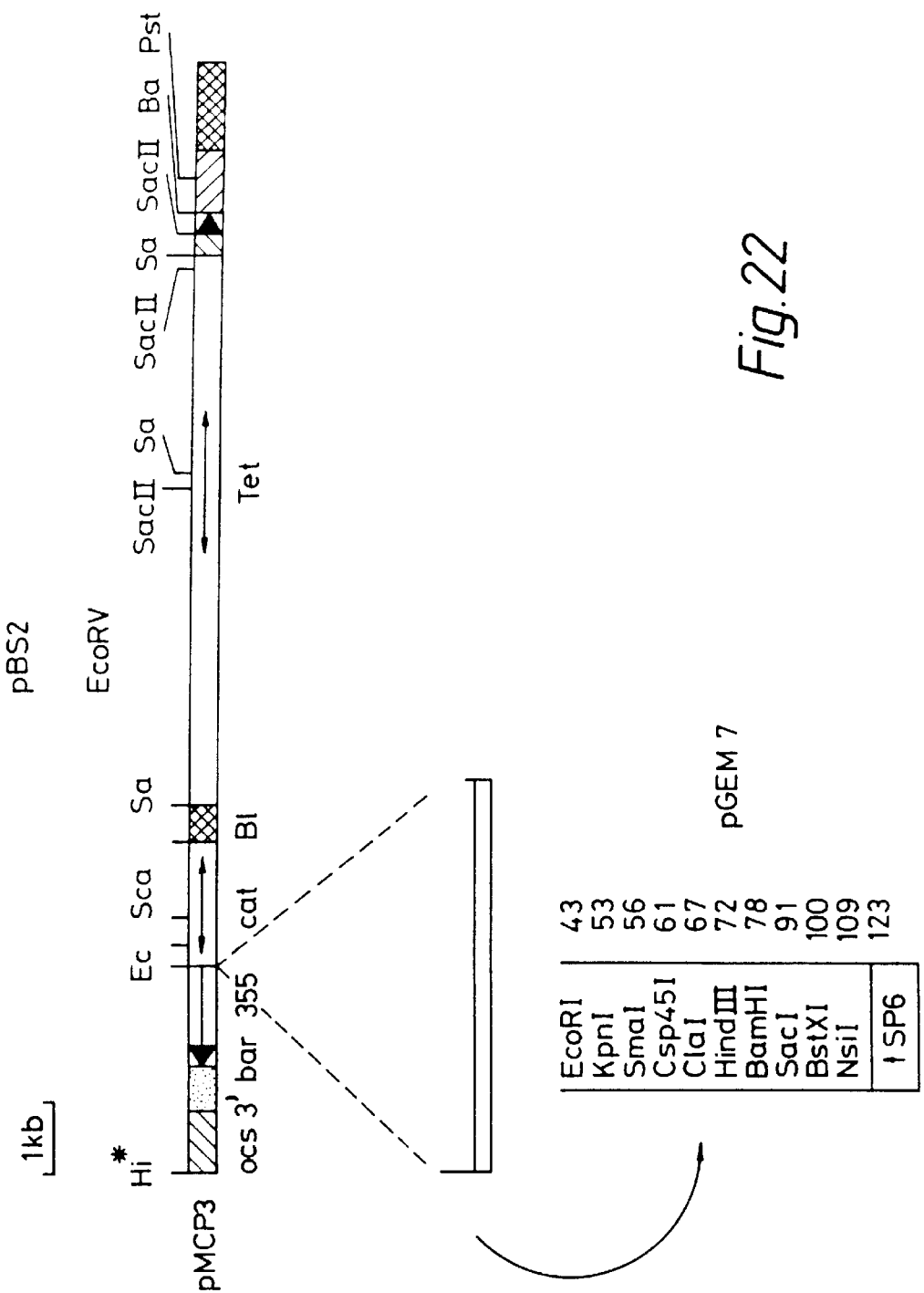

FIG. 22 is a diagramatic representation of SCSV segment 2 dimer construct pBS2. This construct was created by cloning a tandem repeat of the SCSV segment 2 DNA (containing a whole functional seg 2 transcription unit) into the polylinker site of pGEM7 which was then cloned into a reduced version of the pMCP3 binary vector (Khan et al., 1994).

A summary of the trascription activities facilitated by the SCSV transcription regulatory elements is shown in Table 19.

EXAMPLE 1

SCSV DNA Sequence Determination

The F isolate of SCSV (Chu et al. 1993a) was used for sequence determination. Full-length clones of the SCSV genome components were created from the replicative form (RF) DNA as described by Chu et al. (1993a). Other clones were created from the RF by PCR with SCSV specific primers designed from known sequences.

The dideoxy chain termination method (Sanger et al., 1977) was used to sequence either M13 ssDNA templates (Sambrook et al., 1989) or dsDNA templates prepared by the CTAB method (Del Sal et al., 1989) from clones described above. Sequence analysis was carried out using the University of Wisconsin Genetics Computer Group Sequence Analysis Software Package (Devereaux et al., 1984).

EXAMPLE 2

Plasmid Construction

DNA manipulation techniques used were as described by Sambrook et al. (1989). The entire non-coding regions of all 7 DNA segments of SCSV were amplified by PCR using specific primers (See Table 8) with appropriate restriction enzyme recognition sites for cloning into the plasmid vectors. The amplified DNA fragments were separately cloned into the respective expression vectors upstream of a promoterless GUS reporter gene in the appropriate orientation to produce the SCSV promoter-GUS fusion constructs as shown in the FIGS. 3 and 4. The expression vector pHW9 (FIG. 3) followed by cloning into the binazy vector pGA470 (An et al., 1985) were used for tobacco transformation. The expression vector pKGO was used for GUS expression in protoplasts (FIG. 4) and the binary vector pTAB10 was used for subterranean clover transformation (FIG. 5). pKGO was constructed by cloning the XhoI fragment of pKIWI101 (Janssen and Gardner, 1989) containing the GUS gene and the OCS terminator sequence into the Sal/I site of pJKKm (Kirschman and Cramer, 1988). Corresponding plasmids containing the 35S promoter fused to GUS were used as controls. The junctions of the clones were checked by sequencing. A promoterless GUS construct was used as a control.

Deletion derivatives of the SCSV segments 5 and 7 promoters were made by digesting the full-length non-coding sequence with an appropriate enzyme to produce the desired deletion (FIG. 4).

To investigate the phenomenon of transactivation, the S5nc:GUS expression cassette was excised from recombinant pKGO constructs and cloned into a pGEM plasmid containing the seg 2 RAP coding region expressed from the 35S promoter. The resultant plasmid canying both the SCSV promoter:GUS and the 35S promoter:seg 2 RAP expression cassettes were electroporated into protoplasts.

EXAMPLE 3

Protoplast Isolation and Transient Gene Expression

Recombinant plasmids were extracted from *E. coli* by alkaline lysis followed by purification through Qiagen columns as described in the Qiagen Plasmid Handbook.

Suspension cell cultures were used to isolate *Nicotiana-plumbaginifolia* (Last et al. 1991) and subterranean clover cv. Woogenellup protoplasts (Chu et al. 1 993b). Purified plasmids were electroporated into protoplasts of subterranean clover or *Nicotiana-plumbaginifolia* as described by Taylor and Larkin (1988). Protoplasts were harvested 3 days later and assayed fluorometrically for transient GUS activity using 4-methyl umbelliferyl β-glucuronide as substrate (see below). All experiments were done using duplicate samples per treatment.

EXAMPLE 4

Transformation of Tobacco with SCSV-promoter-GUS Fusion Constructs

The recombinant pGA470 binary constructs containing the various SCSV promoter:GUS expression cassettes were separately transformed into *Agrobacterium tumefaciens* strain LBA4404 (Hoekema et al. 1983) by electroporation as described by Nagel et al. (1990). *Nicotiana tobacum* cv. Wisconsin 38 were transformed and regenerated as described by Ellis et al. (1987).

EXAMPLE 5

Transformation of Subterranean Clover with SCSV-promoter-GUS Fusion construct

The recombinant pTAB10 binary vector containing the S7nc:GUS fusion construct (pBS150) was transformed into *Agrobacterium tumefaciens* strain AGL1 (Lazo et al. 1991) by triparental mating (Ditta et al. 1980). Subterranean clover cv. Larisa was transformed by Agrobacterium-mediated transformation and regenerated as described by Khan et al. (1994).

EXAMPLE 6

GUS Assays

Protoplasts were lysed by sonication in the presence of 0.3% v/v Triton X-100 immediately after harvest. GUS activity of the soluble extract was determined in a fluorometric assay using the substrate 4-methyl umbelliferyl β-D-glucuronide (MUG) (Jefferson et al., 1987). Fluorescence was measured using a Labsystem Fluoroskan II spectrophotometer.

GUS expression in intact trnnsgenic tissues was detected by histochemical staining in 5-bromo-4-chloro-3-indolyl-β-glucuronic acid (X-gluc) (Jefferson et al., 1987) and by fluorometric assay of the soluble extract using MUG.

EXAMPLE 7

Sequence of SCSV non-coding Region

The complete sequences of all the 7 known SCSV DNA circles have been determined (FIG. 6). Each DNA contains a non-coding region with signals (TATA boxes) for promoter activity (Table 2). These sequences have not been described or isolated before. Sequence comparison of the non-coding regions comprising these promoters showed that segments 3 and 5 are most similar, sharing 258 conserved nucleotides out of an average of 491 nucleotides in the non-coding regions of the DNAs. Segments 3, 4, 5 and 7 contain 170 conserved bases between them while only 152 bases are conserved between Segments 1, 3, 4, 5 and 7. The sequence variations in the non-coding regions of the SCSV DNAs suggest that the transcription and replication of the different SCSV genes may be regulated differently.

EXAMPLE 8

Transient Activity of SCSV Promoters in Protoplasts

The promoter activities of two SCSV DNA non-coding regions have been demonstrated directly by transient expression of GUS using SCSV promoter:GUS fusion constructs in subterranean clover (Table 3) and tobacco protoplasts (Table 4). These results showed that both segment 5 and segment 7 promoters are fimctional in the absence of other SCSV DNA components. The SCSV promoters are also finctional in protoplasts of either a natural host (subterranean clover) or a non host (tobacco). In tobacco protoplasts, the segment 7 promoter was similar in activity to the 35S promoter while the segment 5 (coat protein) promoter consistently showed activity about half that of the CaMV 35S promoter (Table 4). However, the activity of both promoters were higher in subterranean clover protoplasts, with the activity of the segment 7 promoter showing up to several times that of the 35S promoter (Table 3), suggesting that SCSV promoters work better in certain legumes than te widely used 35S promoter. The activity of the segment 7 promoter also appeared to be more variable in subterranean clover protoplasts than the others tested.

Plasmids containing various deletion derivatives of the non-coding sequence of segments 5 and 7 fused to GUS were also constructed (FIG. 4) and electroporated into protoplasts (Table 5). GUS assays of protoplasts transfected with these constructs showed that neither the stem-loop nor the common region were necessary for promoter activity although the latter was required for flill activity (Table 5). The DNA sequence required for high level promoter activity appears to be less than 300 bp which is smaller than that required for other promoters, such as 35S promoter (Odell et al., 1985).

EXAMPLE 9

Transactivation of SCSV Promoter Activity by SCSV Segment 2 Gene Product

When co-electroporated with a 35S promoter:seg 2 RAP gene construct, the activities of GUS driven by the seg 5 promoter apparently increased by about 2 fold in both subterranean clover and tobacco protoplasts (Table 6). The segment 7 promoter activity may also be increased when co-electroporated with the 35S:seg 2 RAP construct but further experiments are needed to confirm this.

Transactivation of GUS activity was also apparently observed when the S5nc:GUS construct was co-electroporated with a binary vector plasmid (pBS2) containing a tandem repeat (dimer) of the segment 2 DNA (Table 6). A map of SCSV segment 2 dimer construct -pBS2 is shown in FIG. 22. This construct was created by cloning a tandem repeat of the SCSV segment 2 DNA (containing a whole finctional seg 2 transcription unit) into the polylinker site of pGEM7 which was then cloned into a reduced version of the pMCP3 binary vector (Khan et al., 1994). The results suggest that both SCSV promoters are expressed concurrently. Thus, different SCSV promoters can either be used in combination with a 35S promoter or be used simultaneously to facilitate concurrent expression of multiple transgenes in plants. In contrast, reduced transgene activity has been observed when the 35S promoter is used in multiple or multiple copy transgenes (Linn et al., 1990; Matzke and Matzke, 1991; Scheid et al., 1991; Carvalho et al., 1992).

EXAMPLE 10

Activity of SCSV Promoters in Transgenic Plants

All the SCSV promoters, except those from segments 2 and 6, have been shown to be capable of driving expression of transgenes in tobacco plants (FIG. 7). The level of activity of the promoters measured by the MUG assay varied from plant to plant and from one promoter to another but is generally lower than that of the 35S promoter (Table 7).

Histochemical staing of intact transgenic tobacco tissues showed that the activity of the S4nc promoter appears to be constitutive and GUS activity was detected in all plant organs. The others are generally restricted to the vascular tissues although expression is also detected in pollen.

In transgenic subterranean clover plants expressing the S7nc:GUS gene construct, histochemical staining showed that GUS activity is found in leaves, stems and petioles. The distribution of GUS activity is mostly constitutive although in some tissues, the activity is largely in vascular tissues (FIG. 7). In these plants, the level of promoter activity also varies from plant to plant but the activity is generally comparable to that of the 35S promoter.

These results indicate that the SCSV promoters provide a choice of promoters that can be used either independently or simultaneously to control the expression of one or more foreign genes in a wide range of plants and tissue types. Legumes are a major target for application. The activity of these promoters also can be enhanced by the presence of the seg 2 gene product. Thus, these promoters appear to have significant advantages over the CaMV 35S promoter, both in levels of expression, size and in overcoming some negative features of the 35S promoter. They would be applicable in a wide range of transgenic applications.

TABLE 1

Properties of plant viruses with small and multiple encapsidated circular ssDNAs (Plant Nanoviruses)

| Virus | Hosts | Vector | No. of circles | Size (kb) | Coat protein (kDa) |
|---|---|---|---|---|---|
| FBNYV | Legumes | Aphids | 2+ | 1 | 22 |
| MDV | Legumes | Aphids | 1+ | 1 | 21 |
| SCSV | Legumes | Aphids | 7 | 1 | 19 |
| BBTV | Monocots | Aphids | 6+ | 1–1.2 | 20 |
| CFDV | Monocots | Planthopper | 1+ | 1.3 | 25 |

Compiled from data presented at the Sixth International Congress of Plant Pathology, Montreal, July, 1993. FBNYV=faba bean necrotic yellow virus, MDV=milk vetch dwarf virus, SCSV=subterranean clover stunt virus, BBTV=banana bunchy top virus, CFDV=coconut foliar decay virus.

TABLE 2

Transcription units and putative gene functions of the SCSV DNA segments

| DNA Segment | Size (bases) | Segment Function | Non-Coding Region (bases) | TATA Box Pos[a] | TATA Box Sequence | ORF Pos[b] | ORF # aa | ORF Mr (kDa) | Termination Codon | Polyadenylation Signal |
|---|---|---|---|---|---|---|---|---|---|---|
| 1 | 1001 | Unknown | 661 | 201 | TATAAAT[c] | 48 | 112 | 12.7 | TGA[f] | AATTAT[h] |
| 2 | 1022 | Replication | 178 | −8 | TATATAT[d] | 102 | 280 | 32.5 | TGA[f] | AATAAA[i] |
| 3 | 991 | Unknown | 495 | 326 | TATAAAT[c] | 57 | 164 | 19.1 | TGA[f] | AATAAA[i] |
| 4 | 1002 | Unknown | 539 | 285 | TATAAAT[c] | 71 | 153 | 17.7 | TAA[g] | AATAAA[i] |
| 5 | 998 | Coat protein | 487 | 330 | TATAAAT[c] | 48 | 169 | 18.7 | TAA[g] | AATAAA[i] |
| 6 | 1017 | Replication | 158 | −7 | AATATAA[e] | 66 | 285 | 33.5 | TGA[f] | AATAAA[i] |
| 7 | 988 | Unknown | 546 | 324 | TATAAAT[c] | 67 | 146 | 16.9 | TAA[f] | AATAAA[i] |

Figure 1:
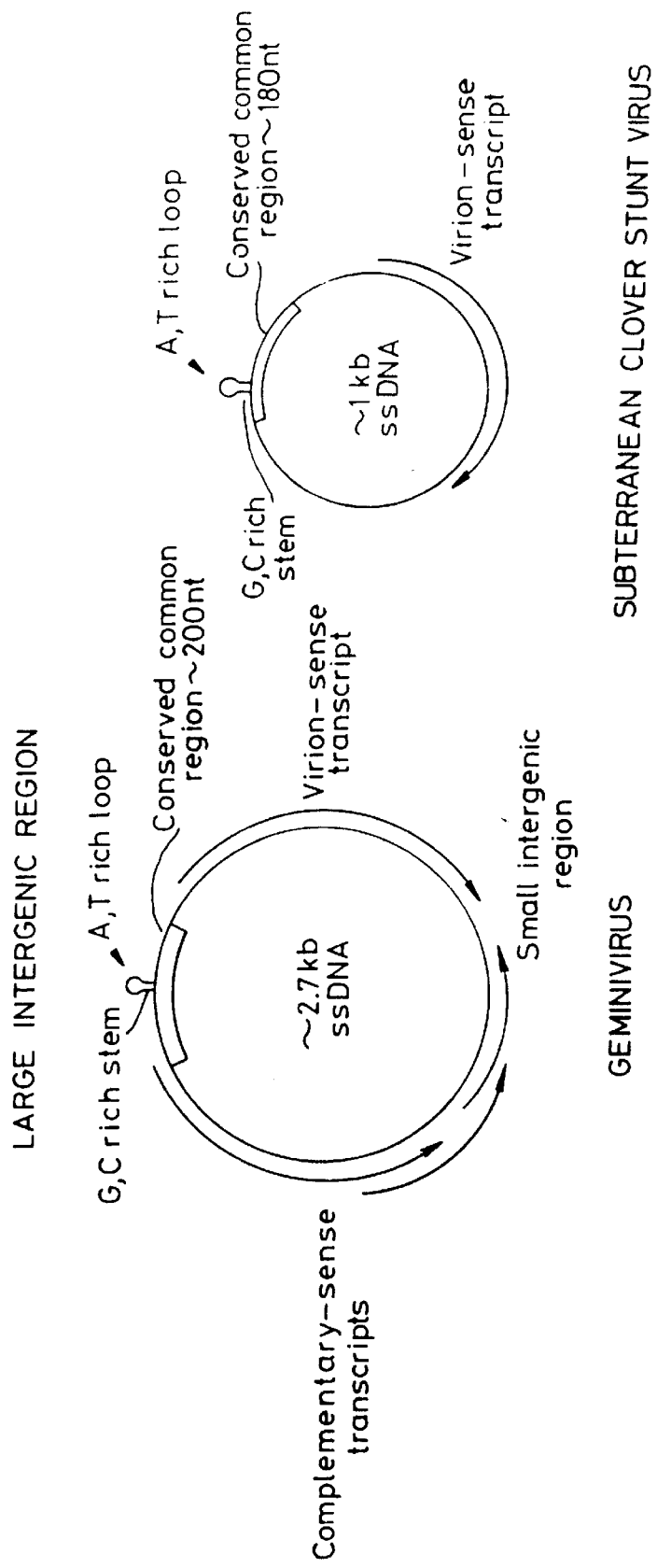
FIG. 1 is a schematic representation showing the structures and transcription units found in a representative DNA component of a typical geminivirus and SCSV, both of which contain a ssDNA genome.
Figure 2:
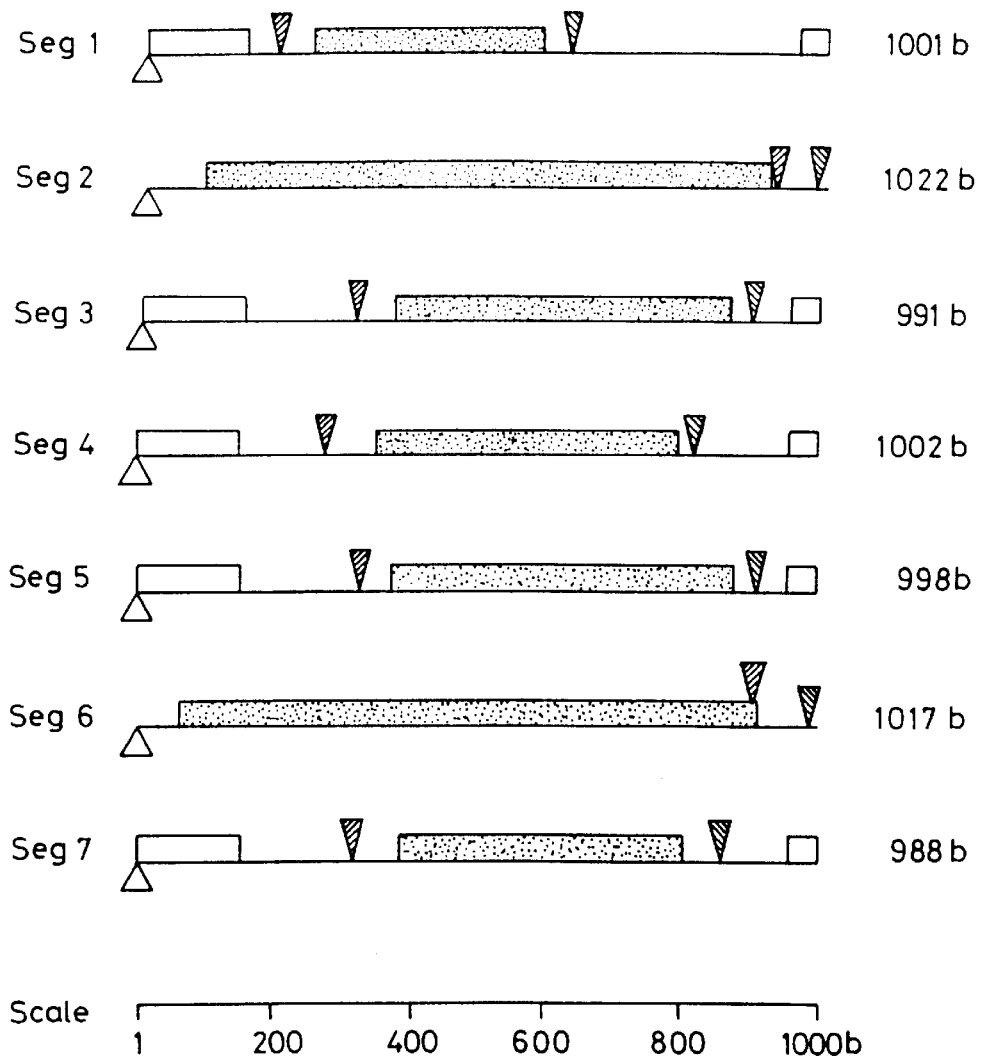
FIG. 2 is a schematic representation showing the seven DNA segments found in the genome of SCSV in a linear form, indicating the positions of the stem-loop structure, the common region, the open reading frame (ORF), the TATA box and the termination and polyadenylation signals on each DNA.

[a]Position of the TATA box is the number of bases from the first nucleotide of the stem-loop to and including the first base of the TATA box. See FIG. 1 for a graphic presentation of the genome segments;
[b]Position of the ORF is the number of bases from the first base of the TATA box to and including the first base of the initiation codon;
[c]SEQ ID NO: 9;
[d]SEQ ID NO: 10;
[e]SEQ ID NO: 11;
[f]SEQ ID NO: 12;
[g]SEQ ID NO: 13;
[h]SEQ ID NO: 14;
[i]SEQ ID NO: 15.

TABLE 3

SCSV promoter directed GUS activity in subterranean clover protoplasts

| | GUS Activities | | | | |
|---|---|---|---|---|---|
| | Expt 1 | | Expt 2 | | Average |
| Treatments | Act | % 35S | Act | % 35S | % 35S |
| No DNA | 10 | 0% | 13.1 | 0% | 0% |
| 35S:GUS | 27.3 | 100% | 36.6 | 100% | 100% |
| S5nc:GUS | 22.6 | 73% | 40.2 | 116% | 95% |
| S7nc:GUS | 36 | 147% | 117 | 385% | 266% |

All experiments were done using duplicate samples per treatment. GUS activity was measured using a Labsystem Fluoroskan II spectrophotometer and is presented both in absolute activity (Act) and as a percentage of 35S:GUS activity (%35S).

constructs are represented as "promoter:reporter gene". For example, "35S:GUS" is the 35S promoter and the GUS reporter gene. "S5nc" and "S7nc" are the promoters for segments 5 and 7, respectively of SCSV.

TABLE 4

SCSV promoter directed GUS activity in tobacco protoplasts

| | GUS Activities | | | | |
|---|---|---|---|---|---|
| | Expt 1 | | Expt 2 | | Average |
| Treatments | Act | % 35S | Act | % 35S | % 35S |
| No DNA | 13.8 | 0% | 10.5 | 0% | 0% |
| 35S:GUS | 113 | 100% | 117 | 100% | 100% |
| S5nc:GUS | 52.3 | 39% | 61 | 48% | 44% |
| S7nc:GUS | 93 | 80% | 106 | 90% | 85% |

All experiments were done using duplicate samples per treatment. GUS activity was measured using a Labsystem Fluoroskan II spectrophotometer and is presented both in absolute activity (Act) and as a percentage of 35S:GUS activity (%35S).

TABLE 5

Promoter activities (GUS expression levels) of deletion derivatives of segment 5 and 7 non-coding regions in protoplasts. Levels are expressed as percentages of the activity of the respective full-length non-coding sequence.

| | | GUS Activity | | | |
|---|---|---|---|---|---|
| | | Tobacco | | Subclover | |
| Promoter | Deletion[a] | Expt 1 | Expt 2 | Expt 1 | Expt 2 |
| Segment 5 | dNde | 101 | 110 | — | — |
| | dPml (stem-loop) | 65 | 88 | — | — |
| | dAfl (Stem-loop + common region) | 70 | 102 | 63 | 91 |
| | dPst | 5 | 18 | 6 | 4 |
| Segment 7 | dAfl (stem-loop + common region) | 50 | 55 | 67 | 39 |

[1]See FIG. 4 for maps of deletion derivatives.

TABLE 6

Transactivation of segment 5 promoter activity (GUS expression) in tobacco and subterranean clover protoplasts by gene product of segment 2.

| | | GUS Activity | | | |
|---|---|---|---|---|---|
| Promoter Construct | Protoplasts | Expt 1 | Expt 2 | Expt 3 | Expt 4 |
| S5nc:GUS | Tobacco | 100 | 100 | — | — |
| S5nc:GUS + 35S:Seg 2 RAP | Tobacco | 262 | 217 | — | — |
| S5nc:GUS | Subclover | 100 | 100 | 100 | 100 |
| S5nc:GUS + 35S:Seg 2 RAP | Subclover | 132 | 176 | 188 | 770 |
| S5nc:GUS + Seg 2 dimer[b] | Subclover | — | — | — | 320 |

[a]GUS activities are expressed as percentages of the S5nc:GUS construct in each experiment
[b]See Example 9

TABLE 7

Relative GUS activity in leaf extracts of independent transgenic tobacco plants containing different promoter:GUS constructs as determined by fluorometric assays[a]

| Promoter | | GUS Activity | Average |
|---|---|---|---|
| Non transgenic control | | 123 | |
| | Average | | 123 |
| 35S | #3 | 38,431 | |
| | #6 | 20,052 | |
| | #8 | 20,648 | |
| | #11 | 28.325 | |
| | #12 | 24,700 | |
| | Average | | 26,431 |
| S4nc | #1 | 7,229 | |
| | #2 | 4,690 | |
| | #5B | 4,300 | |
| | #9 | 6,218 | |
| | #18 | 4,895 | |
| | #19 | 6,098 | |
| | Average | | 5,572 |
| S7nc | #4 | 642 | |
| | Average | | 642 |

[1]GUS activity presented is the best 25% of the transgenic plants tested.

EXAMPLE 11

Further Characterisation of SCSV Promoter Activities in Transgenic Plants

Transgenic plants of tobacco transformed with the five (Segments 1, 3, 4, 5 and 7) SCSV promoter:GUS fusion cassettes were assayed for GUS activity by both histochemical (FIGS. 8 and 9) and fluorometric assays (FIG. 10). Samples taken from tissue-cultured and young glasshouse-grown plants produced the same GUS expression pattern. GUS activity was observed in all plant parts, including roots, stems, leaves, petioles and all flower parts. Promoter 5 construct gave relative lower GUS expression in pollen than other promoters. The results from fluorometric assays confirmed previous data showing that segment 4 promoter was the highest expressor, with activity 10-fold or greater than the rest (FIG. 10), but is still lower than that of the 35S promoter. The expression levels of the segment 1, 3, 5 and 7 promoters were comparable to those of the phloem-specific promoter roIC in tobacco (Schmulling et al., 1989; Sugaya et al., 1989). Plants transformed with the promoterless GUS construct did not express GUS by either assay method. Histochemical assays showed that expression of all promoter constructs was the highest in vascular tissues, with high expressors being more constitutive than low expressors which are more vascular-limited (FIG. 8). In general, promoter 1, 3, 5 and 7 constructs are expressed mostly in the vascular tissues. In particular, GUS expression by promoter 1 and 3 constructs are mainly restricted to phloem tissues. However, for all promoters histochemical staining of leaves showed that GUS expression in these tissues are often blotchy (constitutive and vascular-limted) and variable between leaves of the same plant. Dark field microscopy (Jacobsen-Lyon et al., 1995) also showed that none are strictly vascular-limited (FIG. 9).

Twenty primary transgenic subterranean clover plants expressing the seg 7 promoter:GUS gene were further characterised by histochemical assays (Table 9). These assays showed that GUS activity was observed in all plant parts, including roots, stems, leaves and petioles. GUS expression was the highest in vascular tissues, with some leaves being more constitutive and blotchy than other organs and high GUS expressing plants being more constitutive than low expressing ones. Samples taken from tissue-cultured and glasshouse-grown plants produced the same GUS expression pattern.

EXAMPLE 12

Detection of Promoter Activity in SCSV Segment 2 DNA

Experiments showed that the non-coding regions from the SCSV segments 2 and 6 DNAs were unable to drive the expression of GUS gene in transgenic tobacco. These regions are only 179 and 159 nucleotides long, respectively, and it is likely that additional sequences are required for promoter activity. To test this hypothesis, a new segment 2 promoter sequence was constructed consisting of the DNA fragment from nucleotides 526 to 46 and fused to the promoterless GUS vector pKGO (FIG. 11). The fusion construct was electroporated into tobacco protoplasts. Gus activity was detected in electroporated tobacco protoplasts at levels similar to that of segment 5 promoter:GUS construct (Table 10).

A binary vector containing the above SRnc promoter-:GUS fusion DNA was also transformed into tobacco plants as described in Example 4. Histochemical staining of several transformed tobacco plants showed that GUS expression was mainly vascular. These results showed that additional sequence from the SCSV segment 2 DNA coding region is necessary for promoter function. Since the SCSV segment 6 is a variant of the segment 2, it is expected that a similar construct comprising the noncoding and part of the coding region of this DNA will produce an active promoter. Thus, all SCSV promoters are expected to be suitable for driving gene expression in plants.

EXAMPLE 13

Enhancement of Gene Expression by SCSV Transcription Termination and Polyadenylation Signals Effective gene expression requires not only a promoter, but also specific nucleotide sequences at the 3' end of the coding region of the gene, known as the termination and polyadenylation signals (Messing et al., 1983; Joshi 1987b; Gil and Proudfoot, 1984; Rothnie et al., 1994). These special sequences are required to signal the RNA polymerase to stop transcription and to allow further processing of the RNA transcript. The activity of the termination and polyadenylation signals may affect the transcription efficiency and stability of the RNA being transcribed. Some widely used termination/polyadenylation sequences include those from the NOS aepicker et al., 1982), OCS (Janssen and Gardner, 1989) and CaMV 35S (Pietrzak et al., 1986) genes.

Each of the SCSV DNA segment (or component) contained a terminator sequence comprising a termination and a polyadenylation signal sequence in the noncoding region (Table 11). To demonstrate activity of the termination/polyadenylation signals in SCSV DNA, GUS expression vectors containing either the segment 3 or segment 5 polyadenylation and termination signal (FIG. 12) was constructed and subjected to transient expression in tobacco protoplasts. The respective terminator sequence was amplified by PCR with several restriction sites incorporated into the primers (FIG. 12). The amplified terminator fragments were cut with the indicated restriction enzymes and cloned into the pKGO recombinant plasmid containing either S1nc or S4nc promoter:GUS:OCS3' constructs, from which the OCS3' sequence has been deleted (FIG. 12). The resultant S1nc:GUS:SC3Tr (the segment 1 promoter here carries a deletion of the HindIII fragment from nucleotides 641–782 which has no effect on GUS activity) and S4nc:GUS:S5Tr constructs were electroporated into tobacco protoplasts and assayed for GUS activity. The results showed that GUS activity was increased 2 to 3-fold when the SCSV termination/polyadenylation sequence was used instead of the commonly used OCS termination/polyadenylation sequence in the same construct (Table 12). In the same experiment, the construct S1nc:GUS:S3Tr produced over two-fold higher activity than the 35S:GUS:OCS3' construct (Table 12). These results indicate that each of the SCSV DNA components contains a different termination and polyadenylation signal sequence which can be used in various combination with the SCSV promoters to regulate and/or enhance expression of foreign genes in plants. As with the SCSV promoter sequences, the SCSV termination/polyadenylation sequences are advantageous over currently available termination/polyadenylation sequences by their small sizes (160–170 nucleotides) and the availability of a broad range of transcription regulators with different strengths and tissue specificities for genetic manipulation. The results also show that the use of a SCSV promoter in combination with a SCSV terminator sequence in higher levels of gene expression than constructs using the 35S promoter in conjunction with one of the common transcription terminator sequences.

EXAMPLE 14

Activity of SCSV Promoters in Transgenic Potato Plants pGA470 binary vector containing the S4nc:GUS:NOS fusion construct cloned in pHW9 (FIG. 3) was used to transform potato plants. pHW9 is derived from pHW8 (Dolferus et al., 1994) into which the polylinker from pGEM3zf(+) is inserted. The recombinant binary vector was transformed into Agrobacterium tumefaciens strain LBA4404 by electroporation (Nagel et al., 1990). Potato cultivars Atlantic and Sebago were transformed and regenerated essentially as described by Wenzler et al. (1989) except for the following modifications. Stem pieces instead of leaf pieces were used for transformation and 10 mg/l of benzylaminopurine (BAP) instead of 2.24 mg/l was used during co-cultivation. After co-cultivation, stage 1 medium is supplemented with 100 mg/l of cefotaxime and not kanamycin or carbenicillin. Stage II medium contained 2 mg/l BAP, 5 mg/l GA3, 100 mg/l kanamycin and 100 mg/l cefotaxime.

Six transformed plants comprising 5 of cultivar Atlantic and 1 of cultivar Sebago were transferred and grown in the glasshouse for 10–11 weeks until small tubers formed. Tissues from different parts of the plants were assayed by histochemical GUS staining. The results showed that GUS was highly expressed in all plant parts including roots, stolons, tubers, stems and leaves but the expression was predominantly vascular, including cambium, phloem elements and some xylem elements (FIG. 13). As in other transgenic hosts, GUS expression in non-vascular tissues of highly GUS active plant materials, especially young tubers, was more evident than in less active tissues when compared with plants transformed with a 35S:GUS:NOS construct, SCSV promoter directed GUS expression in tubers was at least as high as that of the 35S:GUS construct.

EXAMPLE 15

Activity of SCSV Segment 7 Promoter in Transgenic Cotton Plants pGA470 binary vector containing S7nc:GUS:NOS fusion construct cloned in pHW9 was used to transform cotton plants. The recombinant binary vector was transformed into Agrobacterium tumefaciens strain AGL1 by triparental mating. Cotton (Gossypium hirsutum) cv. coker 315 was transformed and regenerated as described by Cousins et al. (1991).

Transformed plants were grown in the glasshouse and leaf tissues from 18 independent transgenic plants were assayed for GUS activity by histochemical staining. GUS activity varied between plants. Five of these plants showed strong GUS expression, similar in range to 35S promoter driven GUS expression and was predominantly in the vascular tissues (FIG. 14). GUS activity was especially strong in the gossypol glands. As in other trnnsgenic hosts, GUS staining in highly expressed tissues were also constitutive.

A variety of tissues from these plants were then stained and vascular expression was observed in all organs including roots, stems, petioles, petals and other vascularised floral parts. Expression appears to be particularly high in young flower buds. Seedlings from one of the lines was screened for GUS activity. All 10 progenies stained heavily in roots and leaves indicating that the gene was inherited and that the line probably contained more than one independent insertion site.

EXAMPLE 16

Stability of Transformed SCSV Promoter: GUS Expression Cassette in Transgenic Plants The stability of GUS expression driven by the various SCSV promoters in transgenic tobacco and subclover were fuirther characterised in T1 generation seedlings of subterranean clover and tobacco plants.

In tobacco, T1 seedlings from 10 independent transgenic lines were assayed by histochemical staining. The results showed that the expression of the GUS gene driven by all the five (segments 1,3,4,5 and 7) promoters was stable in the T1 seedlings, with the pattern of expression being maintained in all cases between T0 and T1 plant tissues of the same age. In very young stems where the vascular tissues are not well differentiated, expression from all promoters were very high and was detected through out the stem tissues. Gradual vascular limitation occurs with age and with increasing differentiation of the vascular bundles. As with T0 plants, the segment 4 promoter mediated GUS expression was more constitutive than others.

Fifty 2–3 month old T1 seedlings from 15 independent transgenic subclover plants expressing the S7nc:GUS fusion construct were assayed for GUS activity by histochemical and fluorometric assays. The results showed that the expression of the GUS gene driven by the segment 7 promoter was stable in T1 seedlings, with the pattern of expression being maintained between T0 and T1 plant tissues of the same age. GUS expression was found to generally segregate at the expected ratio of 3:1. The preliminary results from fluorometric assays confirmed the histochemical data suggesting that this segnient 7 promoter construct had GUS activity somewhat lower than that of the 35S promoter in leaves and petioles (Table 13). GUS activity in subterranean clover s tems, however, was 3-fold higher than in petioles and 6fold higher than in leaves (Table 14). The age of the plants at the time of assay was 2 to 3 months.

EXAMPLE 17

Transient Activity of SCSV Promoter in Soybean Leaves

The SCSV promoter:GUSconstruct used (Table 15) was derived from the promoterless GUS plasmid pKGO (FIG. 4;

pJKKmf(-) K1W1 GUS:OCS) described previously while the 35S promoter:GUS construct was pGUS. pGUS is derived by cloning the Gus gene from pKIWI101 into the plant expression vector pDH51 (Pietrzak et al., 1986).

For transient GUS expression in soybean tissues, the GUS constructs were introduced into tissues tissues by particle bombardment using the Bio-Rad Biolistic PDS-1000/He Particle Delivery System as above. A 50 µl suspension containing 3 mg of a 1:1 ratio of 1 and 5 µgold particles plus 6 µg of DNA was shot onto plates containing 3 leaves each. Fully expanded leaves used in these experiments were prepared from 24 day old soybean plants cv. Wayne. After particle bombardment, GUS activity was assayed 24 hours later by vaccuum infiltration of the leaves with X-Gluc (Craig, 1992).

The results (Table 15) showed that in transient expression in soybean leaves, SCSV segment 4 promoter was more active (25–35 spots/leaf) than the 35S promoter (10–15 spots/leaf) when the respective plasmids were shot into soybean leaves.

EXAMPLE 18

Testing of SCSV Promoters for Callus-specific Expression

All seven SCSV non-coding sequences were cloned into the promoterless GUS vector pHW9. Binary vectors each containing one of the seven SCSV promoter:GUS fusion constructs were transformed into tobacco tissues by Agrobacterium-mediated gene transfer. At 2–3 weeks after transformation, calli containing primodia of transformed shoots were subjected to histochemical GUS staining. Best expression was observed in calli transformed with segment 1 followed by the S4nc:GUS:OCS constructs. This result suggests that the segment 1 promoter is best suitable for selectable marker gene expression and that the segment 4 promoter is best for gene expression.

EXAMPLE 19

Characterisation of Regulatory Sequences of the *Flaveria bidentis* MeA Gene In *Flaveria bidentis* (Chitty et al., 1994) the MeA gene is the gene that codes for the NADP-malic enzyme adapted for C4 photosynthesis. The structure and putative promoter and transcription termination/polyadenylation signal sequences of this gene has been isolated and the terminator sequence determined (FIG. 15). The potential activities of the putative promoter element (MeA 5' sequences) and terminator (MeA 3' sequences) of the *F. bidentis* MeA gene were studied in tralsgenic *F. bidentis* plants using GUS expression vectors (FIG. 16). A long version of the MeA 3' terminator sequence (MeA 3'L=5.5 kb from the stop codon) was used in these experiments. In FIG. 16, the GUS expression cassette ME20 is ligated to the binary vector pGA470 (An et al., 1985) while ME29 is cloned into pGA482 (An, 1986). Plants were transfonned with these vectors as described by Chitty et al. (1994)

Study of GUS activity of the transformed plants by histochemical staining and fluorometric assays showed that the MeA 3' sequence of the gene is required for high level expression of GUS in leaves of transgenic *F. bidentis* plants (Table 16). The 5' sequences of the gene do not appear to contribute to gene expression in leaves but appear to direct expression in meristems and stems in the presence of a suitable transcription termination/polyadenylation signal sequence such as the OCS 3' (Table 16).

EXAMPLE 20

Use of the MeA 3' Termination/polyadenylation Signal Sequences in SCSV Promoter Constructs to Enhance Gene Expression in Monocotyledenous Plants Because most gene control elements are located at the 5' end, the activity of the MeA 3' sequence is tested in conjunction with the S4nc SCSV promoter with the view to enhance gene expression directed by the SCSV promoters. For these experiments, a short version of the MeA 3' terminator sequence was used (MeA 3'S; 900 bases from the stop codon) to prepare GUS expression vectors containing the S4nc promoter with either the OCS 3', SCSV segment 5 3' (SC5Tr) or the MeA 3' transcription termination/polyadenylation signal sequence. These constructs were derived from the promoterless GUS plasmid pKGO described previously and the recombinant plasmid pBS237 containing the S4nc:GUS:MeA3' construct is presented in FIG. 17. GUS activity conferred by these constructs were assayed in Japonica rice callus cv. Taipei 309. The constructs were introduced into rice calli by particle bombardment using the Bio-Rad Biolistic PDS-1000/He Particle Delivery System (Bio-Rad Laboratories) and compared with results obtained in dicotyledonous tissues such as soybean leaves and tobacco protoplasts (Table 17). For rice particle bombardment experiments, 4 mg of a 1:1 ratio of 1 and 5 micron gold particles plus 5 ug of DNA in a total of 50 ul volume was shot onto six plates of calli. The DNA was made up with a 4:1 molar ratio of each of the vectors containing GUS gene to the vector containing the selectable marker gene. The vector containing the selectable marker was pTRA151 (Zheng et al., 1991). Each plate contained 50–100 fresh secondary calli derived from mature embryos. Forty hours after DNA bombardment, GUS activity was detected by placing the calli in 0.3% w/v X-Gluc solution in 100 mM phosphate buffer. Blue spots were counted after overnight incubation.

For transient GUS expression in tobacco and soybean, only the GUS constructs were introduced into protoplasts and leaf tissues, respectively. After electroporation, tobacco protoplasts were assayed for GUS activity as previously described. The constructs were introduced into soybean tissues by particle bombardment as described above.

The results showed that in the monocotyledenous rice tissues, a 16-fold higher activity was obtained with the MeA 3' construct compared to the SCSV terminator (Table 17). In similar experiments, a highly expressed GUS construct containing the ubiquitin promoter:GUS:NOS cassette (Christensen et al., 1992) has about 4-fold higher activity than the SC4:GUS:MeA3' construct.

In the dicotyledonous tissues, similar activities were obtained with both of these constructs in tobacco protoplasts and soybean leaves. However, both were 2-fold higher in activity than that obtained with the OCS terminator in tobacco protoplasts (Table 17).

These results suggest that the MeA3' sequence can be used to enable gene expression directed by SCSV promoters in monocots.

EXAMPLE 21

Use of New Vectors Containing SCSV Promoters and Terminators to Drive a Selectable Marker Gene in Transgenic Plants The suitability of using SCSV promoters to drive a selectable marker gene as a basis for selecting transgenic plants after transformation and regeneration was tested in tobacco plants. The selectable marker used is the kanamycin resistance gene, nptII. Binary vectors containing either a SCSV segment 1 (pBS246) (FIG. 18) or a SCSV seg 7 promoter (pKHAN4) (FIG. 19) fused to the nptII gene were constructed from the pART27 (Gleave, 1992) and pKSB-.bar1 (FIG. 19), respectively. These were transformed separately into tobacco plants (Ellis et al., 1987) and putative transgenic plants were selected under kanamycin selection using 100 µg/ml kanamycin (FIG. 20). Kanamycin resistance was confirmed in the transgenic plants by dot blot assay for the nptII gene activity (McDonnell et al., 1987) and survival of the transgenic plants under 100 µg/ml kanamycin in a rooting medium. The results showed that the SCSV segment promoter construct produced at least as many kanamycin resistant plants as the 35S promoter construct use in the same experiment and is, therefore, as effective as the 35S promoter for selecting transgenic tobacco plants based on kanamycin resistance (Table 18). Tobacco transformed with pKHAN4 is resistant to 100 µg/ml kanamycin in regeneration medium and 50 µg/ml kanamycin in rooting medium. Restriction maps of pKSB.bar1 and pKHAN2 used to produce pKHAN4 are shown in FIG. 19.

EXAMPLE 22

Development of a New Plant Gene Expression Vector System

A new expression vector comprising a SCSV segment 4 promoter and a SCSV segment 5 terminator driving any useful gene of interest (pICAN 1) (FIG. 21) has been constructed from a pGEM derivative and the resultant expression cassette can be inserted into the binary vectors pBS246 and pKHAN4. The resultant binary vectors can then be used to transform plants of economic importance especially cotton, subclover, potato and white clover under kanamycin selection. Other binary vectors can be constructed from different combinations of SCSV promoters and terminators to produce a fall range of binary vector system for plant gene expression.

TABLE 9

GUS activity of SCSV segment 7 promoter:GUS construct in primary transgenic substerranean clover plants (To)

| Plant # | Basta Resistance | GUS Activity |
|---|---|---|
| 1 | R | +++ |
| 2 | R | ++ |
| 3 | R | − |
| 4 | R | ++ |
| 5 | S | ++ |
| 6 | R | − |
| 7 | R | ++++ |
| 8 | R | ++++ |
| 9 | MR | +++ |
| 10 | R | +++ |
| 11 | R | +++ |
| 12 | MR | − |
| 13 | MR | ++ |
| 14 | S | ++ |
| 15 | R | + |
| 16 | N.d. | ++++ |
| 17 | N.d. | +++ |
| 18 | N.d. | − |
| 19 | N.d. | +++ |
| 20 | N.d. | ++ |

Plants were analysed two months after transfer of plants to glasshouse from tissue culture.
Basta (phosphinothricin - [PPT] resistance was assayed by painting basta at 1 gm
PPT/litre onto fully unfolded young leaves and reaction was assayed after one week.
R No damage;
MR Moderate damage to leaflet;
S Leaflet dead
N.d. Not determined

TABLE 8

Sequences and positions of PCR primers for cloning non-coding regions and corresponding PCR fragment sizes.

| Primer 1 Name | Position of 5' end | Primer 1 sequence (5'-3') | Primer 2 Name | Position of 5' end | Primer 2 sequence (5'-3') | Fragment size (bp) |
|---|---|---|---|---|---|---|
| S1n3 (SEQ ID NO: 16) | 241 | GGCGTGCGTCGGCCATGG CGCTATGAAATTCTGAAC | S1nc5 (SEQ ID NO:17) | 577 | GGCGTGCGTCGGGGATCCT ATGTTGTAATTTTATATGG | 665 |
| S2nc3 (SEQ ID NO: 18) | 79 | GGCGTGCGTCGGCCATGG AAGCTTAGAGAGAGAAAG | s2nc5 (SEQ ID NO:19) | 924 | GGCGTGCGTCGGGGATCCA ATAAAAGAATATATATTATTG | 177 |
| S4nc3 (SEQ ID NO: 20) | 347 | CTCACTATAGAACCATGGA CACAAGATTCTAAG | S3nc5 (SEQ ID NO:21) | 863 | CTCACTAAAGGGGATCCT GAGATGTAATTGTG | 502 |
| S4nc3 (SEQ ID NO: 22) | 347 | CTCACTATAGAACCATGGA AAGCCAGAACAAAG | S4nc5 (SEQ ID NO:23) | 803 | CTCACTAAAGGGGATCCT AATTGTTATTATCA | 546 |
| S5nc3 (SEQ ID NO: 24) | 372 | CTCACTATAGAACCATGG TCGTTGTAAAATGAC | S5nc5 (SEQ ID NO:25) | 874 | CTCACTAAAGGGGATCCT AATTGTGATGATT | 523 |
| S6nc3 (SEQ ID NO: 26) | 50 | CTCACTATAGAACCATGG TGGGCCCAGGGAAGCGA | S6nc5 (SEQ ID NO:27) | 903 | CTCACTAAAGGGGATCCT GAAAACTCTGCGAA | 164 |
| S7nc3 (SEQ ID NO: 28) | 383 | CTCACTATAGAACCATGG CTTAAAACCAGAACA | S7nc5 (SEQ ID NO:29) | 817 | CTCACTAAAGGGGATCCT AATTAATAGTAATTATG | 554 |

TABLE 10

GUS activity in tobacco protoplasts directed by SCSV segment 2 promoter to tobacco protoplasts relative to the 35S promoter

|  | GUS Activity | |
|---|---|---|
|  | Experiment | |
| Construct | 1 | 2 |
| S2nc:GUS:OCS3' | 0.46 | 0.45 |
| 35S:GUS:OCS3' | 1 | 1 |

TABLE 11

Putative Polyadenylation and Termination signals in SCSV DNA Components

| DNA Component | Putative Polyadenylation/ Termination Signals |
|---|---|
| Seg. 1 | AATTAT[a]-(N)$_{19}$-TGTGTTTT[c] |
| Seg. 2 | AATAAA[b]-(N)$_{10}$-TTGTTTT[d] |
| Seg. 3 | AATAAA[b]-(N)$_{3}$-TTGTT[e] |
| Seg. 4 | AATAAA[b]-(N)$_{8}$-TTATTGTT[f] |
| Seg. 5 | AATAAA[b]-(N)$_{3}$-TTGTTTT[d] |
| Seg. 6 | AATAAA[b]-(N)$_{9}$-TTGTT[e] |
| Seg. 7 | AATAAA[b]-(N)$_{11}$-TTGTTT[g] |

N, any nucleotide residue, wherein numbers refer to the number of residues in the sequence
[a]SEQ ID NO: 14
[b]SEQ ID NO: 15
[c]SEQ ID NO: 30
[d]SEQ ID NO: 31
[e]SEQ ID NO: 32
[f]SEQ ID NO: 33
[g]SEQ ID NO: 34

TABLE 12

GUS Activity Directed by SCSV Promoter in the presence of different terminators in tobacco protoplasts

|  | GUS ACTIVITY | | | |
|---|---|---|---|---|
|  | Expt 1 | Expt 2 | Expt 3 | Av |
| S4nc:GUS:OCS3' | 551 | 166.3 | — | 358 |
| S4nc:GUS:SC5Tr | 1258 | 311.8 | — | 785 |
| No DNA | 0 | 0 | 0 | 0 |
| S1nc:GUS:OCS3' | — | — | 26 | 26 |
| S1nc [ΔHindIII][a]:GUS:OCS3' | — | — | 29 | 29 |
| S1nc [ΔHindIII]:GUS:SC3Tr | — | — | 84 | 84 |
| 35S:GUS:OCS3' | — | — | 35 | 35 |

In each experiment, duplicate electroporations of each construct was performed.
Results are the average of the duplicates.
[a]Contains a deletion of a HindIII fragment.

TABLE 13

Fluorometric GUS Assay of Independent T1 generation of transgenic subterranean clover plants expressing either the S7nc:GUS or the 35S:GUS Construct

| Construct/Plant # | Leaf (Young) [unfolded] | Petiole (Young) [unfolded] |
|---|---|---|
| S7nc:GUS Plant #1 | 56.6 | 120 |
| S7nc:GUS Plant #2 | 35 | 48 |
| S7nc:GUS Plant #3 | 116 | 140 |
| 35S:GUS Plant #1 | 120 | 238 |
| 35S:GUS Plant #2 | 280 | 238 |

Plants were 2–3 months old when assayed.
Results show differential expression in different tissues.

TABLE 14

Distribution of GUS activity in a T1 generation transgenic subterranean clover plant expressing the S7nc:GUS construct

| Source of Tissue | Leaf | Petiole | Stem |
|---|---|---|---|
| Top-[folded leaf; #1 leaf position] | 1 | 1.9 | 2.0 |
| Middle [#3 leaf position] | 1.6 | 5.8 | 22.0 |
| Bottom [#17 leaf position] | 4.0 | 4.8 | 12.6 |

Plants were 2–3 months old when assayed.
Results show differential expression in different tissues.

TABLE 15

Transient expression of GUS in soybean leaves directed by a SCSV promoter

| Constructs | GUS Expression in soybean leaves* (# spots/leaf) |
|---|---|
| S4nc:GUS:SC5Tr | 25–35 |
| 35S:GUS:35STr | 10–15 |

*Results from one experiment in which spots from 3 leaves were counted in each treatment

TABLE 16

Characterisation of GUS activity directed by MeA 3'L sequence (5.5 kb version) in Transgenic *Flaveria bidentis* Plants

| Constructs | GUS Expression |
|---|---|
| MeA:GUS:MeA 3'L (ME24) | High GUS in leaves High GUS in meristem Moderate GUS in stems |
| MeA:GUS:OCS 3'(ME20) | No GUS in leaves High GUS in meristem Moderate GUS in stems |

TABLE 17

Transient expression of GUS in rice callus, soybean leaves and tobacco protoplasts showing enhancement of SCSV promoter activity by MeA 3's sequences in rice callus

| | GUS Expression | | |
|---|---|---|---|
| Constructs | Rice callus (Rel # spots) | Soybean leaves (Rel # spots)* | Tobacco protoplasts (Fluorescence) |
| S4nc:GUS:OCS3' | ND[a] | ND | 0.49 |
| S4nc:GUS:SC5Tr | 0.06 | 1 | 1.0 |
| S4nc:GUS:MeA 3'S | 1 | 1 | 1.1 |

ND Not done
*Average number of spots from 3 leaves in one experiment

TABLE 18

Selection of putative transgenic tobacco plants transformed with Kanamycin resistance gene driven by 35S or S4nc promoter.

| Selection Criteria | Constructs | % Kanamycin resistant | |
|---|---|---|---|
| npt II dot Blot | 35S:npt II:35STr | (1/3)* | 33% |
| | S1nc:npt II:SC3Tr | (7/16) | 43% |
| Kanamycin selection | 35S:npt II:35STr | (10/21) | 48% |
| in rooting medium | S1nc:npt II:SC3Tr | (11/21) | 52% |

*Number of resistant plants in total number of plants tested.

TABLE 19

Summary of the activities of SCSV transcription regulatory elements in plant tissues

| SCSV promoter | Gene Expressed | Protoplasts | Activity Detected Transgenic Plants |
|---|---|---|---|
| A. | | | |
| Seg 1 | GUS, nptII | Tobacco | Tobacco |
| Seg 2 | GUS | Tobacco | Tobacco |
| Seg 3 | GUS | Not done | Tobacco |
| Seg 4 | GUS | Tobacco | Tobacco, potato |
| Seg 5 | GUS | Tobacco, subclover | Tobacco |
| Seg 6 | None | Not done | Not done* |
| Seg 7 | GUS, nptII | Tobacco, subclover | Tobacco, subclover, cotton |
| SCSV Terminator | Gene Expressed | Protoplasts | Activity Detected Transgenic Plants |
| B. | | | |
| SC3Tr | GUS, nptII | Tobacco | Tobacco |
| SC5Tr | GUS | Tobacco | Not done |

*Sequence used probably insufficient to be active. Additional DNA sequence may be required as shown in segment 2.

BIBLIOGRAPHY

An, G. (1986). Development of plant promoter expression vectors and their use for analysis of differential activity of nopaline synthase promoter in transformed cells. Plant Physiol. 81, 86–91.

An, G., Watson, B. D., Stachel, S., Gordon, M. P. and Nester, E. W. (1985). New cloning vehicles for transformation of higher plants. EMBO J. 4, 277–284.

Benfey, P. N. and Chua, N.-H. (1990). The cauliflower mosaic virus 35S promoter: combinatorial regulation of transcription in plants. Science 250, 959–966.

Burns, T. M., Harding, R. M., Hafner, G., Beetham, P. and Dale, J. L. (1993). Single-stranded DNA genome organisation of banana bunchy top virus. IXth International Congress of Virology, Glasgow, Abstract W62–8.

Chitty, J. A., Burbank, R. T., Marchall, J. S., Chen, Z. and Taylor, W. C., Genetic Transformation of the $C^4$ Plant, Flaveria bidentis, The Plant Journal 6: 949–956, 1994.

Chu, P., Boevink, P., Surin, B., Larkin, P., Keese, P and Waterhouse, P. (1994). Non-germinated single stranded DNA plant viruses. In "Pathogenesis and host-parasite specificity in plant diseases: Vol III. Viruses and Viroids". Pergamon Press.

Chu, P. W. G. and Helns, K. (1988). Novel virus-like particles containing circular single-stranded DNA associated with subterranean clover stunt disease. Virology 167, 38–49.

Chu, P. W. G., Keese, P., Qiu, B. S., Waterhouse, P. M. and Gerlach, W. L. (I 993a). Putative full-length clones of the genomic DNA segments of subterranean clover stunt virus and identification of the segment coding for the viral coat protein. Virus Research 27, 161–171.

Chu, P. W. G., Qiu, B. S., Li., Z-y and Larkin, P. (1993b). Replication of subterranean clover stunt virus in pea and subterranean clover protoplasts. Virus Research 27, 173–183.

Christensen, A. H., Sharrock, R. A. and Quail, P. H. (1992). Maize polyubiquitin genes: structure, thermal perturbation of expression and transcript splicing, and promoter activity following transfer to protoplasts by electroporation. Plant Mol. Biol. 18, 675–689.

Cousin, Y, L., Lyons, B. R. and Llewellyn, D. J. (1991). Transformation of an Australian cotton cultivar: prospects for cotton improvement through genetic engineering. Aus. J. Pl. Physiol. 18, 481–494.

Craig, S., (1992) The GUS Reporter Gene - Application to light and transmission electron microscopy. In GUS protocols: using the GUS gene as a reporter of gene expression. S. R. Gallagher, Ed. Academic Press, Inc., Page 115.

Das, A. (1993). Control of transcription termination by RNA-binding proteins. Ann. Rev. Biochem. 62, 893–930.

de Carvalho, F., Gheysen, G., Kushnir, S., Van Montagu, M., Inze, D. and Castresana, C. (1992). Suppression of β-1,3-glucanase transgene expression in homozygous plants. The EMBO J. 11, 2595–2602.

Depicker, A., Satchel, S., Dhaese, P., Zambryski, P. and Goodman, H. (1982). Nopaline synthase:transcript mapping and DNA sequence. J.Mol. Appl. Genet. 1, 561–575.

Del Sal, G., Manfioletti, G. and Schnider, C. (1989). The CTAB-DNA precipitation method: a common mini-scale preparation of template DNA from pagemids, phages or plasmids suitable for sequencing. Biotechniques 7, 514–518.

Devereaux, J., Haeberli, P. and Smithies, O. (1984). A comprehensive set of sequence analysis programs for the VAX. Nucleic acids Res. 12, 387–395.

Ditta, G., Stanfield, S., Corbin, D. and Helsinki, D. R. (1980). Broad host range DNA cloning system for gramnegative bacteria: construction of a gene bank of Rhizobium meliloti. Proc. Natl. Acad. Sci. USA 77, 7347–7351.

Dolferus, R., Jacobs, M., Peacock, J. W., and Dennis, L. S. (1994). Differential interactions of promoter elements in stress responses of the Arabidopsis Adh Gene. Plant Physiol. 105, 1075–1087.

Ellis, J. G., Llewellyn, D. J., Dennis, E. S. and Peacock, W. J. (1987). Maize Adh-1 promoter sequences control anaerobic regulation: addition of upstream promoter elements from constitutive genes is necessary for expression in tobacco. EMBO J. 6, 11–16.

Gil, A. and Proudfoot, N. J. (1984). Nature 312, 473–474.

Gil, A. and Proudfoot, N. J. (1984). A sequence downstream of AAUAAA is required for rabbit β-globin MRNA 3'-end formation.

Gleave, A. P. (1992). A versatile binary vector system with a T-DNA organisational structure conducive to efficient integration of cloned DNA into the plant genome. Plant Molecular Biology 20, 1203–1207.

Harding, R. M., Bums, T. M. and Dale, J. L. (1991). Virus-like particles associated with banana bunchy top disease contain small single-stranded DNA. J. Gen. Virol. 72, 225–230.

Harding, R. M., Burn, T. M., Hafiier, G., Dietzgen, R. G. and Dale, J. L. (1993). Nucleotide sequence of one component of the banana bunchy top virus genome contains a putative replicase gene. J. Gen. Virology 74, 323–328.

Hatch, M. D. (1987) C4 photosynthesis: A unique blend of modified biochemistry, anatomy and ultrastructure. Biochim. Biophys. Acta 895:81–106.

Higgins, T. J. V. and Spencer, D. (1991). The expression of a chimeric cauliflower mosaic virus (CaMV) 35S-pea vicilin gene in tobacco. Plant Sci. 74, 89–98.

Hoekema, A., Hirsch, P. R., Hooykaas, P. J. J. and Schilperoott, R. A. (1 983). A binary plant vector strategy based on separation of vir- and T-region of the Agrobacterium tumefaciens Ti-plasmid. Nature 303, 179–180.

Isogai, M., Sano, Y. and Kojima, M. (1992). Identification of the unique DNA species in the milk vetch dwarf virus-infected leaves. Ann. Phytopath. Soc. Japan 58, 631–632, Abstract.

Jacobsen-Lyon, K. Jesen, E. O., Jorgensen, J- E., Marcker, K. A., Peacock, W. J. and Dennis, E. S. (1995). Symbiotic and nonsymbiotic hemoglobin genes of *Casurina glauca*. Plant Cell 7,213–223.

Janssen, B. J. and Gardner, R. C. (1989). Localised transient expression of GUS i leaf discs following co-cultivation with Agrobacterium. Plant Mol. Biol. 14, 61–72.

Jefferson, R. A., Kavanagh, T. A. and Bevan, M. W. (1987). GUS fusions: b-glucuronidase as a sensitive and versatile gene fusion marker in higher plants. *EMBO J*. 6, 3901–3907.

Joshi, C. P. (1987). Putative polyadenylation signals in nuclear genes of higher plants: a compilation and analysis. Nucleic Acids Research. 15, 9627–9640.

Katul, L., Vetten, H. J., Maiss, E., Makkouk, K. M. Lesemann, D.-E. and Casper, R. (1993). Characterisation and serology of virus-like parficles associated with faba bean necrotic yellows. Ann. Appl. Biol. 123, 629–647.

Khan, M. R. I., Tabe, L. M., Heath, L. C., Spencer, D. and Higgins, T. J. V. (1994). Agbacterium-mediated transformation of subterranean clover (*Trifolium subterraneum* L.). Plant Physiol 105, 81–88.

Kirschman, J. A. and Cramer, J. H. (1988). Two new tools:multi-purpose cloning vectors carry kanamycin or spectinomycin/streptomycin resistance markers. Gene 58, 163–165.

Last, D. I., Brettell, R. I. S., Chaudhury, A. M., Chamberlain, D. A., Larkin, P. J., Marsh, E. L., Peacock, J. W. and Dennis, E. S. (1991). pEmu: an improved promoter for gene expression in cereal cells. Theor Appl Genet 81, 581–588.

Lazo, G. R., Stein, P. A. and Ludwig, R. A. (1991). A DNA transformation-competent Arabidopsis genomic library in Agrobacterium. Biotechnol. 9, 963–967.

Linn, F., Heidmann, I., Saedler, H. and Meyer, P. (1990). Epigenetic changes in the expression of the maize Z1 gene in *Petunia hybrida*: Role of numbers of integrated gene copies and state of methylation. Mol. Gen. Genet. 222, 329–336.

McDonnell, R. E., Clark, R. D., Smith, W. A. and Hinchee, M. A. (1987). A simplified method for the detection of neomycin phosphotransferase II activity in transformed plant tissues. Plant Mol. Biol. Rep. 5, 380–386.

Matzke, M. A. and Matzke, A. J. M. (1991). Differential inactivation and methylation of a transgene in plants by two suppressor loci containing homologous sequences. Plant Mol. Biol. 16, 821–830.

Messing, J., Geraghty, D., Heidecker, G., Hu, N-T., Kridl, J. and Rubenstein, I. (1983). Plant gene structure. In: "Genetic engineering of plants. An agricultural perspective." Kosuge, T., Meredith, C. P. and Hollaender, A. (eds). Plenum Press, New York. pp 211–277.

Nagel, R., Elliot, A., Masel, A., Birch., R. G. and Manners, J. M. (1990). Electroporation of binary Ti plasmid vector into Agrobacterium tumefaciens and Agrobacterium rhizogenes. FEMS Microbiology Letters 67, 325–328.

Odell, J. T., Nagy, F. and Chua, N.-H. (1985). Identification of DNA sequences required for activity of cauliflower mosaic virus 35S promoter. Nature 313, 810.

Pietrzak, M., Shillito, R. D., Hohn, T. and Potrykus, I. (1986). Expression in plants of two bacterial antibiotic resistance genes after protoplast transformation with a new plant expression vector. Nucleic Acids Res. 14, 5857–5868.

Richardson, J. P. (1993). Transcription ternination. Critical Review in Biochem. and Mol. Biol. 28, 1–30.

Rhode, W., Randles, J. W., Langridge, P. and Hanold, D. (1990). Nucleotide sequence of a circular single-stranded DNA associated with coconut foliar decay virus. Virology 176, 648–651.

Rothnie, H. M., Reid, J. and Hohn, T. (1994). The contribution of AAUAAA and the upstream element UUU-GUA to the efficiency of mRNA 3'-end formation in plants. *EMBO J.* 13, 2200–2210.

Sambrook, J., Fritsch, E. F. and Maniatis, T. (1989). Molecular cloning: a laboratory manual. 2nd ed., Cold Spring Harbor Laboratory Press, New York.

Sanger, F., Nicklen, S. and Coulson, A. R. (1977). DNA sequencing with chain-terminating inhibitors. Proc. Natl. Acad. Sci. USA 74, 5463–5467.

Sano, Y., Isogai, M., Satoh, S. and Kojima. M. (1993). Small virus-like particles containing single-stranded DNAs associated with milk vetch dwarf disease in Japan. 6th Int. Cong. of Plant Path., Montreal, Canada, Jul. 28–Aug. 6, 1993. Abs. 17.1.27.

Scheid, O. M., Paszkowski, J. and Potrykus, I. (1991). Reversible inactivation of a transgene in *Arabidopsis thaliana*. Mol. Gen. Genet. 228, 104–112.

Schmulling, T., Schell, J. and Spena, A. (1989). Promoters of the rolA, B, and C genes of *Agrobacterium rhizogenes* are differentially regulated in plants. Plant Cell 1, 665–670.

Sugaya, S., Hayakawa, K., Handa, T. and Uchimiya, H. (1989). Cell-specific expression of the rolC gene of the TL-DNA of Ri plasmid in transgenic tobacco plants. Plant Cell Physiol. 30, 649–653.

Taylor, B. H. and Larkin, P. J. (1988). Analysis of electroporation efficiency in plant protoplants. Aust. J. Biotech. 1, 52–57.

Thomas, J. E. and Dietzgen, R. G. (1991). Purification, characterization and serological detection of virus-like particles associated with banana bunchy top disease in Australia. J. Gen. Virol. 72,217–224.

Wenzler, H., Mignery, G., May, G. and Park, W. (1989). A rapid and efficient transformation method for the production of large numbers of transgenic potato plants. Plant Science 63, 79–85.

Zheng, Z., Hayashimoto, A., Li, Z. and Murai, N. (1991). Hygromycin resistance gene cassette for vector construction and selection of transformed rice protoplasts. Plant Physiol. 97, 832–835.

What is claimed is:

1. A genetic construct comprising an isolated nanovirus promoter from a multicomponent nanovirus, wherein said nanovirus comprises a multicomponent DNA genome, and wherein said nanovirus promoter is operable in a plant cell and is obtained from a segment of the subterranean clover stunt virus (SCSV) aenome selected from the (roup consisting of:

(i) SCSV segment 1 (SEO ID NO: 1);
(ii) SCSV segment 3 (SEO ID NO: 3);

(iii) SCSV segment 4 (SEO ID NO: 4);

(iv) SCSV segment 5 (SEO ID NO: 5);

(v) SCSV seament 7 (SEO ID NO: 7);

(vi) a nucleotide sequence complementary to any one of (i) to (v); and (vii) a fragment of any one of (i) to (vi) which is operable in a plant cell.

2. The genetic construct according to claim 1 wherein the nanovirus genome comprises at least two DNA components or segments.

3. The genetic construct according to claim 1 further comprising a termination and/or polyadenylation sequence wherein said sequence is operably linked to a gene when said gene is operably linked to said promoter.

4. The genetic construct according to claim 3 wherein said termination and/or polyadenylation sequence is of SCSV origin.

5. The genetic construct according to claim 3 wherein said termination and/or polyadenylation sequence is obtained from an SCSV segment selected from the group consisting of: SCSV segment 1 (SEQ ID NO:1); SCSV segment 3 (SEQ ID NO:3); SCSV segment 4 (SEQ ID NO:4); SCSV segment 5 (SEQ ID NO:5); SCSV segment 7 (SEQ ID NO:7); and a transcription termination competent or polyadenylation competent fragment of any one of SEQ ID NOS: 1, 3–5 or 7.

6. The genetic construct according to claim 3 wherein said termination and/or polyadenylation sequence is obtained from the *Flaveria bidentis* MeA gene.

7. The genetic construct according to claim 1 further comprising a heterologous gene operably linked to said promoter.

8. The genetic construct according to claim 3 further comprising a heterologous gene operably linked to said promoter and to said termination and/or polyadenylation sequence.

9. The genetic construct according to claim 4 further comprising a heterologous gene operably linked to said promoter and to said termination and/or polyadenylation sequence.

10. The genetic construct according to claim 7 wherein said heterologous gene is selected from the group consisting of:

a) a resistance gene against a plant virus, bacterium, fungus, nematode or other pathogen;

b) a plant virus resistance gene that confers resistance against a virus selected from the group consisting of: alfalfa mosaic virus, subterranean clover stunt virus, subterranean clover mottle virus, subterranean clover red leaf virus, potato leafroll virus, tomato spotted wilt virus, bean yellow mosaic virus, white clover mosaic virus, clover yellow vein virus, potato virus X (PVX), potato virus Y (PVY) potato virus S (PVS), potato virus M (PVM) potato virus A (PVA), cucumber mosaic virus, rice ragged stunt virus and barley yellow dwarf virus;

c) a gene to improve nutritional value of plants including sunflower high sulphur gene SF8;

d) a bloat resistance gene;

e) an antibody gene;

f) a cereal thionin and ribosome inactivating protein gene;

g) an insect resistance gene including BT toxin gene and proteinase inhibitor gene obtained from *Nicotiana alata;* h) a selectable marker gene that confers resistance against kanamycin, phosphinothricin, spectinomycin or hygromycin;

i) a reporter gene including GUS, CAT and pigment genes; and j) a gene encoding a regulatory protein which modulates expression of a gene in plant cells.

11. A genetic construct comprising an isolated SCSV promoter operable in a plant cell and at least one restriction endonuclease site downstream of said promoter to facilitate insertion of a heterologous gene operably linked to said promoter, wherein said SCSV promoter comprises a nucleotide sequence obtained from the group consisting of:

(i) SEQ ID NO: 1 or a sequence complementary thereto;

(ii ) SEQ ID NO: 3 or a secuence complementary thereto;

(iii) SEQ ID NO: 4 or a sequence complementary thereto;

(iv) SEQ ID NO: 5 or a sequence complementary thereto;

(v) SEQ ID NO: 7 or a sequence complementary thereto; and (vi) a fraament of any one of (i) to (v), wherein said fragment is operable in a plant cell.

12. The genetic construct according to claim 11 further comprising a termination and/or polyadenylation sequence obtained from SCSV, wherein said termination and/or polyadenylation sequence is located at the 3' end of said heterolocrous gene when said gene is inserted into said restriction endonuclease site.

13. The genetic construct according to claim 12 wherein said termination and/or polyadenylation sequence is obtained from an SCSV segment selected from the group consisting of: SCSV segment 1 (SEQ ID NO:1); SCSV segment 3 (SEQ ID NO:3); SCSV segment 4 (SEQ ID NO:4); SCSV segment 5 (SEQ ID NO:5); SCSV segment 7 (SEQ ID NO:7); and a transcription termination competent or polyadenylation competent fragment of any one of SEQ ID NOS: 1, 3–5 or 7.

14. The genetic construct according to claim 12 wherein said termination and/or polyadenylation sequence is obtained from the *Flaveria bidentis* MeA gene.

15. The genetic construct according to claim 11 or 12 further comprising a heterologous gene selected from the group consisting of:

a) a resistance gene against a plant virus, bacterium, fungus, nematode or other pathogen;

b) a plant virus resistance gene that confers resistance against a virus selected from the group consisting of; alfalfa mosaic virus, subterranean clover stunt virus, subterranean clover mottle virus, subterranean clover red leaf virus, potato leafroll virus, tomato spotted wilt virus, bean yellow mosaic virus, white clover mosaic virus, clover yellow vein virus, potato virus X (PVX), potato virus Y (PVY), potato virus S (PVS), potato virus M (PVM) potato virus A (PVA), cucumber mosaic virus, rice ragged stunt virus and barley yellow dwarf virus;

c) a gene to improve nutritional value of plants including sunflower high sulphur gene SF8;

d) a bloat resistance gene;

e) an antibody gene;

f) a cereal thionin and ribosome inactivating protein gene;

g) an insect resistance gene including BT toxin gene and proteinase inhibitor gene obtained from *Nicotiana alata;* h) a selectable marker gene that confers resistance against kanamycin, phosphinothricin, spectinomycin or hygromycin;

i) a reporter gene including GUS, CAT and pigment genes; and j) a gene encoding a regulatory protein which modulates expression of a gene in plant cells.

16. A genetic construct comprising at least two heterologous genes. wherein each of said heterologous genes is operably linked to an isolated nanovirus promoter operable in a plant cell, wherein said promoter is obtained from a seqment of the subterranean clover stunt virus (SCSV) genome selected from the group consisting of:
  (i) SCSV secment 1 (SEO ID NO: 1);
  (ii) SCSv segment 3 (SEO ID NO: 3);
  (iii) SCSV segment 4 (SEO ID NO: 4);
  (iv) SCSV seciment 5 (SEO ID NO: 5);
  (v) SCSV segment 7 (SEO ID NO: 7);
  (vi) a nucleotide seouence complementary to any one of (i) to (v); and
  (vii) a fragment of any one of (i) to (vi) which is operable in a plant cell.

17. The genetic construct according to claim 16 comprising at least two different SCSV promoters.

18. The genetic construct according to claim 16 wherein the promoters operably linked to said heteroloaous genes are the same.

19. The genetic construct according to claim 16 wherein each of said heterologous genes is operably linked to a termination and/or polyadenylation sequence.

20. The genetic construct according to claim 19 wherein the termination and/or polyadenylation sequences linked to said heteroloaous genes are the same.

21. The genetic construct according to claim 19 wherein the termination and/or polyadenylation sequences linked to said heteroloaous aenes are different.

22. The genetic construct according to claim 19 wherein at least one termination and/or polyadenylation sequence is obtained from an SCSV segment selected from the group consisting of SCSV segment 1 (SEQ ID NO:1); SCSV segment 3 (SEQ ID NO:3); SCSV segment 4 (SEQ ID NO:4); SCSV segment 5 (SEQ ID NO:5); SCSV segment 7 (SEQ ID NO:7); and a transcription termination competent or polyadenylation competent fragment of any one of SEQ ID NOS: 1, 3–5 or 7.

23. The genetic construct according to claim 19 wherein at least one termination and/or polyadenylation sequence is obtained from the MEA gene of *Flaveria biderntis*.

24. The genetic construct according to claim 16 wherein said heterologous genes are selected from the group consisting of:
  a) a resistance gene against a plant virus, bacterium, fungus, nematode or other pathogen;
  b) a plant virus resistance gene that confers resistance against a virus selected from the group consisting of: alfalfa mosaic virus, subt erranean clover stunt virus, subterranean clover mottle virus, subterranean clover red leaf virus, potato leafroll virus, tomato spotted wilt virus, bean yellow mosaic virus, white clover mosaic virus, clover yellow vein virus, potato virus X (PVX), potato virus Y (PVY), potato virus S (PVS), potato virus M (PVM), potato virus A (PVA), cucumber mosaic virus, rice ragged stunt virus and barley yellow dwarf virus;
  c) a gene to improve nutritional value of plants including sunflower high sulphur gene SF8;
  d) a bloat resistance gene;
  e) an antibody gene;
  f) a cereal thionin and ribosome inactivating protein gene;
  g) an insect resistance gene including BT toxin gene and proteinase inhibitor gene obtained from *Nicotiana alata;*
  h) a selectable marker gene that confers resistance against kanamycin, phosphinothricin, spectinomycin or hygromycin;
  i) a reporter gene including GUS, CAT and pigment genes; and
  j) a gene encoding a regulatory protein which modulates expression of a gene in plant cells.

25. A method of expressing a foreign gene in a plant cell said method comprising introducing into said plant cell the genetic construct according to claim 11 wherein a foreign gene is operably linked to the promoter on said genetic construct.

26. The method according to claim 25 wherein the foreign gene is selected from the group consisting of:
  a) a resistance gene against a plant virus, bacterium, fungus, nematode or other pathogen;
  b) a plant virus resistance gene that confers resistance against a virus selected from the group consisting of: alfalfa mosaic virus, subterranean clover stunt virus, subterranean clover mottle virus, subterranean clover red leaf virus, potato leafroll virus, tomato spotted wilt virus, bean yellow mosaic virus, white clover mosaic virus, clover yellow vein virus, potato virus X (PVX), potato virus Y (PVY), potato virus S (PVS), potato virus M (PVM), potato virus A (PVA), cucumber mosaic virus, rice ragged stunt virus and barley yellow dwarf virus;
  c) a gene to improve nutritional value of plants including sunflower high sulphur gene SF8;
  d) a bloat resistance gene;
  e) an antibody gene;
  f) a cereal thionin and ribosome inactivating protein gene;
  g) an insect resistance gene including BT toxin gene and proteinase inhibitor gene obtained from *Nicotiana alata;*
  h) a selectable marker gene that confers resistance against kanamycin, phosphinothricin, spectinomycin or hygromycin;
  i) a reporter gene including GUS, CAT and pigment genes; and
  j) a gene encoding a regulatory protein which modulates expression of a gene in plant cells.

27. A method of expressing at least two foreign genes in a plant cell, said method comprising introducing into said plant cell the genetic construct according to claim 16.

28. A transgenic plant comprising an SCSV promoter introduced to said plant and a heterologous gene operably linked to said SCSV promoter, wherein said SCSV promoter comprises a nucleotide sequence obtained from the group consisting of:
  (i) SEQ ID NO: 1 or a sequence complementary thereto;
  (ii) SEQ ID NO: 3 or a sequence complementary thereto;
  (iii) SEQ ID NO: 4 or a sequence complementary thereto;
  (iv) SEQ ID NO: 5 or a sequence complementarv thereto;
  (v) SEQ ID NO: 7 or a sequence comtlementarv thereto: and
  (vi) a fragment of any one of (i) to (v), wherein said fragment is operable in a plant cell.

29. The transgenic plant according to claim 28 wherein said heterologous gene is selected from the group consisting of:
  a) a resistance gene against a plant virus bacterium, fungus, nematode or other pathogen;
  b) a plant virus resistance gene that confers resistance against a virus selected from the group consisting of:

alfalfa mosaic virus, subterranean clover stunt virus, subterranean clover mottle virus, subterranean clover red leaf virus, potato leafroll virus, tomato spotted wilt virus, bean yellow mosaic virus, white clover mosaic virus, clover yellow vein virus, potato virus X (PVX), potato virus Y (PVY), potato virus S (PVS), potato virus N (PVM), potato virus A (PVA), cucumber mosaic virus, rice ragged stunt virus and barley yellow dwarf virus;

c) a gene to improve nutritional value of plants including sunflower high sulphur gene SF8;

d) a bloat resistance gene;

e) an antibody gene;

f) a cereal thionin and ribosome inactivating protein gene;

g) an insect resistance gene including BT toxin gene and proteinase inhibitor gene obtained from *Nicotiana alata;* h) a selectable marker gene that confers resistance against kanamycin, phosphinothricin, spectinomycin or hygromycin;

i) a reporter gene including GUS, CAT and pigment genes; and j) a gene encoding a regulatory protein which modulates expression of a gene in plant cells.

30. The transgenic plant according to claim 28 or 29 wherein said heteroloaous gene is oderably linked to a terminator and/or polyadenylation sequene obtained from SCSV.

31. The transgenic plant according to claim 30 wherein said terminator and/or polyadenylation sequence is obtained from the *Flaveria bidentis* MeA gene.

32. A transgenic plant comprising the genetic construct according to claim 16.

33. An isolated SCSV promoter sequence obtained from a nucleotide sequence selected from the group consisting of: SCSV segment 1 (SEQ ID NO:1); SCSV segment 3 (SEQ ID NO:3); SCSV segment 4 (SEQ ID NO:4); SCSV segment 5 (SEQ ID NO:5); SCSV segment 7 (SEQ ID NO:7); and a fragment of any one of SEQ ID NOS: 1, 3–5 or 7.

34. An isolated transcription terminator sequence of SCSV obtained from a nucleotide sequence selected from the group consisting of SCSV segment 1 (SEQ ID NO:1); SCSV segment 3 (SEQ ID NO:3); SCSV segment 4 (SEQ ID NO:4); SCSV segment 5 (SEQ ID NO:5); SCSV segment 7 (SEQ ID NO:7); and a transcription termination competent or polyadenylation competent fragment of any one of SEQ ID NOS: 1, 3–5 or 7.

35. The genetic construct of claim 6 wherein the termination and/or polyadenylation sequence comprises the nucleotide sequence as set forth in SEQ ID NO:8 or a transcription termination competent or polyadenylation competent fragment thereof.

36. The genetic construct of claim 14 wherein the termination and/or polyadenylation sequence comprises the nucleotide sequence as set forth in SEQ ID NO:8 or a transcription termination competent or polyadenylation competent fragment thereof.

37. The genetic construct of claim 23 wherein the termination and/or polyadenylation sequence comprises the nucleotide sequence as set forth in SEQ ID NO:8 or a transcription termination competent or polyadenylation competent fragment thereof.

38. The transgenic plant of claim 31 wherein the termination and/or polyadenylation sequence comprises the nucleotide sequence as set forth in SEQ ID NO:8 or a transcription termination competent or polyadenylation competent fragment thereof.

* * * * *

SEQUENCE LISTING (1) GENERAL INFORMATION:

(iii) NUMBER OF SEQUENCES: 34

(2) INFORMATION FOR SEQ ID NO:1:

(i) SEQUENCE CHARACTERISTICS:
      (A) LENGTH: 1001 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
TAGTATTACC CCCGTGCCGG GATCAGAGAC ATTTGACCAA TAGTTGACTA GTATAATAGC      60

CCTTGGATTA AATGACACGT GGACGCTCAG GATCTGTGAT GCTAGTGAAG CGCTTAAGCT     120

GAACGAATCT GACGGAAGAG CGTTCACACT TAGATCTAGT TAGCGTACTT AGTACGCGTT     180

GTCTTGGGTC TATAAATAGA GTGCTTCTGA ACAGATTGTT CAGAATTTCA TAGCGAGATG     240

GATTCTGGTG ATGGTTACAA TACATACTCA TATGAAGAAG GTGCTGGAGA TGCGAAGAAG     300

GAAGTTTTAT ATAAAATAGG TATTATTATG TTATGTATTG TAGGGATTGT AGTTTTATGG     360

GTTTTAATTA TATTATGTTG TGCTGTTCCT CGCTATGCTA AATCAACGAT GGACGCTTGG     420

TTATCTTCGT CTTCTATTAT GAAGAGGAAG ATGGCTTCAA GGATTACTGG TACTCCGTTT     480

GAAGAAACTG GTCCTCATCG TGAAAGAAGA TGGGCTGAAA GAAGAACTGA AGCGACGAAC     540

CAGAATAATA ATGATAATGT AAATAGATTT AGTTGATATG TTGTAATTTT ATATGGATTA     600

ATGAGAATTA TTATTATTCT GTTCTTCGTC TGTGTTTTTT AAGCTTTTTC TGTGTTTTAA     660

TGGCGTCTGG AGAGAGAAAG GAATAATTGT AAGGTAGACG ACGATGTAGT GGATTACAGT     720

TGTCTTTACT TCGCCTCGAA GAAAGACACA TTTCAAGTTG TGAGTGTTAT TGCTTTTGAG     780

GAAGCTTCCT CGAAGCAGCG TATAACTTTA ATTTGAATTT GGTTTTGGCG CGTTAGTGAA     840

ATTGCGGCTG TAAACGTGTC AAGTTGTGAG TGGCTGAAAT AAGATAATAG ATATATTATT     900

ATTGTTTTAA TTTAATTCCG CGAAGCGATA TGTTAAGTGA TAAATGAAAC GAAGCGTTTT     960

GATGACGTCA TATGTCTCCG TGCCTACGTC AGCACGGGGC T                       1001
```

(2) INFORMATION FOR SEQ ID NO:2:

(i) SEQUENCE CHARACTERISTICS:
      (A) LENGTH: 1022 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

```
TAGTATTACC CGACCTTGCC ACACCTCCTT GGAACACTTT CTCTCTCTAG AAAGTGTGAG      60

ACTTTCTCTC TCTAAGCTTA TATGGCTAGA AGGTACTGTT TTACATTAAA TTACGCTACT     120
```

```
GAGATAGAGA GAGAAACATT CCTCTCCCTC TTCTCTCAAG ACGAATTAAA CTATTTCGTT      180

GTCGGCGACG AAACTGCAAC TACTGGACAG AAACACCTCC AGGGATTTGT ATCGTTCAAG      240

AACAAAATTC GTCTTGGTGG ATTGAAGAAG AAATTTGGTA ATCGAGCTCA CTGGGAAATT      300

GCGAGAGGCA GCGATTCTCA GAATCGCGAT TATTGCTGTA AAGAAACCCT AATTTCTGAA      360

ATTGGGATTC CGGTCATGAA GGGTTCGAAC AAGCGGAAGA CGATGGAGAT TTATGAAGAG      420

GATCCCGAAG AAATGCAATT GAAGGATCCA GATACTGCTC TTCGATGTAA GGCGAAGAAA      480

TTGAAAGAGG AATATTGTTC CTGTTATGAT TTTCAGAAAC TCCGTCCATG GCAAATTGAG      540

CTTCACGAGG ATTTAATGGC GGAACCAGAT GATCGGAGTA TCATCTGGGT CTATGGTTCA      600

GACGGAGGAG AAGGAAAGAC GAGCTTCGCG AAGGAATTAA TCAGGTATGG ATGGTTTTAT      660

ACAGCCGGAG GGAAGACCCA GGACGTATTA TATATGTATG CTCAAGACCC AGAGAGGAAT      720

ATTGCGTTTG ATGTTCCCAG GTGTTCTTCG GAGATGATGA ACTATCAGGC GATGGAGATG      780

TTGAAGAACA GAGTTTTTGC AAGTACAAAA TATAGGCCTG TAGATCTTTG TATTAGGAAG      840

TTAGTTCATT TAATTGTGTT TGCCAACGTG GCACCTGACC CCACGCGCAT AAGTGAGGAC      900

AGACTTGTAA TTATCAATTG TTGAATAAAA GAATATATAT TATTGTTTTA ATTTAATTCC      960

GCGAAGCGGT AGCCGGTCAT AACACTGTTG CCCTTGGAAC ACTATATATA GCAAGGTCGG     1020

CT                                                                   1022

(2) INFORMATION FOR SEQ ID NO:3:

(i) SEQUENCE CHARACTERISTICS:
        (A) LENGTH: 991 base pairs
        (B) TYPE: nucleic acid
        (C) STRANDEDNESS: single
        (D) TOPOLOGY: linear (ii) MOLECULE TYPE: DNA  (genomic)

(xi) SEQUENCE DESCRIPTION: SEQ ID NO:3:

TAGTATTACC CCCGTGCCGG GATCAGAGAC ATTTGACCAA TAGTTGACTA TGAATAATAG       60

CCCTTGGATT AGATGACACG TGGACGCTCA GGATCTGTGA TGCTAGTGAA GCGCTTAAGC      120

TGAACGAATC TGACGGAAGA GCGGACATAC GCACATGGAT TATGGCCCAC ATGTCTAAAG      180

TGTATCTCTT TACAGCTATA TTGATGTGAC GTAAGATGCT TTACTTCGCC TCGAAGTAAA      240

GTAGGAAATT GCTCGCTAAG TTATTCTTTT CTGAAAGAAA TTAATTTAAT TCTAAATTAA      300

ATTAAATGAG TGGCTATAAA TAGATGTTTC GTCTTCGTTG TTTTACAACG AAGCTTAGAA      360

TCTTGTGTTA ATGGCGTTAA GGTATTTCTC TCATCTTCCT GAAGAACTGA AGGAGAAGAT      420

TATGAACGAG CACTTGAAGG AAATTAAGAA GAAGGAATTT CTAGAGAATG TAATTAAAGC      480

TGCGTGTGCT GTGTTCGAAG GTTTAACAAA GAAGGAGTCT GTTGAAGAAG ACGACATACT      540

ACGCTTCTCT GGGTTTCTGG AAGGTCTGTC TGCATATTAT GCAGAGGCGA CGAAGAAGAA      600

GTGTTTAGTT AGATGGAAGA AGAGCGTTGC AATAAATCTG AAATGGAGAG TTATGGAGGA      660

GATGCATTAC AAGCTTTATG GATTTGCAGA CATGGAAGAT TTATATTATT CAGAGTTAGG      720

GTTTCCTAAT TACGGTGAAG ACGATGTAGC TTATCACGAT GGTGCAATTG TAAATTGTAA      780

GCAATTAGAA GTTGTATTTG ATGATTTAGG TATTGAGTTT ATGTCTATTG TAATTGATAG      840

AGGTTCTATT AAGATAGAAT TATGAGATGT AATTGTGATT AATGAATAAA GAGTTGTTAT      900

TATTCTTTGA ATTACTCCGC GAAGCGGTGT GTTATGTTTT TGTTGGAGAC ATATGACGTC      960

ATATGTCTCG CCGACAGGCT GGCACGGGGC T                                    991
```

(2) INFORMATION FOR SEQ ID NO:4:

(i) SEQUENCE CHARACTERISTICS:
        (A) LENGTH: 1002 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
TAGTATTACC CCGTGCCGGG ATCAGAGACA TTTGACTAAA TGTTGACTTG GAATAATAGC      60

CCTTGGATTA GATGACACGT GGACGCTCAG GATCTGTGAT GCTAGTGAAG CGCTTAAGCT     120

GAACGAATCT GACGGAAGAG CGGACAAACG CACATGGACT ATGGCCCACT GCTTTATTAA     180

AGAAGTGAAT GACAGCTGTC TTTGCTTCAA GACGAAGTAA AGAATAGTGG AAAACGCGTA     240

AAGAATAAGC GTACTCAGTA CGCTTCGTGG CTTTATAAAT AGTGCTTCGT CTTATTCTTC     300

GTTGTATCAT CAACGAAGAA GTTAAGCTTT GTTCTGCGTT TTAATGGCGG ACTGGTTTCA     360

CAGTGCGCTT AAGACATGTA CTCATGTCTG TGATTTTTCA GATATTAAGG CGTCTTCACA     420

ACAGGATTTC TTCTGTTGTG ATAGTATGCG AGGTAAATTA TCTGAACCTA GGAAGGTGTT     480

GTTAGTTAGT TGTTTTGTAA GTTTTACTGG TAGTTTTTAT GGAAGTAATA GGAATGTTAG     540

AGGTCAAGTT CAGTTGGGTA TGCAGCAAGA TGATGGCGTT GTTCGTCCAA TAGGATATAT     600

TCCTATTGGG GGTTATTTGT ATCATGATGA TTATGGATAT TATCAAGGAG AGAAGACGTT     660

CAATCTGGAC ATCGAGTCAG ATTATCTGAA GCCTGATGAA GATTTTTGGA AGAGATTTAC     720

AATTAATATT GTAAATGATA AAGGATTAGA TGATAGGTGT GATGTAAAAT GTTATGTAGT     780

TCATACGATG CGTATTAAGG TGTAATTGTT ATTATCAATA AAAGAATTTT TATTGTTATT     840

GTGTTATTTG GTAATTTATG CTTATAAGTA ATTCTATGAT TAATTGTGAA TTAATAAGAC     900

TAATGAGGAT AATAATTGAA TTTGATTAAA TTAACTCTGC GAAGCTATAT GTCTTTCACG     960

TGAGAGTCAC GTGATGTCTC CGCGACAGGC TGGCACGGGG CT                      1002
```

(2) INFORMATION FOR SEQ ID NO:5:

(i) SEQUENCE CHARACTERISTICS:
        (A) LENGTH: 998 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
TAGTATTACC CCGTGCCGGG GTCAGAGACA TTTGACTAAA TATTGACTTG GAATAATAGC      60

CCTTGGATTA GATGACACGT GGACGCTCAG GATCTGTGAT GCTAGTGAAG CGCTTAAGCT     120

GAACGAATCT GACGGAAGAG CGTCATGGTC CACATGTCTA AAGAATAATG CTTTACAGCT     180

GTATTGATTT GACTTTACGC GCTTTACTTT AATTGCTTTA AGTAAAGTAA GATGCTTTAC     240

TTTGCTCGCG ACGAAGCAAA GTGATTGTAG CTGCAGAAAT TGATGCTTTA ATTACCGGGT     300

AACACGGTTT GATTGTGGGT ATAAATATGT TCTGTTCGTT TTCTTCGTTG TCATTTTACA     360

ACGAAGATGG TTGCTGTTCG ATGGGGAAGA AAGGGTCTGA GGTCTCAAAG GAGAAAATAT     420

TCGCGAATTG CTTACAAACC TCCTTCGTCT AAGGTTGTAA GTCATGTGGA GTCTGTTCTG     480

AATAAGAGAG ATGTTACTGG AGCGGAGGTT AAGCCATTCG CTGATGGTTC AAGGTATAGT     540
```

```
ATGAAGAAGG TAATGTTGAT TGCAACATTA ACTATGGCTC CTGGAGAATT AGTTAATTAT      600

CTTATTGTGA AGAGTAATTC GCCTATTGCG AATTGGAGTT CGTCTTTCAG TAATCCTTCG      660

TTGATGGTGA AAGAGTCTGT TCAAGATACA GTTACGATTG TTGGAGGAGG AAAGCTTGAG      720

TCTTCTGGTA CTGCTGGTAA AGATGTAACT AAGTCTTTTA GGAAGTTTGT TAAGCTGGGT      780

TCAGGTATTA GTCAGACCCA GCATTTGTAT TTAATTATTT ATTCCAGTGA TGCGATGAAG      840

ATCACACTGG AGACGAGAAT GTATATTGAT GTATAATTGT GATGATTAAT GAATAAAGAG      900

TTGTTTTTAT TCTTTGAATT ACTCCGCGAA GCGGTGTGTT ATGTTTTTGT TGGAGACATA      960

TGACGTCATA TGTCTCCGCG ACAGGCTGGC ACGGGGCT                              998
```

(2) INFORMATION FOR SEQ ID NO:6:

(i) SEQUENCE CHARACTERISTICS:
        (A) LENGTH: 1017 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
CAGTATTACC GCACCTCGCT TACCCTCCTC GCTTCCCTGG GCCCACTATG CCTACTAGAC       60

AAAGCACTAG TTGGGTGTTC ACACTTAACT TTGAGGGCGA AATTCCTATT TTGCCCTTTA      120

ATGAAAGCGT TCAGTACGCT TGTTGGCAGC ATGAGAGAGT GGGACACGAT CATTTACAGG      180

GATTTATACA ATTTAAATCC CGCAACACTA CATTGCGTCA GGCTAAGTAT ATTTTTAATG      240

GACTGAATCC TCATCTGGAA ATTGCTAGGG ATGTAGAGAA GGCGCAATTG TACGCGATGA      300

AGGAAGATAG TAGAGTAGCT GGTCCCTGGG AGTATGGGTT GTTTATTAAG AGAGGATCGC      360

ATAAGCGTAA GCTGATGGAG AGATTTGAAG AAGATGGAGA AGAGATGAAA ATTGCTGATC      420

CCTCTCTCTA TAGGCGTTGT CTATCAAGGA AGATGGCTGA AGAACAACGT TGTTCTTCTG      480

AGTGGAATTA TGACTTACGC CCTTGGCAAG AAGAAGTGAT GCATTTGTTA GAGGAAGAAC      540

CAGATTATAG AACGATAATC TGGGTGTATG GACCTGCTGG TAATGAAGGC AAATCTACAT      600

TTGCAAGACA TCTGTCATTG AAAGATGGTT GGGGTTATCT GCCTGGAGGA AAGACACAAG      660

ATATGATGCA TCTTGTGACT GCTGAGCCTA AGAATAATTG GGTATTTGAC ATACCCAGAG      720

TTAGTTCAGA GTATGTGAAT TATGGTGTAA TAGAACAGGT TAAGAATAGG GTAATGGTGA      780

ATACTAAGTA TGAGCCATGT GTAATGCGGG ATGATAATCA TCCTGTTCAT GTAATTGTGT      840

TTGCAAATGT ACTCCCAGAT TTGGGAAAAT TAAGTGAAGA TAGAATAAAA TTAATTCGTT      900

GTTGAAAACT CTGCGAAGGC AGAAGTTATA AAAAAAATGT GTTTTGAGAG AAGTCCCACA      960

TCGGGTAGTT CGCGAAACAG GGTGAGGGAA GCGAGCAATA TAAGGCGAGG TGCGTAT       1017
```

(2) INFORMATION FOR SEQ ID NO:7:

(i) SEQUENCE CHARACTERISTICS:
        (A) LENGTH: 988 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
TAGTATTACC CCGTGCCGGG ATCAGAGACA TTTGACTAAA TATTGACTTG GAATAATAGC       60

CCTTGGATTA GATGACACGT GGACGCTCAG GATCTGTGAT GCTAGTGAAG CGCTTAAGCT      120
```

-continued

```
GAACGAATCT GACGGAAGAG CGGACATACG CACATGGATT ATGGCCCACA TGTCTAAAGT      180

GTATCTCTTT ACAGCTATAT TGATGTGACG TAAGATGCTT TACTTCGCTT CGAAGTAAAG      240

TAGGAAATTG CTCGCTAAGT TATTCTTTTC TGAAAGAAAT TAATTTAATT CTAATTAAAT      300

TAAATGAGTG GCTATAAATA GTGTCGATGC TGCCTCACAT CGTATTCTTC TTCGCATCGT      360

CTGTTCTGGT TTTAAGCGAT GGTCAGTTTT AGTTTTCCTG AGATATACGA TGTGAGCGAC      420

GATGTTCTTG TAAGCGATAG CAGAAGAAGT GTAGCTGTTG AGGTCGAAGA GAAGGTTCAA      480

GTGATTAACG TGAAGGTACT GAGGTTGATT GAAGCTGTTG ATGAAGATAG AGTTGGAGTG      540

AAGGTTATGT TTCGTCTGTG TTACAGATAC AGACGAGAAC TGAAGATTAC GTTGTTGGGT      600

TGTAAGATGG AGCTATGGAC TTCGTTGAAG TCTTCAGGCA AGTATTCAGT TCAATCTTTG      660

TTGCAGAGGA AGCTTAATGG TATATGTGTT AGTAATTACT GTATAGGTAT TGATATGTTT      720

GTAAGTAATG TTAAAGAGTT GATTAATAGA TGTAAATGGA TTACATCTGT TCAAGGTGTT      780

AATCCTATAT GTTGTTTGTA TCATATGGAC GAAGAGTAAT TAATAGTAAT TATGATTAAT      840

TATGAGATAA GAGTTGTTAT TAATGCTTAT GAGGAATAAA GAATGATTAA TATTGTTTAA      900

TTTTATTCGC GAAGCGGTGT GTTATGTTTT TGTTGGAGAC ATCACGTGAC TCTCACGTGA      960

TGTCTCCGCG ACAGGCTGGC ACGGGGCT                                        988

(2) INFORMATION FOR SEQ ID NO:8:

(i) SEQUENCE CHARACTERISTICS:
        (A) LENGTH: 905 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

TAAGTTTAGC GGGGGAAAAA GGACAGTTGA TCTGTTGCTG TTTGCAATTT TTTAAAGGGT       60

ATGTTGTCAG ATGCATGTTG TAATGCTTGT TCATCAACAC ATTATATGAC TTGCAGTTGC      120

TGATGATGGA AACTTAAAGC TTAATACTAC TTTTGTTTAT TCACTTACAA ATACCGGTTG      180

GGTTCTTTGT TTATCAGGAA TGCTCATTGT ATGTAGCTAA AAGCTGGCCG TTTATAGTTT      240

TATTGCCCTA AATCTGGTAC TTTATCCAAA AACTAAATTT GGAAACATCA AATACTTTTT      300

TCAAGAATGA TAAACTCGTA CACTCTCTAG GGTACTCCTG AAATTTAAAT CAAAATCCAA      360

AACCGCTTAG GAAGGAACAT ATGTGATAAG AACTGAAATT TCGATTAACT ATTACAAGAT      420

AGTCGGCCCA ATTCGAGAGG ACTAGTCTCC GATTACAAGG AGTAAATATC TTAATCTTGA      480

TAAACAAAAC ACATATAAAA AACCTAAAAA TATAGGAACA TAATACATAA ACTAAAAGTT      540

GTGGGAACAG TTACAAATCT GCAGTCTCAC TCCCTAAATT TGTGAGTCAC CTTTCACCTC      600

CAAGTTTTCG AATGTTCTCC CACCATTCAC TTTCCCTCCA CCCGGATTCC CTCCAATTAA      660

TAGCTGACAC AACCCGTTTT GACCCAACAT TGGGTTCGTA TCAATACATC CGGCCCGGAA      720

AATCGACTTG TCCTCAAGTC GAAAGGAGGG GAATTATTGT GCCAAGCAAA AAGCCATTCG      780

ATTGGAGGTT GATGGATGAT TTCCTTGTGT TTGAAAGCTT CAAAAGATCC GGCCAAATCA      840

GCTTTTAATG CCTCTTGAAC TGTAGCCACA ACACCACTTT GAAACCTCAA ATCTGTTTTG      900

AATTC                                                                 905

(2) INFORMATION FOR SEQ ID NO:9:
```

(i) SEQUENCE CHARACTERISTICS:
       (A) LENGTH: 7 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:9:

TATAAAT                                                                 7

(2) INFORMATION FOR SEQ ID NO:10:

(i) SEQUENCE CHARACTERISTICS:
       (A) LENGTH: 7 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:10:

TATATAT                                                                 7

(2) INFORMATION FOR SEQ ID NO:11:

(i) SEQUENCE CHARACTERISTICS:
       (A) LENGTH: 7 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:11:

AATATAA                                                                 7

(2) INFORMATION FOR SEQ ID NO:12:

(i) SEQUENCE CHARACTERISTICS:
       (A) LENGTH: 3 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:12:

TGA                                                                     3

(2) INFORMATION FOR SEQ ID NO:13:

(i) SEQUENCE CHARACTERISTICS:
       (A) LENGTH: 3 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:13:

TAA                                                                     3

(2) INFORMATION FOR SEQ ID NO:14:

(i) SEQUENCE CHARACTERISTICS:
       (A) LENGTH: 6 base pairs
       (B) TYPE: nucleic acid
       (C) STRANDEDNESS: single (D) TOPOLOGY: linear (ii) MOLECULE TYPE: DNA (xi) SEQUENCE DESCRIPTION: SEQ ID NO:14:

AATTAT                                                                          6

(2) INFORMATION FOR SEQ ID NO:15:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

AATAAA                                                                          6

(2) INFORMATION FOR SEQ ID NO:16:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

GGCGTGCGTC GGCCATGGCG CTATGAAATT CTGAAC                                          36

(2) INFORMATION FOR SEQ ID NO:17:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

GGCGTGCGTC GGGGATCCTA TGTTGTAATT TTATATGG                                        38

(2) INFORMATION FOR SEQ ID NO:18:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

GGCGTGCGTC GGCCATGGAA GCTTAGAGAG AGAAAG                                          36

(2) INFORMATION FOR SEQ ID NO:19:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

GGCGTGCGTC GGGGATCCAA TAAAAGAATA TATATTATTG     40

(2) INFORMATION FOR SEQ ID NO:20:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

CTCACTATAG AACCATGGAC ACAAGATTCT AAG     33

(2) INFORMATION FOR SEQ ID NO:21:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

CTCACTAAAG GGGGATCCTG AGATGTAATT GTG     33

(2) INFORMATION FOR SEQ ID NO:22:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

CTCACTATAG AACCATGGAA ACGCAGAACA AAG     33

(2) INFORMATION FOR SEQ ID NO:23:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:23:

CTCACTAAAG GGGGATCCTA ATTGTTATTA TCA     33

(2) INFORMATION FOR SEQ ID NO:24:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

CTCACTATAG AACCATGGTC GTTGTAAAAT GAC     33

(2) INFORMATION FOR SEQ ID NO:25:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:25:

```
CTCACTAAAG GGGGATCCTA ATTGTGATGA TT                                32
```

(2) INFORMATION FOR SEQ ID NO:26:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:26:

```
CTCACTATAG AACCATGGTG GGCCCAGGGA AGCGA                             35
```

(2) INFORMATION FOR SEQ ID NO:27:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:27:

```
CTCACTAAAG GGGGATCCTG AAAACTCTGC GAA                               33
```

(2) INFORMATION FOR SEQ ID NO:28:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:28:

```
CTCACTATAG AACCATGGCT TAAAACCAGA ACA                               33
```

(2) INFORMATION FOR SEQ ID NO:29:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:29:

```
CTCACTAAAG GGGGATCCTA ATTAATAGTA ATTATG                            36
```

(2) INFORMATION FOR SEQ ID NO:30:

(i) SEQUENCE CHARACTERISTICS:

```
        (A) LENGTH: 8 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:30:

TGTGTTTT                                                                 8

(2) INFORMATION FOR SEQ ID NO:31:

(i) SEQUENCE CHARACTERISTICS:
        (A) LENGTH: 7 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:31:

TTGTTTT                                                                  7

(2) INFORMATION FOR SEQ ID NO:32:

(i) SEQUENCE CHARACTERISTICS:
        (A) LENGTH: 5 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:32:

TTGTT                                                                    5

(2) INFORMATION FOR SEQ ID NO:33:

(i) SEQUENCE CHARACTERISTICS:
        (A) LENGTH: 8 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:33:

TTATTGTT                                                                 8

(2) INFORMATION FOR SEQ ID NO:34:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:34:

TTGTTT                                                                   6
```